US012600729B2

(12) United States Patent
Lu et al.

(10) Patent No.: US 12,600,729 B2
(45) Date of Patent: Apr. 14, 2026

(54) NEW-TYPE BENZAZEPINE FUSED RING DERIVATIVE

(71) Applicant: SHANGHAI JEYOU PHARMACEUTICAL CO., LTD., Shanghai (CN)

(72) Inventors: Hongfu Lu, Shanghai (CN); Dezhi Qiu, Shanghai (CN); Jianbiao Peng, Shanghai (CN)

(73) Assignee: SHANGHAI JEYOU PHARMACEUTICAL CO., LTD., Shanghai (CN)

( * ) Notice: Subject to any disclaimer, the term of this patent is extended or adjusted under 35 U.S.C. 154(b) by 323 days.

(21) Appl. No.: 18/547,513

(22) PCT Filed: Mar. 4, 2022

(86) PCT No.: PCT/CN2022/079350
§ 371 (c)(1),
(2) Date: Aug. 23, 2023

(87) PCT Pub. No.: WO2022/184172
PCT Pub. Date: Sep. 9, 2022

(65) Prior Publication Data

US 2024/0190884 A1 Jun. 13, 2024

(30) Foreign Application Priority Data

Mar. 5, 2021 (CN) ......................... 202110264947.3
May 21, 2021 (CN) ......................... 202110559685.3
Mar. 2, 2022 (CN) ......................... 202210198716.1

(51) Int. Cl.
*C07D 487/04* (2006.01)
*A61K 31/55* (2006.01)
*A61P 13/12* (2006.01)
*C07D 491/048* (2006.01)

(52) U.S. Cl.
CPC ............ *C07D 487/04* (2013.01); *A61K 31/55* (2013.01); *A61P 13/12* (2018.01); *C07D 491/048* (2013.01)

(58) Field of Classification Search
CPC ........ C07D 487/04; A61P 13/12; A61K 31/55
See application file for complete search history.

(56) References Cited

U.S. PATENT DOCUMENTS 5,258,510 A 11/1993 Ogawa et al.
5,512,563 A 4/1996 Albright et al.
7,001,898 B2 2/2006 Chen et al.
2007/0179128 A1 8/2007 Patel et al.

FOREIGN PATENT DOCUMENTS

CN 1106802 A 8/1995
CN 1449386 A 10/2003
EP 0709386 A1 5/1996
EP 4253367 A1 * 10/2023 ................ A61P 1/16
JP 0859624 A 3/1996
WO 9105549 A1 5/1991

OTHER PUBLICATIONS

Oct. 1, 2024 the First Office Action issued in Canadian Patent Application No. 3,210,848.

Sep. 24, 2024 the First Office Action issued in Australian Patent Application No. 2022230013.

Feb. 20, 2025 extended European Search Report issued in European Patent Application No. 22762633.0.

Mar. 28, 2025 Hearing Notice issued in Indian Patent Application No. 202347065183.

DATABASE Registry-Online.

Jun. 6, 2022 International Search Report issued in International Patent Application No. PCT/CN2022/079350.

Jun. 6, 2022 Written Opinion of the International Searching Authority issued in International Patent Application No. PCT/CN2022/079350.

Oct. 30, 2023 The First Office Action issued in Indian Patent Application No. 202347065183.

RN 1060714-80-8.

Jun Matsubara, et al., Enantioselective Synthesis of the Metabolites of Vasop-ressin V2 Receptor Antagonist OPC-31260 via Lipase-Catalyzed Transesterifi-cation, Tetrahedron, 56 ( 2000 ) 4667-4682.

Serradeil-Le Gall, C., et al., Nonpeptide vasopressin receptor antagonists: development of selective and orally active V1a, V2 and V1b receptor ligands. Progress in Brain Research, 2002, vol. 139, pp. 197-210.

Decaux, G., et al., Non-peptide arginine-vasopressin antagonists: the vaptans. The Lancet, 2008, 371:1624-1632.

(Continued)

*Primary Examiner* — Sarah Pihonak
*Assistant Examiner* — Mikhail O'Donnel Robinson
(74) *Attorney, Agent, or Firm* — Houston Beshining Law Office PLLC; Liangang Ye

(57) ABSTRACT

A benzazepine fused ring derivative as represented by formula (I) or a pharmaceutically acceptable salt thereof, and the use of a compound in the diagnosis, prevention and/or treatment of diseases related to vasopressin receptors.

(I)

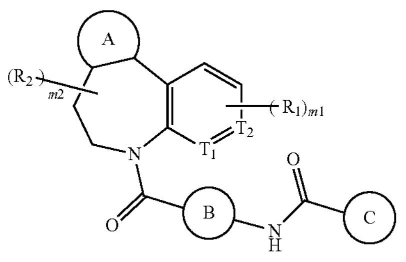

15 Claims, 1 Drawing Sheet

(56) References Cited

OTHER PUBLICATIONS

Albright, J.D., et al., 5-Fluoro-2-methyl-N-[4-(5H-pyrrolo [2, 1-c]-[1, 4]benzodiazepin-10(11 H)-ylcarbonyl)-3-chlorophenyl] benzamide (VPA-985): An orally Active Arginine Vasopressin Antagonist with Selectivity for V2 Receptors, J. Med. Chem, 1998, 41, 2442-2444.

* cited by examiner

NEW-TYPE BENZAZEPINE FUSED RING DERIVATIVE

The present application is a National Stage of International Application No. PCT/CN2022/079350, filed on Mar. 4, 2022, which claims priorities of the Chinese Patent Application No. CN202110264947.3 filed on Mar. 5, 2021, the Chinese Patent Application No. CN202110559685.3 filed on May 21, 2021, and the Chinese Patent Application No. CN202210198716.1 filed on Mar. 2, 2022, and the contents of which are incorporated herein by reference in their entireties.

TECHNICAL FIELD

The present disclosure relates to a new-type benzazepine fused ring derivative and a salt thereof. The present disclosure also relates to a use of a medicament comprising the benzazepine fused ring derivative and the salt thereof as active ingredients in the diagnosis, prevention, and/or treatment of diseases related to vasopressin receptors.

BACKGROUND

Hormones play an important role in the regulation of homeostasis in the human body, among which arginine vasopressin (AVP) is closely related to the regulation of water and sodium metabolism in the human body. Metabolic disturbances of arginine vasopressin (AVP) can cause diseases such as hyponatremia, syndrome of inappropriate antidiuretic hormone secretion, congestive heart failure, liver cirrhosis, kidney disease, hypertension, and edema. Arginine vasopressin (AVP) receptor antagonists can inhibit the combination of AVP and receptors, thereby playing a therapeutic role in the above diseases. The arginine vasopressin V2 receptor antagonist represented by Tolvaptan can increase the excretion of free water without affecting the metabolism of electrolytes, thus becoming an ideal drug for the treatment of the above diseases. However, the marketed AVP V2 receptor antagonists, such as Tolvaptan, are metabolized by liver metabolic enzymes, which produce a large number of metabolites in the body and cause severe drug-induced liver toxicity. The FDA issued a black box warning on the drug's product label, limiting its application. Therefore, developing a new-type V2 receptor antagonist with high efficiency and low side effects is very important.

CONTENT OF THE PRESENT INVENTION

In the first aspect of the present disclosure, the present disclosure provides a compound of formula (I), an optical isomer thereof, or a pharmaceutically acceptable salt thereof, (I)

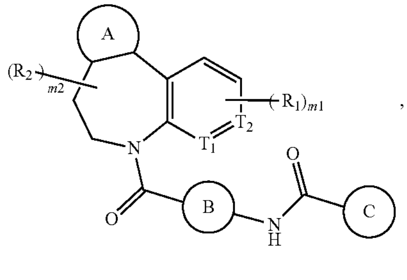

, wherein ring A is selected from 4- to 6-membered heterocyclyl and $C_{3-6}$ cycloalkyl, and the 4- to 6-membered heterocyclyl or $C_{3-6}$ cycloalkyl is optionally substituted by 1, 2, or 3 $R_A$;

ring B is selected from phenyl and 5- to 6-membered heteroaryl, and the phenyl or 5- to 6-membered heteroaryl is optionally substituted by 1, 2, or 3 $R_3$;

ring C is selected from phenyl and 5- to 6-membered heteroaryl, and the phenyl or 5- to 6-membered heteroaryl is optionally substituted by 1, 2, or 3 $R_4$;

$T_1$, $T_2$ are each independently selected from N and $C(R_T)$;

$R_1$, $R_2$, $R_3$, $R_A$, $R_T$ are each independently selected from H, F, Cl, Br, I, CN, OH, $NH_2$, $C_{1-6}$ alkyl, and $C_{1-6}$ heteroalkyl, and the $C_{1-6}$ alkyl or $C_{1-6}$ heteroalkyl is optionally substituted by 1, 2, or 3 R;

each $R_4$ is independently selected from H, F, Cl, Br, I, CN, OH, $NH_2$, $C_{1-6}$ alkyl, $C_{1-6}$ alkoxy, $C_{1-6}$ alkylamino, $C_{3-6}$ cycloalkyl, phenyl, and 5- to 6-membered heteroaryl, and the $C_{1-6}$ alkyl, $C_{1-6}$ alkoxy, $C_{1-6}$ alkylamino, $C_{3-6}$ cycloalkyl, phenyl, or 5- to 6-membered heteroaryl is optionally substituted by 1, 2, or 3 $R_{4a}$;

R, $R_{4a}$ are each independently selected from H, F, Cl, Br, I, CN, OH, $NH_2$, $C_{1-6}$ alkyl, $C_{1-6}$ alkoxy, and $C_{1-6}$ alkylamino, and the $C_{1-6}$ alkyl, $C_{1-6}$ alkoxy, and $C_{1-6}$ alkylamino are optionally substituted by 1, 2, or 3 R';

R' is selected from H, F, Cl, Br, I, CN, OH, $NH_2$, and $C_{1-6}$ alkyl;

m1, m2 are each independently selected from 0, 1, or 2;

and when ring A is selected from 4- to 6-membered heterocyclyl, the compound of formula (I) is not selected from

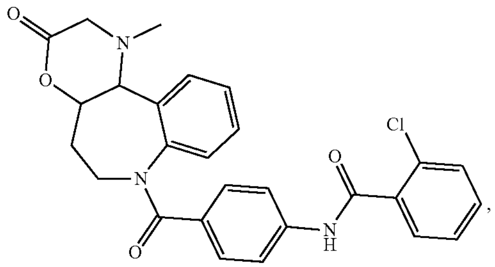

,

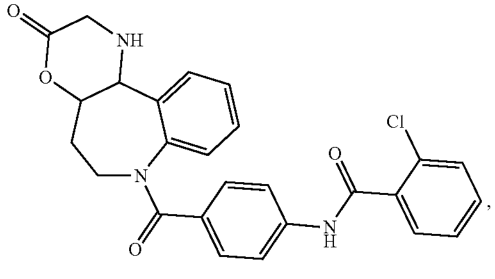

, or

-continued

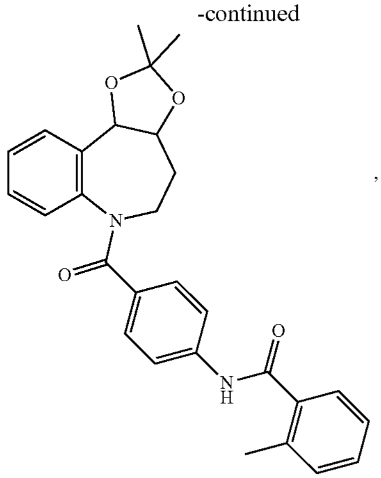

, the 4- to 6-membered heterocyclyl, $C_{1-6}$ heteroalkyl, or 5- to 6-membered heteroaryl comprises 1, 2, 3, or 4 heteroatoms or heteroatom groups independently selected from —O—, —NH—, —S—, —C(=O)—, —C(=O)O—, —S(=O)—, —$S(=O)_2$—, and N.

In the second aspect of the present disclosure, the present disclosure also provides a compound of formula (II), an optical isomer thereof, or a pharmaceutically acceptable salt thereof, (II)

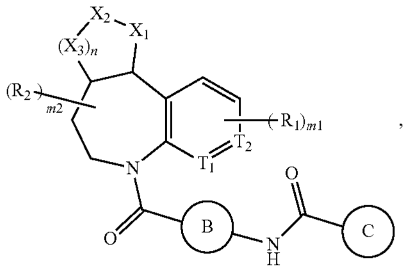

, wherein $X_1$, $X_2$, $X_3$ are each independently selected from O, $C(R_A)_2$, and $NR_A$;

ring B is selected from phenyl and 5- to 6-membered heteroaryl, and the phenyl or 5- to 6-membered heteroaryl is optionally substituted by 1, 2, or 3 $R_3$;

ring C is selected from phenyl and 5- to 6-membered heteroaryl, and the phenyl or 5- to 6-membered heteroaryl is optionally substituted by 1, 2, or 3 $R_4$;

$T_1$, $T_2$ are each independently selected from N and $C(R_T)$;

$R_1$, $R_2$, $R_3$, $R_A$, $R_T$ are each independently selected from H, F, Cl, Br, I, CN, OH, $NH_2$, $C_{1-6}$ alkyl, and $C_{1-6}$ heteroalkyl, and the $C_{1-6}$ alkyl or $C_{1-6}$ heteroalkyl is optionally substituted by 1, 2, or 3 R;

each $R_4$ is independently selected from H, F, Cl, Br, I, CN, OH, $NH_2$, $C_{1-6}$ alkyl, $C_{1-6}$ alkoxy, $C_{1-6}$ alkylamino, $C_{3-6}$ cycloalkyl, phenyl, and 5- to 6-membered heteroaryl, and the $C_{1-6}$ alkyl, $C_{1-6}$ alkoxy, $C_{1-6}$ alkylamino, $C_{3-6}$ cycloalkyl, phenyl, or 5- to 6-membered heteroaryl is optionally substituted by 1, 2, or 3 $R_{4a}$;

R, $R_{4a}$ are each independently selected from H, F, Cl, Br, I, CN, OH, $NH_2$, $C_{1-6}$ alkyl, $C_{1-6}$ alkoxy, and $C_{1-6}$ alkylamino, and the $C_{1-6}$ alkyl, $C_{1-6}$ alkoxy, and $C_{1-6}$ alkylamino are optionally substituted by 1, 2, or 3 R';

R' is selected from H, F, Cl, Br, I, CN, OH, $NH_2$, and $C_{1-6}$ alkyl;

m1, m2, n are each independently selected from 0, 1, or 2;

and when $X_1$, $X_3$ are selected from O at the same time, the compound of formula (II) is not selected from

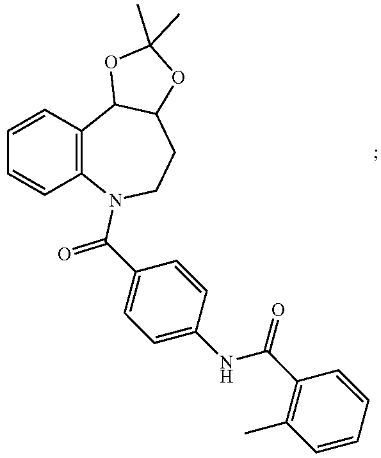 [SMILES: Cc1ccccc1C(=O)Nc1ccc(C(=O)N2CCC3OC(C)(C)OC3c3ccccc32)cc1]

;

the $C_{1-6}$ heteroalkyl or 5- to 6-membered heteroaryl comprises 1, 2, 3, or 4 heteroatoms or heteroatom groups independently selected from —O—, —NH—, —S—, —C(=O)—, —C(=O)O—, —S(=O)—, —$S(=O)_2$—, and N.

In another aspect of the present disclosure, the present disclosure also provides a compound of formula (II-1), (II-2), (II-3), or (II-4), an optical isomer thereof, or a pharmaceutically acceptable salt thereof, (II-1)

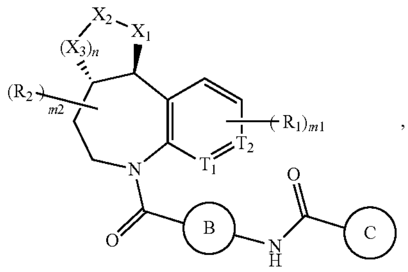

, (II-2)

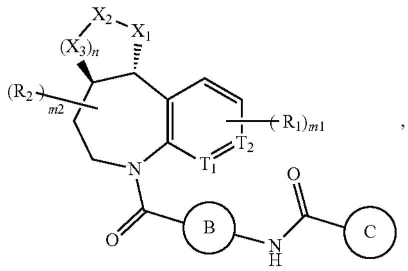

,

-continued (II-3)

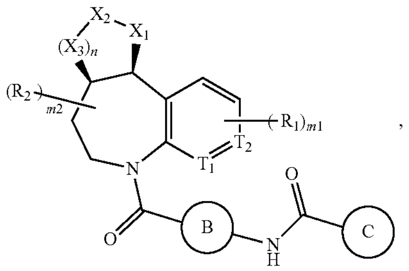

(II-4)

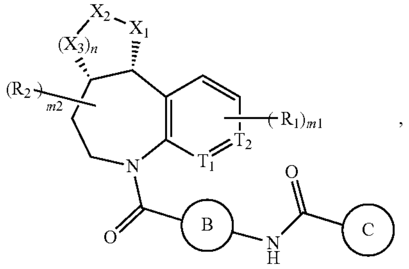

wherein ring B, ring C, $X_1$, $X_2$, $X_3$, $T_1$, $T_2$, $R_1$, $R_2$, m1, m2, n are as defined above.

In another aspect of the present disclosure, the present disclosure also provides a compound of formula (III), an optical isomer thereof, or a pharmaceutically acceptable salt thereof, (III)

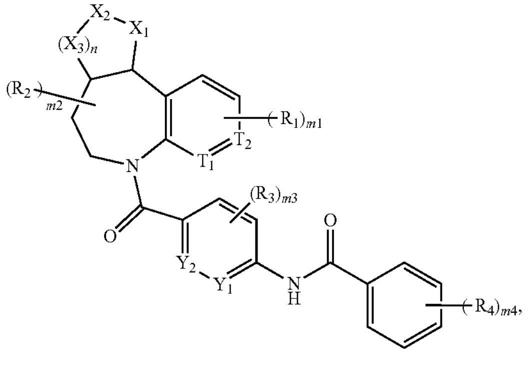

wherein $X_1$, $X_2$, $X_3$ are each independently selected from O, $C(R_A)_2$, and $NR_A$;

$T_1$, $T_2$ are each independently selected from N and $C(R_T)$;

$Y_1$, $Y_2$ are each independently selected from N and $C(R_Y)$;

$R_1$, $R_2$, $R_3$, $R_A$, $R_T$, $R_Y$ are each independently selected from H, F, Cl, Br, I, CN, OH, $NH_2$, $C_{1-6}$ alkyl, and $C_{1-6}$ heteroalkyl, and the $C_{1-6}$ alkyl or $C_{1-6}$ heteroalkyl is optionally substituted by 1, 2, or 3 R;

each $R_4$ is independently selected from H, F, Cl, Br, I, CN, OH, $NH_2$, $C_{1-6}$ alkyl, $C_{1-6}$ alkoxy, $C_{1-6}$ alkylamino, $C_{3-6}$ cycloalkyl, phenyl, and 5- to 6-membered heteroaryl, and the $C_{1-6}$ alkyl, $C_{1-6}$ alkoxy, $C_{1-6}$ alkylamino, $C_{3-6}$ cycloalkyl, phenyl, or 5- to 6-membered heteroaryl is optionally substituted by 1, 2, or 3 $R_{4a}$;

R, $R_{4a}$ are each independently selected from H, F, Cl, Br, I, CN, OH, $NH_2$, $C_{1-6}$ alkyl, $C_{1-6}$ alkoxy, and $C_{1-6}$ alkylamino, and the $C_{1-6}$ alkyl, $C_{1-6}$ alkoxy, and $C_{1-6}$ alkylamino are optionally substituted by 1, 2, or 3 R';

R' is selected from H, F, Cl, Br, I, CN, OH, $NH_2$, and $C_{1-6}$ alkyl;

m1, m2, m3, m4, n are each independently selected from 0, 1, or 2;

and when $X_1$, $X_3$ are selected from O at the same time, the compound of formula (III) is not selected from

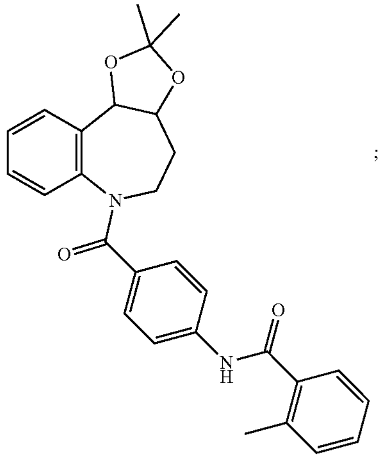 [SMILES: Cc1ccccc1C(=O)Nc1ccc(C(=O)N2CCC3OC(C)(C)OC3c3ccccc32)cc1]

;

the $C_{1-6}$ heteroalkyl or 5- to 6-membered heteroaryl comprises 1, 2, 3, or 4 heteroatoms or heteroatom groups independently selected from —O—, —NH—, —S—, —C(=O)—, —C(=O)O—, —S(=O)—, —S(=O)$_2$—, and N.

In another aspect of the present disclosure, the present disclosure also provides a compound of formula (III-1), (III-2), (III-3), or (III-4), an optical isomer thereof, or a pharmaceutically acceptable salt thereof, (III-1)

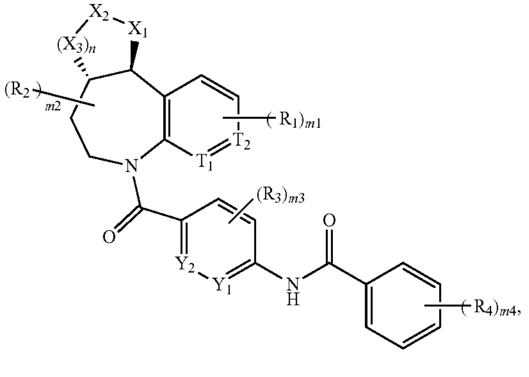

-continued (III-2)

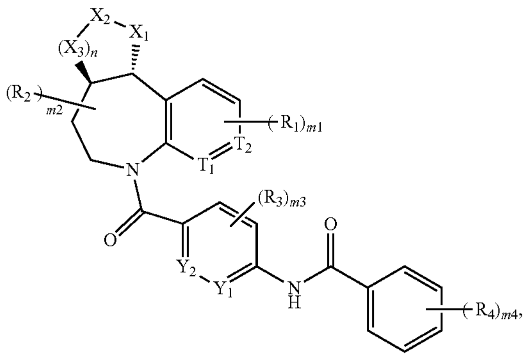

(III-3)

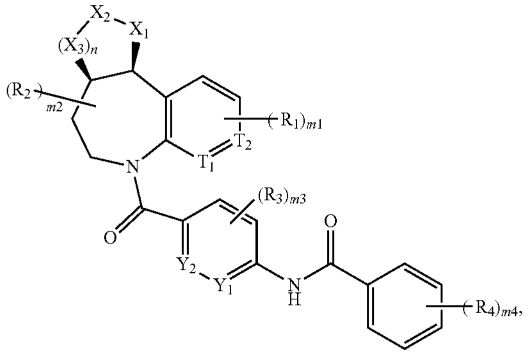

(III-4)

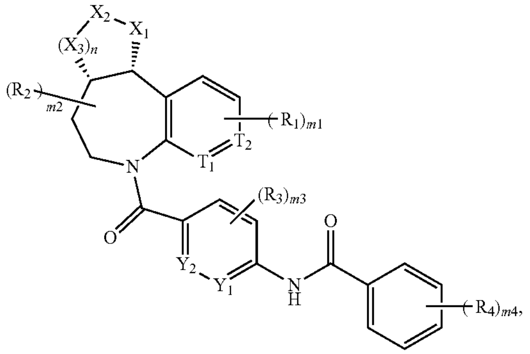

wherein $X_1$, $X_2$, $X_3$, $T_1$, $T_2$, $Y_1$, $Y_2$, $R_1$, $R_2$, $R_3$, $R_4$, m1, m2, m3, m4, n are as defined above.

In another aspect of the present disclosure, the present disclosure also provides a compound of formula (IV), an optical isomer thereof, or a pharmaceutically acceptable salt thereof, (IV)

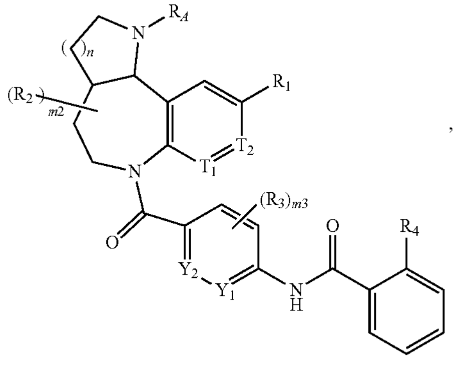

, wherein $T_1$, $T_2$ are each independently selected from O, N, and $C(R_T)$;

$Y_1$, $Y_2$ are each independently selected from N and $C(R_Y)$;

$R_1$, $R_2$, $R_3$, $R_A$, $R_T$, $R_Y$ are each independently selected from H, F, Cl, Br, I, CN, OH, $NH_2$, $C_{1-6}$ alkyl, and $C_{1-6}$ heteroalkyl, and the $C_{1-6}$ alkyl or $C_{1-6}$ heteroalkyl is optionally substituted by 1, 2, or 3 R;

each $R_4$ is independently selected from H, F, Cl, Br, I, CN, OH, $NH_2$, $C_{1-6}$ alkyl, $C_{1-6}$ alkoxy, $C_{1-6}$ alkylamino, $C_{3-6}$ cycloalkyl, phenyl, and 5- to 6-membered heteroaryl, and the $C_{1-6}$ alkyl, $C_{1-6}$ alkoxy, $C_{1-6}$ alkylamino, $C_{3-6}$ cycloalkyl, phenyl, or 5- to 6-membered heteroaryl is optionally substituted by 1, 2, or 3 $R_{4a}$;

R, $R_{4a}$ are each independently selected from H, F, Cl, Br, I, CN, OH, $NH_2$, $C_{1-6}$ alkyl, $C_{1-6}$ alkoxy, and $C_{1-6}$ alkylamino, and the $C_{1-6}$ alkyl, $C_{1-6}$ alkoxy, and $C_{1-6}$ alkylamino are optionally substituted by 1, 2, or 3 R';

R' is selected from H, F, Cl, Br, I, CN, OH, $NH_2$, and $C_{1-6}$ alkyl;

m2, m3, n are each independently selected from 0, 1, or 2;

the $C_{1-6}$ heteroalkyl or 5- to 6-membered heteroaryl comprises 1, 2, 3, or 4 heteroatoms or heteroatom groups independently selected from —O—, —NH—, —S—, —C(=O)—, —C(=O)O—, —S(=O)—, $—S(=O)_2—$, and N.

In another aspect of the present disclosure, the present disclosure also provides a compound of formula (V-1), (V-2), (V-3), or (V-4), an optical isomer thereof, or a pharmaceutically acceptable salt thereof, (V-1)

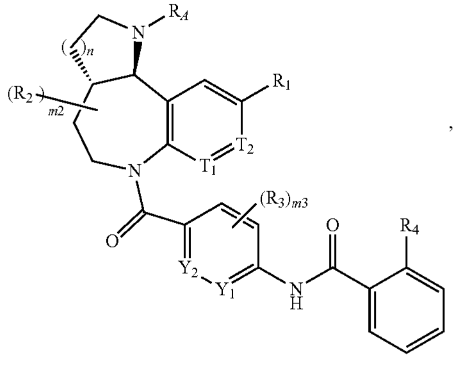

,

-continued (V-2)

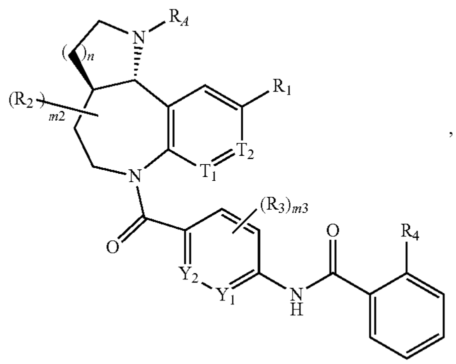

, (V-3)

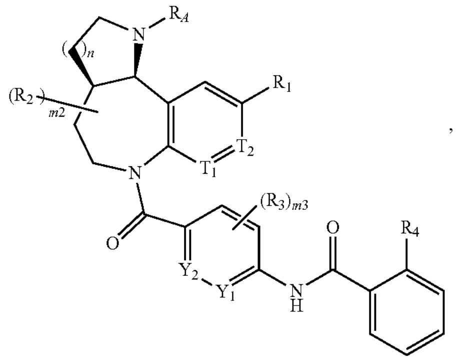

, (V-4)

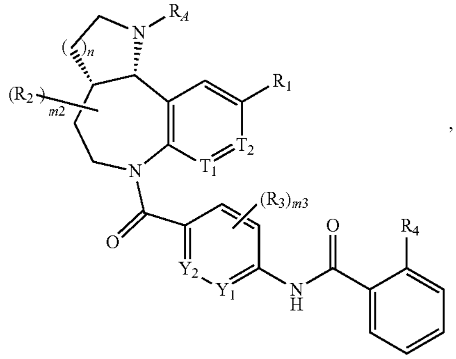

, wherein $T_1$, $T_2$, $Y_1$, $Y_2$, $R_1$, $R_2$, $R_3$, $R_4$, $R_A$, m2, m3, n are as defined above.

In some embodiments of the present disclosure, the $R_4$ is selected from H, F, Cl, Br, I, CN, OH, $NH_2$, $CH_3$, $CF_3$,

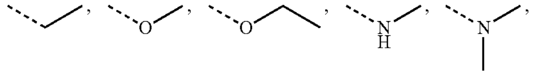

cyclopropyl, cyclobutyl, cyclopentyl, phenyl, pyridyl, pyrimidinyl, thienyl, and thiazolyl, and other variables are as defined in the present disclosure.

In some embodiments of the present disclosure, the ring A is selected from azetidinyl, oxetanyl, pyrrolidinyl, tetrahydrofuranyl, cyclobutyl, cyclopentyl, and cyclohexyl, and the azetidinyl, oxetanyl, pyrrolidinyl, tetrahydrofuranyl, cyclobutyl, cyclopentyl, or cyclohexyl is optionally substituted by 1 or 2 $R_A$, and other variables are as defined in the present disclosure.

In some embodiments of the present disclosure, the ring A is selected from

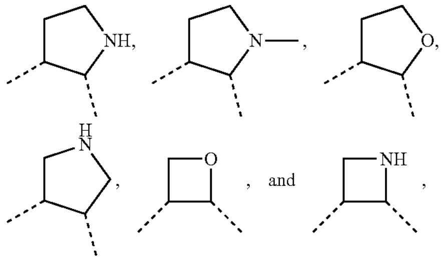

and other variables are as defined in the present disclosure.

In some embodiments of the present disclosure, the ring B is selected from phenyl and pyridyl, and the phenyl or pyridyl is optionally substituted by 1, 2, or 3 $R_3$, and other variables are as defined in the present disclosure.

In some embodiments of the present disclosure, the ring B is selected from

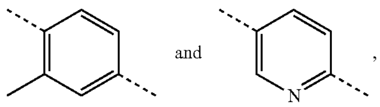

and other variables are as defined in the present disclosure.

In some embodiments of the present disclosure, the ring C is selected from

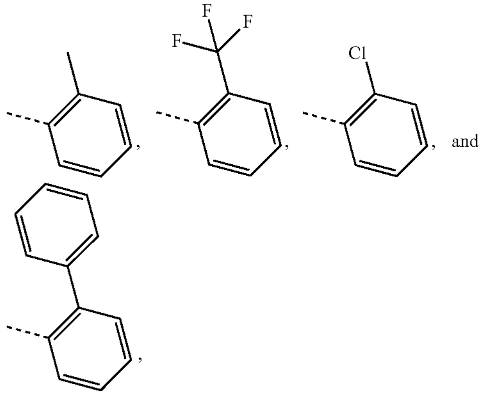

and other variables are as defined in the present disclosure.

In yet another aspect of the present disclosure, the present disclosure also provides a compound of the following formula, an optical isomer thereof, or a pharmaceutically acceptable salt thereof, selected from

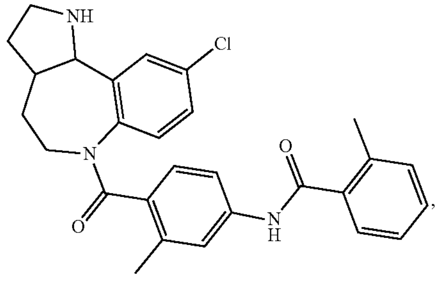

-continued
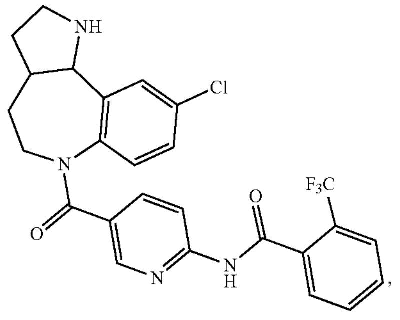
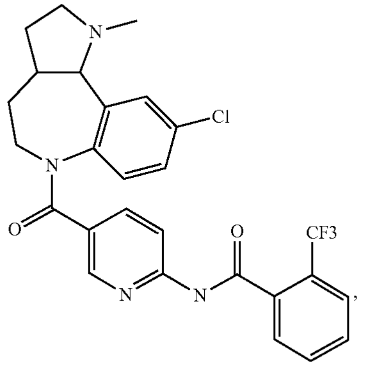
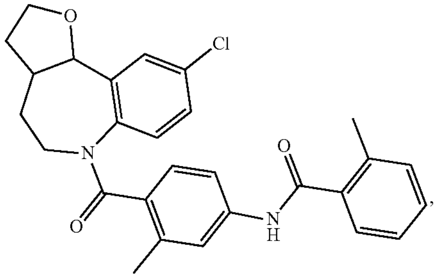
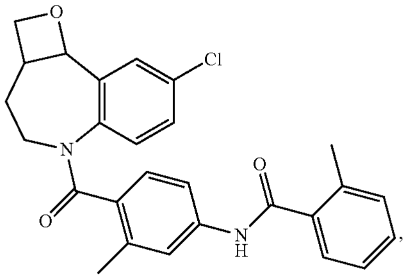
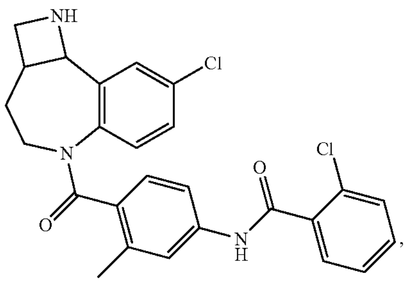
-continued
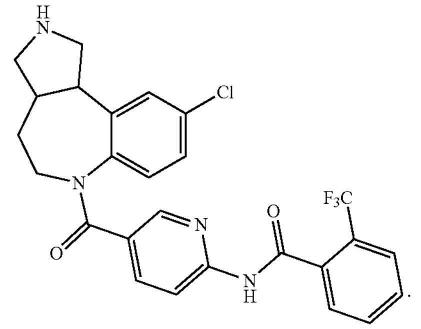
In yet another aspect of the present disclosure, the present disclosure also provides a compound of the following formula, an optical isomer thereof, or a pharmaceutically acceptable salt thereof, selected from
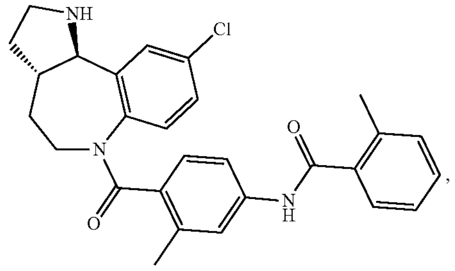
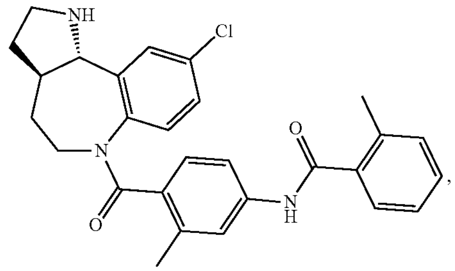
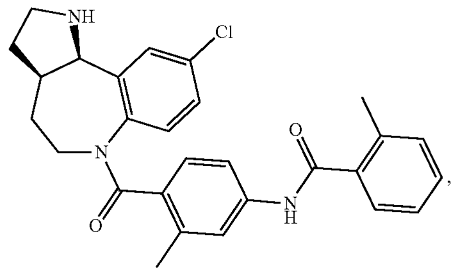
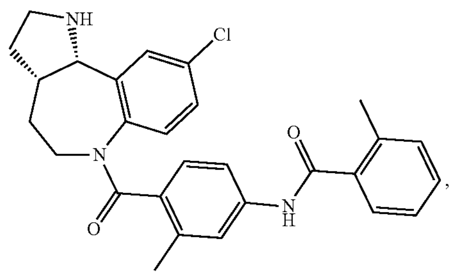

-continued
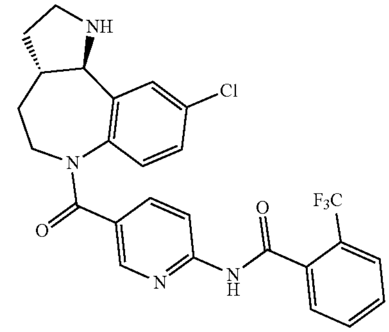
,
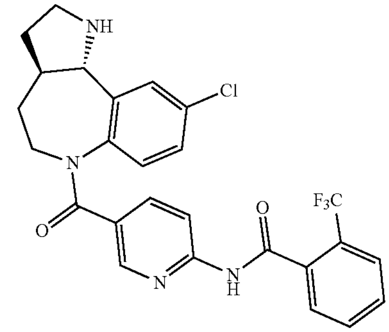
,
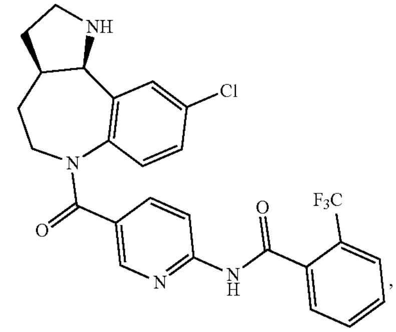
,
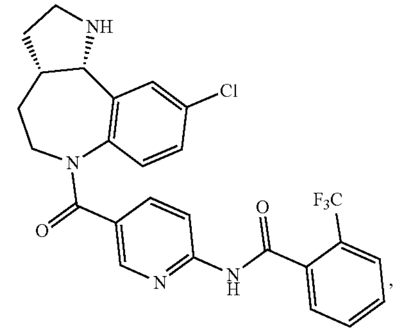
,
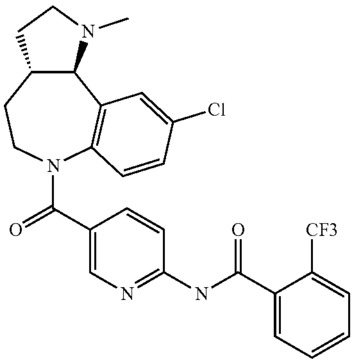
,
-continued
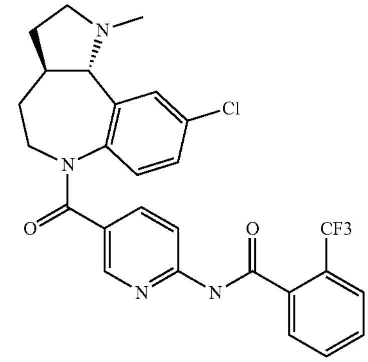
,
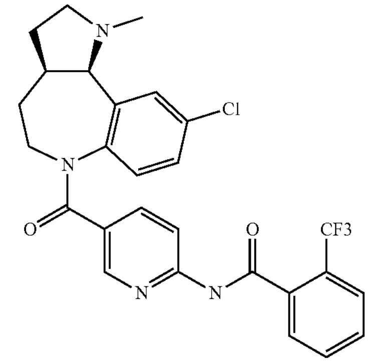
,
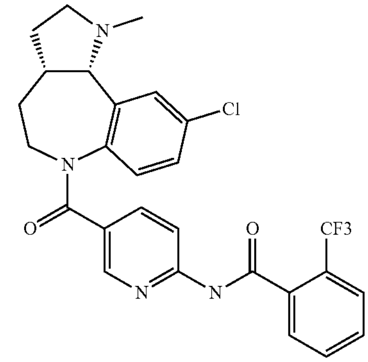
,
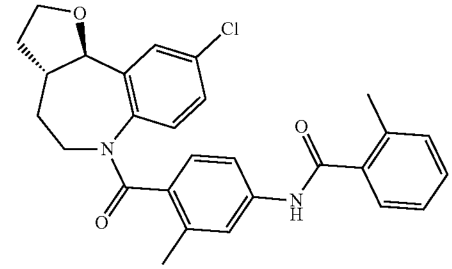
,
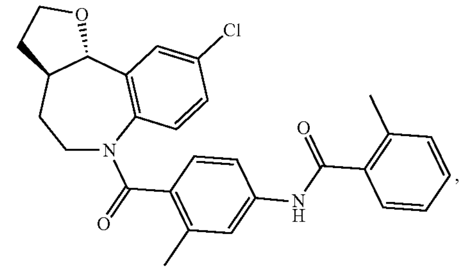
, -continued
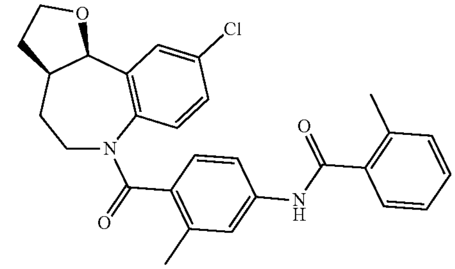
,
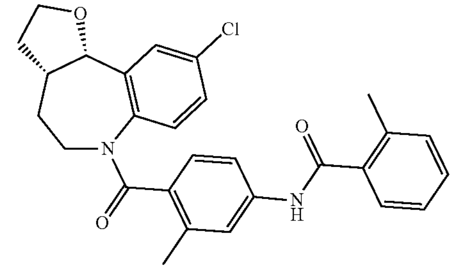
,
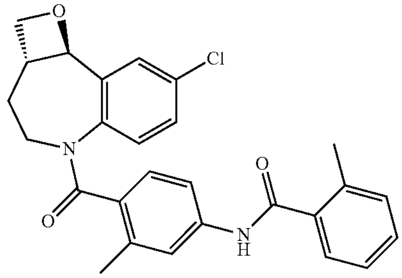
,
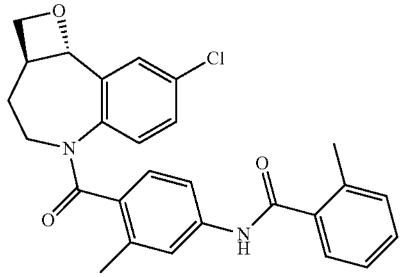
,
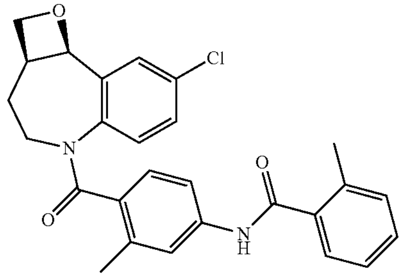
,
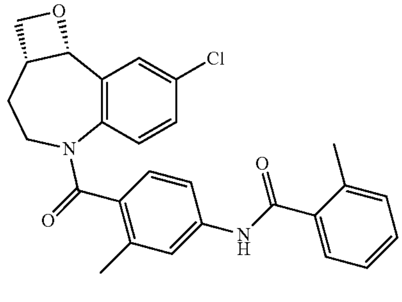
,
-continued
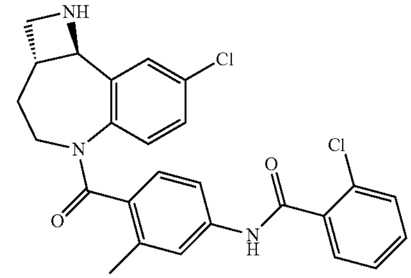
,
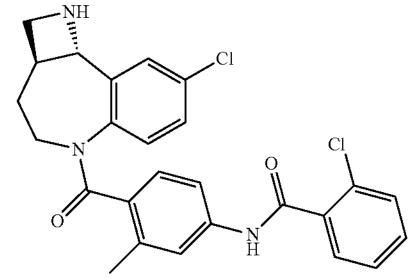
,
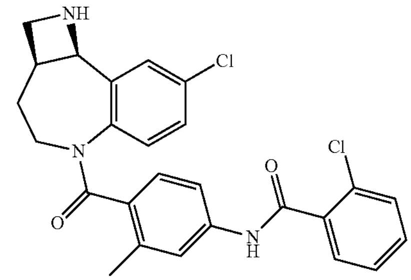
,
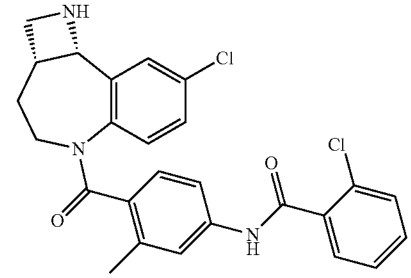
,
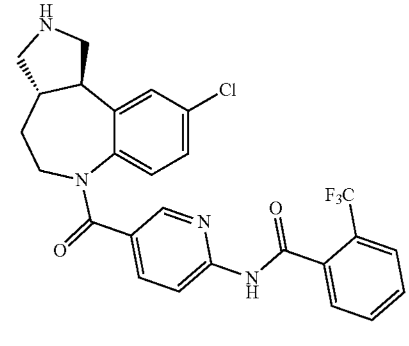
, -continued

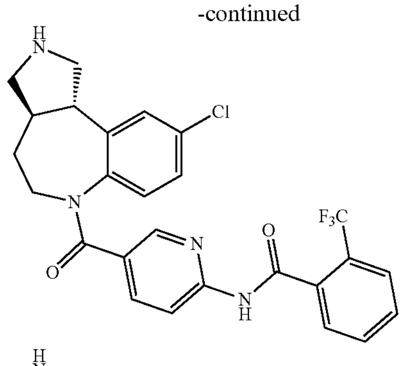

,

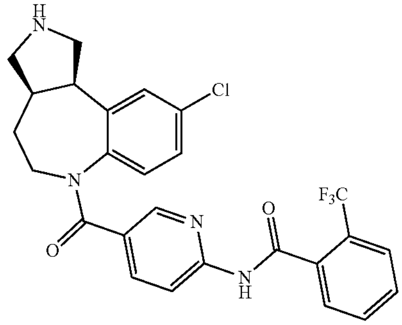

,

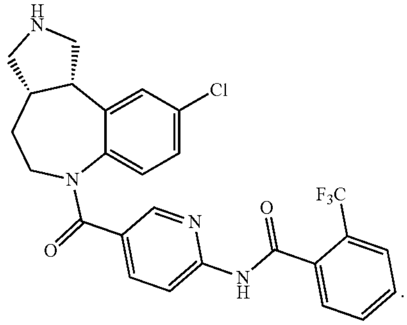

.

In yet another aspect of the present disclosure, the present disclosure also provides a use of the compound, the optical isomer thereof, or the pharmaceutically acceptable salt thereof in the manufacture of a medicament for the prevention or treatment of diseases related to arginine vasopressin V1a receptor, arginine vasopressin V1b receptor, arginine vasopressin V2 receptor, sympathetic nervous system, or renin-angiotensin-aldosterone system.

In some embodiments of the present disclosure, the diseases related to arginine vasopressin V1a receptor, arginine vasopressin V1b receptor, arginine vasopressin V2 receptor, sympathetic nervous system, or renin-angiotensin-aldosterone system comprise: hypertension, Reye's syndrome, dysmenorrhea, premature delivery, corticotropin-releasing hormone secretion disorder, adrenal hyperplasia, depression, chronic congestive heart failure, liver cirrhosis, syndrome of inappropriate antidiuretic hormone secretion, hyponatremia caused by chronic heart failure/liver cirrhosis/inappropriate antidiuretic hormone secretion, or polycystic kidney disease.

The present disclosure has at least one of the following technical effects:

1) Compared with the prior art (such as the positive drug Tolvaptan), the compounds of the present disclosure have lower liver toxicity, and the specific performance includes but not limited to: the compounds of the present disclosure can reduce the inhibition of bile excretion into the bile duct, do not capture GSH (glutathione) and/or do not produce DM4103-like metabolites;
2) compared with the prior art, the proportional dose-effect of the compounds of the present disclosure has no hook effect in AVP-induced LLC-PK1 cell proliferation, so the compounds of the present disclosure have a better curative effect;
3) compared with the prior art (such as the positive drug Lixivaptan), the compounds of the present disclosure do not inhibit CYP;
4) compared with the prior art, the compounds of the present disclosure have a longer half-life, thus prolonging the drug effect;
5) compared with the prior art, the compounds of the present disclosure have high selectivity for V2 receptor.

DEFINITION AND DESCRIPTION

Unless otherwise specified, the following terms and phrases used herein are intended to have the following meanings. A specific phrase or term should not be considered indefinite or unclear in the absence of a particular definition but should be understood according to the common meaning. When a trading name appears herein, it is intended to refer to its corresponding commercial product or active ingredient thereof.

As used herein, the phrase "at least one" when referring to a list of one or more than one element should be understood to mean at least one element selected from any one or more elements in the list of elements, but not necessarily including at least one of each element specified in the list of elements, and not excluding any combination of elements in the list of elements. This definition also allows that elements may optionally be present other than the elements specifically identified within the list of elements to which the phrase "at least one" refers, whether related or unrelated to those elements specifically identified.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, an allergic reaction, other problems, or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine, magnesium, or similar salts. When the compound of the present disclosure contains a relatively basic functional group, an acid addition salt can be obtained by bringing the neutral form of the compound into contact with a sufficient amount of acid in a solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid; and an organic acid salt, wherein the organic acid includes, for example, acetic acid, propionic acid, isobutyric acid, trifluoroacetic acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid; and salts of amino acid (such as arginine), and a salt of an organic acid such as glucuronic acid. Certain specific compounds of the present disclosure contain both basic and acidic functional groups, thus can be converted to any base or acid addition salt.

The pharmaceutically acceptable salt of the present disclosure can be prepared from the parent compound that contains an acidic or basic moiety by a conventional chemical method. Generally, such salt can be prepared by reacting the free acid or base form of the compound with a stoichiometric amount of an appropriate base or acid in water or an organic solvent or a mixture thereof.

The compounds of the present disclosure may exist in specific geometric or stereoisomeric forms. The present disclosure contemplates all such compounds, including cis and trans isomers, (−)- and (+)-enantiomers, (R)- and (S)-enantiomers, diastereomers, (D)-isomers, (L)-isomers, racemic mixtures, and other mixtures thereof, such as enantiomers or diastereomeric enriched mixtures, all of which are within the scope of the present disclosure. Additional asymmetric carbon atoms may be present in substituents such as alkyl. All these isomers and their mixtures are included within the scope of the present disclosure.

Unless otherwise specified, the absolute configuration of a stereogenic center is represented by a wedged solid bond ( ) and a wedged dashed bond ( ), and the relative configuration of a stereogenic center is represented by a straight solid bond ( ) and a straight dashed bond ( ). For example, the straight solid bond and the dashed bond at the C1 and C2 atoms in

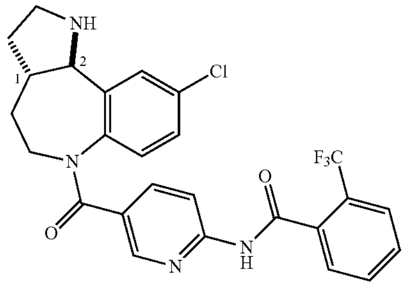

indicate that the two bonds linked to C1 and C2 are facing inward and outward, respectively, i.e., representing two trans-configuration compounds,

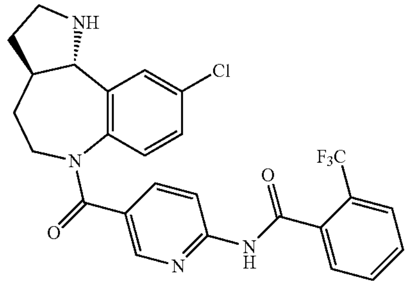

or

-continued

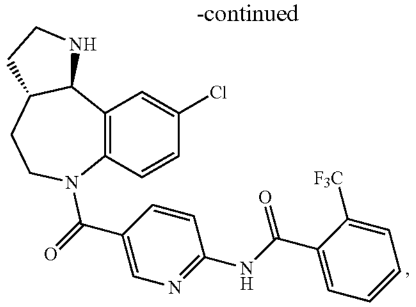

, and if the compound is in a cis structure, it can be represented by two straight solid bonds ( ) or two straight dashed bonds ( ), i.e.,

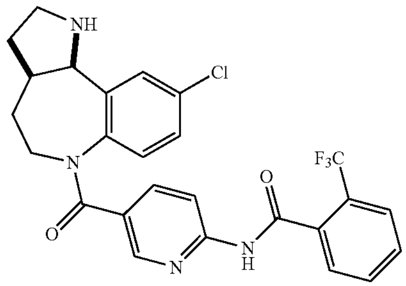

and

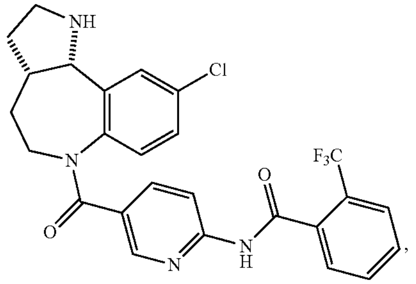

, which both represent

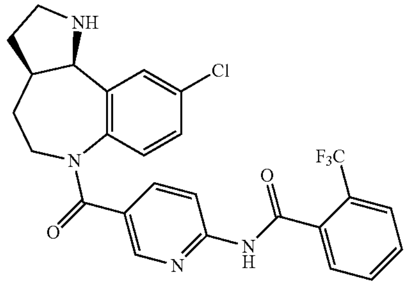

or

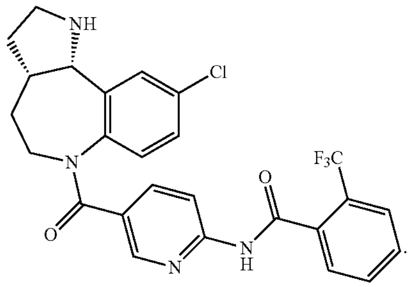

.

The compounds of the present disclosure may exist in particular. Unless otherwise specified, the term “tautomer” or “tautomeric form” means that at room temperature, the isomers of different functional groups are in dynamic equilibrium and can be transformed into each other quickly. If tautomers possibly exist (such as in solution), the chemical equilibrium of tautomers can be reached. For example, proton tautomer (also called prototropic tautomer) includes interconversion through proton migration, such as keto-enol isomerization and imine-enamine isomerization. Valence tautomer includes some recombination of bonding electrons for mutual transformation. A specific example of keto-enol tautomerization is the tautomerism between two tautomers of pentane-2,4-dione and 4-hydroxypent-3-en-2-one.

The compound of the present disclosure may contain an unnatural proportion of atomic isotope at one or more than one atom that constitutes the compound. For example, the compound can be labeled with a radioactive isotope, such as tritium ($^3H$), iodine-125 ($^{125}I$), or C-14 ($^{14}C$). For another example, deuterated drugs can be formed by replacing hydrogen with deuterium, the bond formed by deuterium and carbon is stronger than that of ordinary hydrogen and carbon, compared with non-deuterated drugs, deuterated drugs have the advantages of reduced toxic and side effects, increased drug stability, enhanced efficacy, extended biological half-life of drugs, etc. All isotopic variations of the compound of the present disclosure, whether radioactive or not, are encompassed within the scope of the present disclosure. “Optional” or “optionally” means that the subsequent event or condition may occur but not requisite, and the description includes the instance in which the event or condition occurs and the instance in which the event or condition does not occur.

When the valence bond of a group has a dashed line “ ”, such as in

“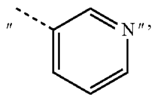”, the dashed line indicates the linkage site of the group to the rest of the molecule. When there is “ ” on a single bond, for example, in “ ”, the dashed line represents a single bond or absent, and also means that “ ” represents a single bond “ ” or a double bond “ ”.

The term “substituted” or “substituted by . . . ” means one or more hydrogen atoms on a specific atom are substituted by the substituent, including deuterium and hydrogen variables, as long as the valence of the specific atom is normal and the substituted compound is stable. The term “optionally substituted” or “optionally substituted by . . . ” means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted by 1, 2, or 3 R', the group can be optionally substituted by 1, 2, or 3 R', wherein the definition of R' at each occurrence is independent. Moreover, a combination of the substituent and/or the variant thereof is allowed only when the combination results in a stable compound.

When one of the variables is selected from a single bond, it means that the two groups linked by the single bond are linked directly. For example, when $L_1$ in

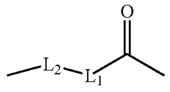

represents a single bond, the structure is actually

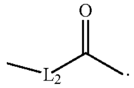.

When the listed substituents do not indicate via which atom it is linked to the substituted group, this substituent can be bonded via any atom, for example, pyridyl, as a substituent, can link to the substituted group via any carbon atom on the pyridine ring.

When the listed linking group does not indicate the direction for linking, the direction for linking is arbitrary, for example, the linking group L contained in

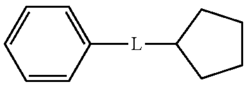

is —$CH_2O$—, then —$CH_2O$— can link phenyl and cyclopentyl to form

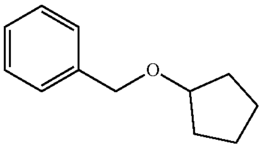 [SMILES: c1ccc(COC2CCCC2)cc1]

in the direction same as left-to-right reading order, and can link phenyl and cyclopentyl to form

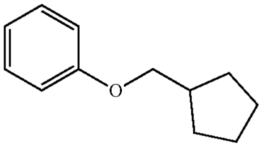 [SMILES: c1ccc(OCC2CCCC2)cc1]

in the direction contrary to left-to-right reading order. A combination of the linking groups, substituents and/or variables thereof is allowed only when such combination can result in a stable compound.

Unless otherwise specified, the number of atoms on a ring is usually defined as the number of membered rings, such as a “3- to 6-membered ring” is a “ring” with 3 to 6 atoms arranged around it.

Unless otherwise specified, the term “$C_{1-6}$ alkyl” refers to a linear or branched saturated hydrocarbon group consisting of 1 to 6 carbon atoms. The $C_{1-6}$ alkyl includes $C_{1-5}$ alkyl, $C_{1-4}$ alkyl, $C_{1-3}$ alkyl, $C_{1-2}$ alkyl, $C_{2-6}$ alkyl, $C_{2-4}$ alkyl, $C_6$ alkyl, $C_5$ alkyl, etc.; it can be monovalent (such as $CH_3$), divalent ($—CH_2—$), or multivalent (such as

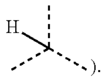
).

Examples of $C_{1-6}$ alkyl include, but are not limited to, $CH_3$

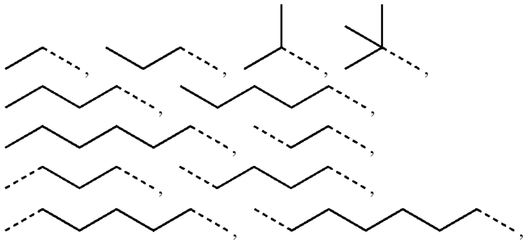

etc.

Unless otherwise specified, the term "$C_{1-4}$ alkyl" refers to a linear or branched saturated hydrocarbon group consisting of 1 to 4 carbon atoms. The $C_{1-4}$ alkyl includes $C_{1-2}$ alkyl, $C_{1-3}$ alkyl, $C_{3-4}$ alkyl, $C_{2-3}$ alkyl, etc.; it can be monovalent (such as $CH_3$), divalent ($—CH_2—$), or multivalent (such as

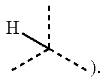
).

Examples of $C_{1-4}$ alkenyl include, but are not limited to, $CH_3$,

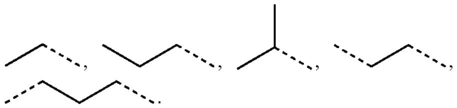

Unless otherwise specified, "$C_{2-3}$ alkenyl" refers to a linear or branched hydrocarbon group consisting of 2 to 3 carbon atoms containing at least one carbon-carbon double bond, and the carbon-carbon double bond may be located at any position of the group. The $C_{2-3}$ alkenyl includes $C_3$ alkenyl and $C_2$ alkenyl; it can be monovalent, divalent, or multivalent. Examples of $C_{2-3}$ alkenyl include, but are not limited to,

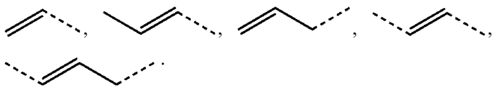

Unless otherwise specified, "$C_{2-3}$ alkynyl" refers to a linear or branched hydrocarbon group consisting of 2 to 3 carbon atoms containing at least one carbon-carbon triple bond, and the carbon-carbon triple bond may be located at any position of the group. It can be monovalent, divalent, or multivalent. The $C_{2-3}$ alkynyl includes $C_3$ alkynyl and $C_2$ alkynyl. Examples of $C_{2-3}$ alkynyl include, but are not limited to,

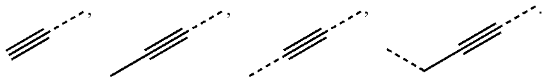

The term "heteroalkyl" by itself or in combination with another term means a stable linear or branched alkyl group or a combination thereof consisting of a certain number of carbon atoms, and at least one heteroatom or heteroatom group. In some embodiments, the heteroatom is selected from B, O, N, and S, wherein the nitrogen and sulfur atoms are optionally oxidized, and the nitrogen heteroatom is optionally quaternized. In other embodiments, the heteroatom group is selected from $—C(=O)O—$, $—C(=O)—$, $—C(=S)—$, $—S(=O)$, $—S(=O)_2—$, $—C(=O)N(H)—$, $—N(H)—$, $—C(=NH)—$, $—S(=O)_2N(H)—$, and $—S(=O)N(H)—$. In some embodiments, the heteroalkyl is $C_{1-6}$ heteroalkyl; in other embodiments, the heteroalkyl is $C_{1-3}$ heteroalkyl. A heteroatom or heteroatom group may be located at any internal position within a heteroalkyl, including the site where the alkyl group is linked to the rest of the molecule, but the term "alkoxy" is a conventional expression referring to those alkyl groups linked to the rest of the molecule through an oxygen atom. Examples of heteroalkyl include, but are not limited to, $—OCH_3$, $—OCH_2CH_3$, $—OCH_2CH_2CH_3$, $—OCH_2(CH_3)_2$, $—CH_2—CH_2—O—CH_3$, $—NHCH_3$, $—N(CH_3)_2$, $—NHCH_2CH_3$, $—N(CH_3)(CH_2CH_3)$, $—CH_2—CH_2—NH—CH_3$, $—CH_2—CH_2—N(CH_3)—CH_3$, $—SCH_3$, $—SCH_2CH_3$, $—SCH_2CH_2CH_3$, $—SCH_2(CH_3)_2$, $—CH_2—S—CH_2—CH_3$, $—CH_2—CH_2$, $—S(=O)—CH_3$, $—CH_2—CH_2—S(=O)_2—CH_3$, and up to two heteroatoms may be consecutive, e.g., $—CH_2—NH—OCH_3$.

Unless otherwise specified, the term "$C_{1-6}$ alkoxy" refers to an alkyl group containing 1 to 6 carbon atoms that are connected to the rest of the molecule through an oxygen atom. The $C_{1-6}$ alkoxy includes $C_{1-4}$ alkoxy, $C_{1-3}$ alkoxy, $C_{1-2}$ alkoxy, $C_{2-6}$ alkoxy, $C_{2-4}$ alkoxy, $C_6$ alkoxy, $C_5$ alkoxy, $C_4$ alkoxy, $C_3$ alkoxy, etc. Examples of $C_{1-6}$ alkoxy include, but are not limited to, methoxy, ethoxy, propoxy (including n-propoxy and isopropoxy), butoxy (including n-butoxy, isobutoxy, s-butoxy, and t-butoxy), pentyloxy (including n-pentyloxy, isopentyloxy, and neopentyloxy), hexyloxy, etc.

Unless otherwise specified, the term "$C_{1-3}$ alkoxy" refers to an alkyl group containing 1 to 3 carbon atoms that are connected to the rest of the molecule through an oxygen atom. The $C_{1-3}$ alkoxy includes $C_{1-3}$ alkoxy, $C_{1-2}$ alkoxy, $C_{2-3}$ alkoxy, $C_1$ alkoxy, $C_2$ alkoxy, $C_3$ alkoxy, etc. Examples of $C_{1-3}$ alkoxy include, but are not limited to, methoxy, ethoxy, propoxy (including n-propoxy and isopropoxy), etc.

Unless otherwise specified, the term "$C_{1-6}$ alkylamino" refers to an alkyl group containing 1 to 6 carbon atoms that are connected to the rest of the molecule through an amino group. The $C_{1-6}$ alkylamino includes $C_{1-4}$ alkylamino, $C_{1-3}$ alkylamino, $C_{1-2}$ alkylamino, $C_{2-6}$ alkylamino, $C_{2-4}$ alkylamino, $C_6$ alkylamino, $C_5$ alkylamino, $C_4$ alkylamino, $C_3$ alkylamino, $C_2$ alkylamino, etc. Examples of $C_{1-6}$ alkylamino include, but are not limited to, $—NHCH_3$, $—N(CH_3)_2$, $—NHCH_2CH_3$, $—N(CH_3)CH_2CH_3$, $—N(CH_2CH_3)(CH_2CH_3)$, $—NHCH_2CH_2CH_3$, $—NHCH_2(CH_3)_2$, $—NHCH_2CH_2CH_2CH_3$, etc.

Unless otherwise specified, the term "$C_{1-3}$ alkylamino" refers to an alkyl group containing 1 to 3 carbon atoms that are connected to the rest of the molecule through an amino group. The $C_{1-3}$ alkylamino includes $C_{1-3}$ alkylamino, $C_{1-2}$ alkylamino, $C_{2-3}$ alkylamino, $C_1$ alkylamino, $C_2$ alkylamino, $C_3$ alkylamino, etc. Examples of $C_{1-3}$ alkylamino include, but are not limited to, —$NHCH_3$, —$N(CH_3)_2$, —$NHCH_2CH_3$, —$N(CH_3)CH_2CH_3$, —$NHCH_2CH_2CH_3$, —$NHCH_2(CH_3)_2$ , etc.

Unless otherwise specified, the term "$C_{1-6}$ alkylthio" refers to an alkyl group containing 1 to 6 carbon atoms that are connected to the rest of the molecule through a sulfur atom. The $C_{1-6}$ alkylthio includes $C_{1-4}$ alkylthio, $C_{1-3}$ alkylthio, $C_{1-2}$ alkylthio, $C_{2-6}$ alkylthio, $C_{2-4}$ alkylthio, $C_6$ alkylthio, $C_5$ alkylthio, $C_4$ alkylthio, $C_3$ alkylthio, $C_2$ alkylthio, etc. Examples of $C_{1-6}$ alkylthio include, but are not limited to, —$SCH_3$, —$SCH_2CH_3$, —$SCH_2CH_2CH_3$, —$SCH_2(CH_3)_2$ , etc.

Unless otherwise specified, the term "$C_{1-3}$ alkylthio" refers to an alkyl group containing 1 to 3 carbon atoms that are connected to the rest of the molecule through a sulfur atom. The $C_{1-3}$ alkylthio includes $C_{1-3}$ alkylthio, $C_{1-2}$ alkylthio, $C_{2-3}$ alkylthio, $C_1$ alkylthio, $C_2$ alkylthio, $C_3$ alkylthio, etc. Examples of $C_{1-3}$ alkylthio include, but are not limited to, —$SCH_3$, —$SCH_2CH_3$, —$SCH_2CH_2CH_3$, —$SCH_2(CH_3)_2$, etc.

Unless otherwise specified, "$C_{4-6}$ cycloalkyl" refers to a saturated cyclic hydrocarbon group consisting of 4 to 6 carbon atoms in monocyclic and bicyclic systems, and the $C_{4-6}$ cycloalkyl includes $C_{4-5}$ cycloalkyl, $C_{5-6}$ cycloalkyl, $C_4$ cycloalkyl, $C_5$ cycloalkyl, etc.; it can be monovalent, divalent, or multivalent. Examples of $C_{4-6}$ cycloalkyl include, but are not limited to, cyclobutyl, cyclopentyl, cyclohexyl, etc.

Unless otherwise specified, the term "4- to 6-membered heterocyclyl" by itself or in combination with other terms refers to a saturated cyclic group consisting of 4 to 6 ring atoms, respectively, wherein 1, 2, 3, or 4 ring atoms are heteroatoms independently selected from O, S, and N and the rest are carbon atoms, wherein the nitrogen atoms are optionally quaternized, and the nitrogen and sulfur heteroatoms are optionally oxidized (i.e., NO and $S(O)_p$, p is 1 or 2). It includes monocyclic and bicyclic systems, wherein the bicyclic system includes spiro rings, fused rings, and bridged rings. In addition, in the case of the "4- to 6-membered heterocycloalkyl", the heteroatom may occupy the position where the heterocycloalkyl is linked to the rest of the molecule. The 4- to 6-membered heterocycloalkyl includes 4- to 5-membered heterocycloalkyl, 4-membered heterocycloalkyl, 5-membered heterocycloalkyl, 5- to 6-membered heterocycloalkyl, 6-membered heterocycloalkyl, etc. Examples of 4- to 6-membered heterocyclyl include, but are not limited to, azetidinyl, oxetanyl, thietanyl, pyrrolidinyl, pyrazolidinyl, imidazolidinyl, tetrahydrothiophenyl (including tetrahydrothiophen-2-yl, tetrahydrothiophen-3-yl, etc.), tetrahydrofuranyl (including tetrahydrofuran-2-yl, etc.), tetrahydropyranyl, piperidinyl (including 1-piperidinyl, 2-piperidinyl, 3-piperidinyl, etc.), piperazinyl (including 1-piperazinyl, 2-piperazinyl, etc.), morpholinyl (including 3-morpholinyl, 4-morpholinyl, etc.), dioxolyl, dithianyl, isoxazolidinyl, isothiazolidinyl, 1,2-oxazinyl, 1,2-thiazinyl, hexahydropyridazinyl, homopiperazinyl, homopiperidinyl, etc.

Unless otherwise specified, the terms "5- to 6-membered heteroaromatic ring" and "5- to 6-membered heteroaryl" in the present disclosure may be used interchangeably, and the term "5- to 6-membered heteroaryl" refers to a monocyclic group consisting of 5 to 6 ring atoms with conjugated π electronic system, wherein 1, 2, 3, or 4 ring atoms are heteroatoms independently selected from O, S, and N, and the rest are carbon atoms. Where the nitrogen atom is optionally quaternized, and the nitrogen and sulfur heteroatoms are optionally oxidized (i.e., NO and $S(O)_p$, p is 1 or 2). The 5- to 6-membered heteroaryl may be attached to the rest of the molecule through a heteroatom or a carbon atom. The 5- to 6-membered heteroaryl includes 5-membered and 6-membered heteroaryl. Examples of the 5- to 6-membered heteroaryl include, but are not limited to, pyrrolyl (including N-pyrrolyl, 2-pyrrolyl, 3-pyrrolyl, etc.), pyrazolyl (including 2-pyrazolyl, 3-pyrazolyl, etc.), imidazolyl (including N-imidazolyl, 2-imidazolyl, 4-imidazolyl, 5-imidazolyl, etc.), oxazolyl (including 2-oxazolyl, 4-oxazolyl, 5-oxazolyl, etc.), triazolyl (1H-1,2,3-triazolyl, 2H-1,2,3-triazolyl, 1H-1,2,4-triazolyl, 4H-1,2,4-triazolyl, etc.), tetrazolyl, isoxazolyl (3-isoxazolyl, 4-isoxazolyl, 5-isoxazolyl, etc.), thiazolyl (including 2-thiazolyl, 4-thiazolyl, 5-thiazolyl, etc.), furanyl (including 2-furanyl, 3-furanyl, etc.), thienyl (including 2-thienyl, 3-thienyl, etc.), pyridinyl (including 2-pyridyl, 3-pyridyl, 4-pyridyl, etc.), pyrazinyl, or pyrimidinyl (including 2 -pyrimidinyl, 4-pyrimidinyl, etc.).

Unless otherwise specified, $C_{n-n+m}$ or $C_n$-$C_{n+m}$ includes any specific instance of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$, also includes any range from n to n+m, for example, $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, $C_{9-12}$, etc.; similarly, n-membered to n+m-membered means that the number of atoms on the ring is from n to n+m, for example, 3- to 12-membered ring includes 3-membered ring, 4-membered ring, 5-membered ring, 6-membered ring, 7-membered ring, 8-membered ring, 9-membered ring, 10-membered ring, 11-membered ring, and 12-membered ring, also includes any range from n to n+m, such as 3- to 12-membered ring includes 3- to 6-membered ring, 3- to 9-membered ring, 5- to 6-membered ring, 5- to 7-membered ring, 5- to 10-membered ring, 6- to 7-membered ring, 6- to 8-membered ring, 6- to 9-membered ring, and 6- to 10-membered ring.

The term "leaving group" refers to a functional group or atom which can be replaced by another functional group or atom through a substitution reaction (such as nucleophilic substitution reaction). For example, representative leaving groups include triflate; chlorine, bromine, and iodine; sulfonate group, such as mesylate, tosylate, p-bromobenzenesulfonate, p-toluenesulfonate; acyloxy, such as acetoxy, trifluoroacetoxy.

The term "protecting group" includes, but is not limited to, "amino protecting group", "hydroxyl protecting group", or "mercapto protecting group". The term "amino protecting group" refers to a protecting group suitable for preventing the side reactions occurring at the nitrogen of an amino. Representative amino protecting groups include, but are not limited to: formyl; acyl, such as alkanoyl (e.g., acetyl, trichloroacetyl, or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl, such as benzyl (Bn), trityl (Tr), 1,1-bis-(4'-methoxyphenyl)methyl; silyl, such as trimethylsilyl (TMS) and tert-butyldimethylsilyl (TBS). The term "hydroxyl protecting group" refers to a protecting group suitable for preventing the side reactions of hydroxyl. Representative hydroxyl protecting groups include, but are not limited to: alkyl, such as methyl, ethyl, and tert-butyl; acyl, such as alkanoyl (e.g., acetyl); arylmethyl, such as benzyl (Bn), p-methoxybenzyl (PMB), 9-fluorenylmethyl (Fm), and diphenylmethyl (benzhydryl, DPM); silyl, such as trimethylsilyl (TMS) and tert-butyldimethylsilyl (TBS).

The compounds of the present disclosure can be prepared by a variety of synthetic methods known to those skilled in the art, including the specific embodiments listed below, the embodiments formed by their combination with other chemical synthesis methods, and equivalent alternatives known to those skilled in the art, preferred embodiments include but are not limited to the examples of the present disclosure.

The solvent used in the present disclosure is commercially available.

The compounds of the present disclosure are named according to the conventional naming principles in the art or by ChemDraw® software, and the commercially available compounds use the supplier catalog names.

DETAILED DESCRIPTION OF THE PREFERRED EMBODIMENT

Figure 1:
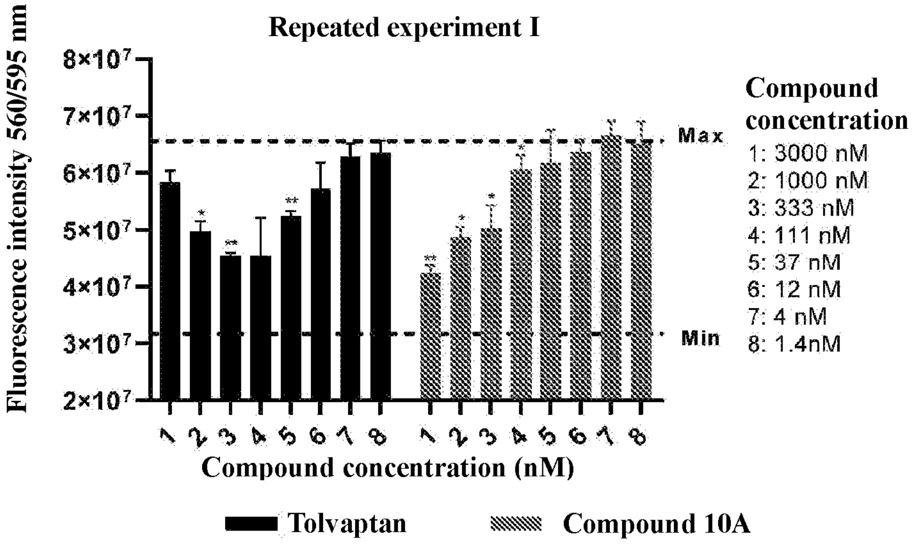
FIG. 1 is a graph of repeated experiment I according to an example of the present disclosure.

The present disclosure is described in detail by the examples below, but it does not mean that there are any adverse restrictions on the present disclosure. The present disclosure has been described in detail herein, and its specific embodiments have also been disclosed; for one skilled in the art, it is obvious to make various modifications and improvements to the embodiments of the present disclosure without departing from the spirit and scope of the present disclosure.

The experimental materials and reagents used in the following examples can be obtained from commercially available sources unless otherwise specified.

Preparation of Intermediates

Reference Example 1: Preparation of Intermediate I-1

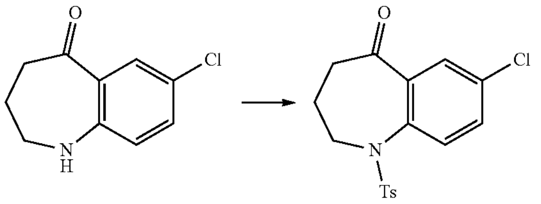

I-1

To a solution of 7-chloro-1,2,3,4-tetrahydrobenzo[B]azepin-5-one (15 g, 76.7 mmol) in pyridine (150 mL) was added p-toluenesulfonyl chloride (21.9 g, 115 mmol) at room temperature. The reaction mixture was reacted at room temperature for 16 hours and concentrated under reduced pressure. The reactant was poured into water (200 mL), extracted with ethyl acetate (100 mL×3), and the organic phases were combined. The organic phase was washed with saturated sodium chloride solution (100 mL), dried over anhydrous sodium sulfate, and filtered. The filtrate was concentrated under reduced pressure to remove the organic solvent, and the residue was purified by silica gel chromatography to obtain intermediate I-1.

LC-MS (ESI) $[M+H]^+$ 349.9.

$^1H$ NMR (400 MHz, $CDCl_3$) δ 7.66 (d, J=2.4 Hz, 1H), 7.58 (d, J=8.3 Hz, 2H), 7.47 (dd, J=8.6, 2.5 Hz, 1H), 7.43 (d, J=8.5 Hz, 1H), 7.28 (d, J=8.0 Hz, 2H), 3.83 (t, J=6.5 Hz, 2H), 2.43 (s, 3H), 2.40-2.35 (m, 2H), 2.00-1.91 (m, 2H).

Reference Example 2: Preparation of Intermediate I-2

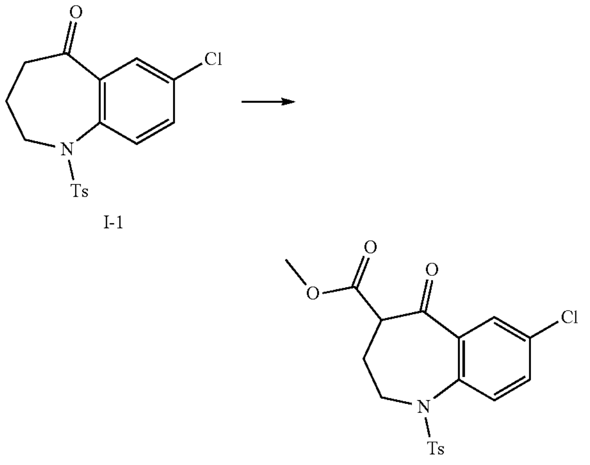

I-1

I-2

Intermediate I-1 (37.00 g, 106.00 mmol) was dissolved in anhydrous tetrahydrofuran (350 mL) at 25° C., and sodium hydride (6.36 g, 60% wt, 159.00 mmol) was added thereto in batches in an ice-water bath under argon atmosphere. After cooling and stirring in an ice-water bath for 1 hour, dimethyl carbonate (19.08 g, 212.00 mmol) was added thereto, and the reaction mixture was heated to 50° C. and stirred for 24 hours. After cooling, the reaction mixture was slowly poured into cold saturated ammonium chloride aqueous solution (500 mL), concentrated to remove most of the tetrahydrofuran, and filtered. The filter cake was washed with clear water, then slurried with petroleum ether, and filtered, and the filter cake was dried under reduced pressure to obtain intermediate I-2.

LC-MS (ESI) $[M+H]^+$ 408.0.

Reference Example 3: Preparation of Intermediate I-3

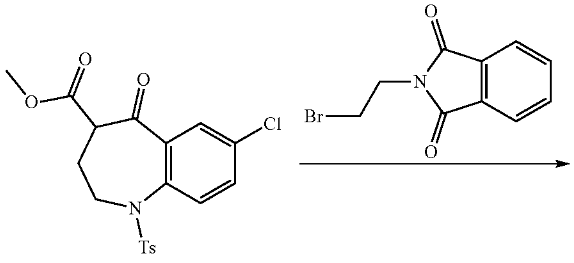

I-2

-continued

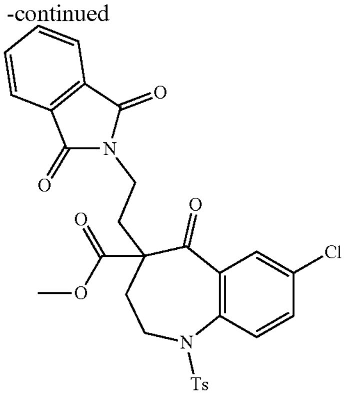

I-3

Intermediate I-2 (19.00 g, 46.68 mmol) was dissolved in anhydrous N,N-dimethylformamide (187 mL) at 25° C., and sodium carbonate (14.84 g, 140.00 mmol) and 2-(2-bromoethyl)isoindoline-1,3-dione (23.71 g, 93.36 mmol) were sequentially added thereto. The reaction mixture was stirred overnight at 90° C. under argon atmosphere. The reaction mixture was cooled, then diluted with ethyl acetate (500 mL), washed with water (150 mL×3), washed with saturated brine (100 mL), dried over anhydrous sodium sulfate, and filtered, and the filtrate was concentrated under reduced pressure to obtain a crude product. The crude product was purified by silica gel chromatography to obtain intermediate I-3.

LC-MS (ESI) $[M+H]^+$ 581.2.

Reference Example 4: Preparation of Intermediate I-4

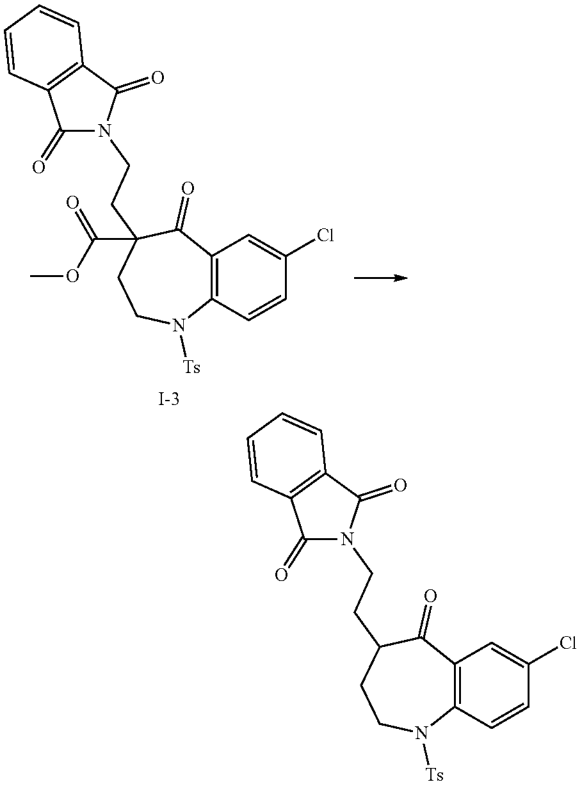

I-3

I-4

Intermediate I-3 (20.00 g, 34.48 mmol) was dissolved in dimethyl sulfoxide/water (130 mL/13 mL) at 25° C., and sodium chloride (16.70 g, 28.60 mmol) was added thereto. After the system was replaced with argon three times, the reaction mixture was stirred at 150° C. for 10 hours under argon atmosphere. The reaction mixture was cooled, then diluted with ethyl acetate (400 mL), washed with water (150 mL×3), washed with saturated brine (100 mL), dried over anhydrous sodium sulfate, and filtered, and the filtrate was concentrated under reduced pressure to obtain a crude product. The crude product was purified by silica gel chromatography to obtain intermediate I-4.

LC-MS (ESI) $[M+H]^+$ 523.2.

Reference Example 5: Preparation of Intermediate I-5

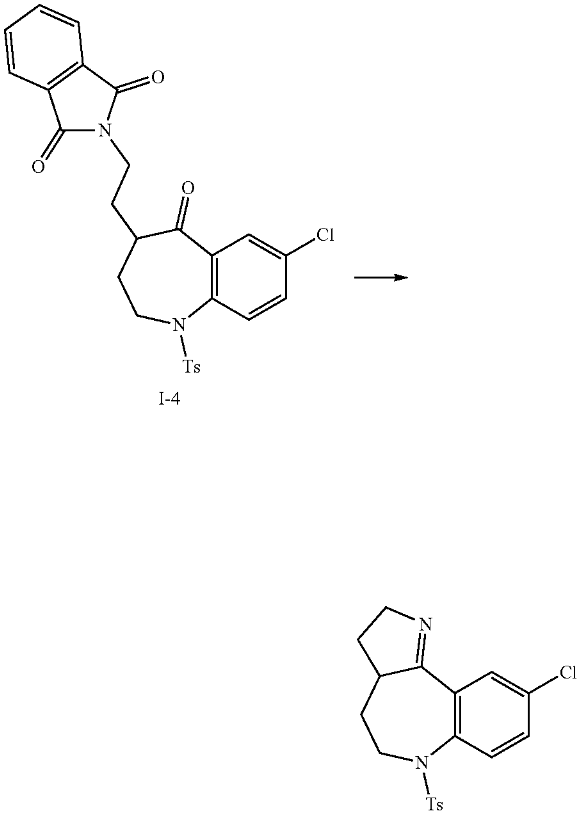

I-4

I-5

Intermediate I-4 (200 mg, 0.38 mmol) was dissolved in ethanol (7 mL) at 25° C., and 85% hydrazine hydrate (0.35 mL) was added thereto. The reaction mixture was stirred at 35° C. for 4 hours, concentrated under reduced pressure to remove most of the ethanol, added with ethyl acetate (50 mL) to dilute, sequentially washed with water (20 mL×3) and saturated brine (20 mL), dried over anhydrous sodium sulfate, filtered, and the filtrate was concentrated under reduced pressure to obtain the crude product of intermediate I-5. The crude product was directly used in the next reaction step.

LC-MS (ESI) $[M+H]^+$ 375.2.

Reference Example 6: Preparation of Intermediate I-6

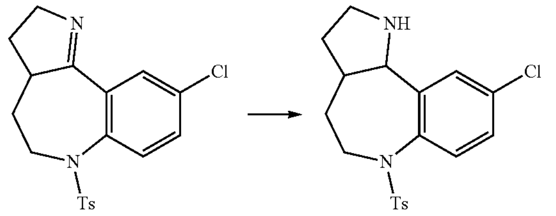

I-5 I-6

Intermediate I-5 (170 mg, 0.45 mmol) was dissolved in methanol (10 mL) at 25° C., and sodium borohydride (190 mg, 5.00 mmol) was slowly added thereto under cooling in an ice-water bath. The reaction mixture was stirred at room temperature for 1 hour, concentrated under reduced pressure to remove most of the methanol, diluted with ethyl acetate (50 mL), sequentially washed with water (20 mL×3) and saturated brine (20 mL), dried over anhydrous sodium sulfate, and filtered. The filtrate was concentrated under reduced pressure to obtain the crude product of intermediate I-6. The crude product was directly used in the next reaction step.

LC-MS (ESI) $[M+H]^+$ 377.2.

Reference Example 7: Preparation of Intermediate I-7

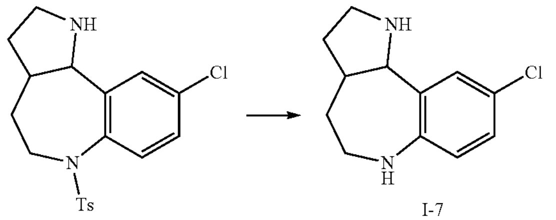

I-6 I-7

Intermediate I-6 (150 mg, 0.40 mmol) was dissolved in anhydrous methanol (20 mL) at 25° C., and magnesium chips (2.00 g, 83.33 mmol) were added thereto. The reaction mixture was replaced with nitrogen three times, and stirred overnight at 70° C. under nitrogen atmosphere (balloon). After cooling, the reaction mixture was filtered with diatomite. The filtrate was concentrated to dryness, added with a mixture of dichloromethane/methanol (10/1, 50 mL) to dissolve, washed with saturated ammonium chloride aqueous solution (20 mL×3), then washed with water (20 mL×2), dried over anhydrous sodium sulfate, and filtered. The filtrate was concentrated under reduced pressure to obtain the crude product of intermediate I-7. The crude product was directly used in the next reaction step. LC-MS (ESI) $[M+H]^+$ 223.0.

Reference Example 8: Preparation of Intermediate I-8

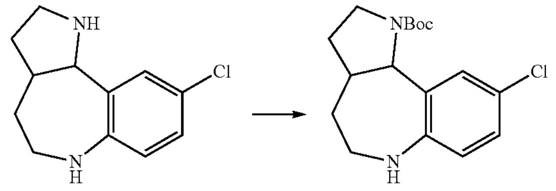

I-7 I-8

Intermediate I-7 (85 mg, 0.38 mmol) was dissolved in dichloromethane (3 mL) at 25° C., and the mixture was sequentially added with triethylamine (121 mg, 1.20 mmol) and di-tert-butyl dicarbonate (124 mg, 0.57 mmol), and stirred overnight at room temperature. The reaction mixture was concentrated to dryness, dissolved in ethyl acetate (50 mL), washed with dimethylethylenediamine aqueous solution (1 M, 10 mL×2), then washed with water (20 mL×2) and saturated brine (20 mL), dried over anhydrous sodium sulfate, and filtered. The filtrate was concentrated under reduced pressure to obtain the crude product of intermediate I-8. The crude product was directly used in the next reaction step.

LC-MS (ESI) $[M+H-56]^+$ 267.0.

Reference Example 9: Preparation of Intermediate I-9

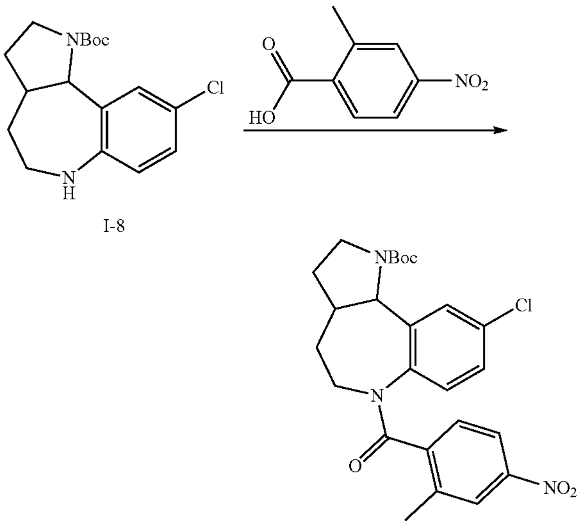

I-8

I-9

2-Methyl-4-nitrobenzoic acid (181 mg, 1.00 mmol) was dissolved in anhydrous dichloromethane (5 mL) at 25° C., and the mixture was sequentially added with N,N-dimethylformamide (20 mg) and oxalyl chloride (591 mg, 4.65 mmol) in an ice-water bath under argon atmosphere. The reaction mixture was continued to stir in an ice-water bath for 1 hour, and concentrated to dryness at room temperature to obtain an acid chloride intermediate. The acid chloride was dissolved in anhydrous dichloromethane, and the mixture was slowly added with intermediate I-8 (110 mg, 0.34 mmol), triethylamine (343 mg, 3.4 mmol), and a solution of p-dimethylaminopyridine (1.83 mg, 0.15 mmol) in dichloromethane (2.5 mL) in an ice-water bath under argon atmosphere, and stirred overnight at 40° C. after the addition was completed. The reaction mixture was added with methanol (0.5 mL) to quench, concentrated to dryness under reduced pressure, added with ethyl acetate (50 mL) to dissolve, sequentially washed with water (30 mL×2) and saturated brine (20 mL), dried over anhydrous sodium sulfate, and filtered. The filtrate was concentrated under reduced pressure to obtain a crude product. The crude product was purified by silica gel chromatography to obtain intermediate I-9.

LC-MS (ESI) $[M+H]^+$ 486.2.

Reference Example 10: Preparation of Intermediate I-10

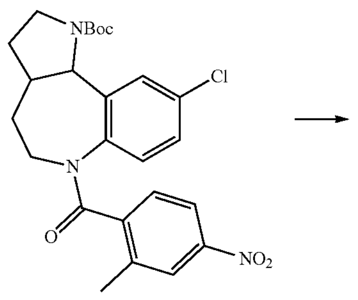

I-9

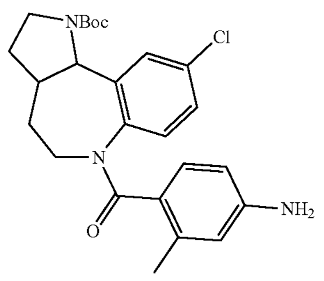

I-10

Intermediate I-9 (37.00 mg, 0.076 mmol) was dissolved in ethanol (5 mL) at 25° C., and the mixture was added with zinc powder (130 mg, 2.00 mmol), replaced with nitrogen three times, and stirred at 70° C. for 3 hours under nitrogen atmosphere (balloon). After cooling, the reaction mixture was filtered with diatomite, and the filtrate was concentrated under reduced pressure to dryness to obtain the crude product of intermediate I-10. The crude product was directly used in the next reaction step.

LC-MS (ESI) $[M+H]^+$ 456.4.

Reference Example 11: Preparation of Intermediate I-11

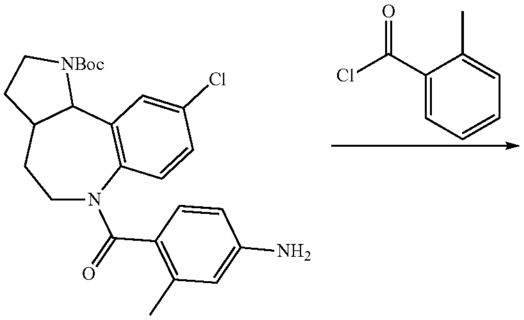

I-10

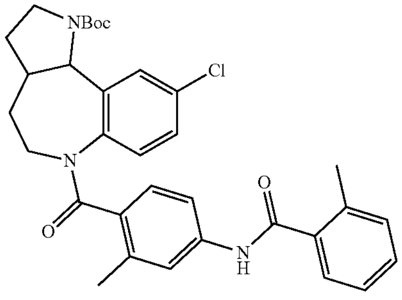

I-11

Intermediate I-10 (33 mg, 0.073 mmol) was dissolved in dichloromethane (2 mL) at 25° C., and the mixture was sequentially added with triethylamine (50 mg, 0.50 mmol) and o-toluyl chloride (23.00 mg, 0.15 mmol). The reaction mixture was stirred at room temperature for 1 hour, added with methanol (0.5 mL) to quench, and concentrated under reduced pressure to obtain a crude product. The crude product was purified by silica gel chromatography to obtain intermediate I-11.

LC-MS (ESI) $[M+H]^+$ 574.3.

Reference Example 12: Preparation of Intermediate I-12

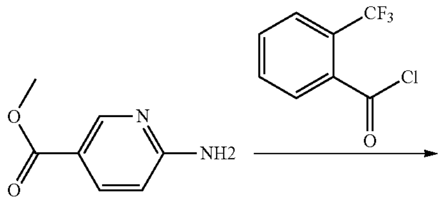

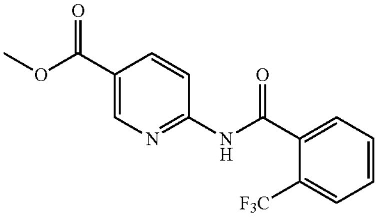

I-12

Methyl 6-aminonicotinate (1.0 g, 6.57 mmol) was dissolved in pyridine (20 mL) at room temperature, and 2-trifluoromethylbenzoyl chloride (1.51 g, 7.25 mmol) was added thereto. After the addition was completed, the reaction mixture was stirred at room temperature for 1 hour. The reaction mixture was poured into ice water (100 mL) and extracted with ethyl acetate (50 mL×3). The combined organic phase was washed with water (50 mL×5), dried over anhydrous sodium sulfate, and filtered, and the filtrate was concentrated under reduced pressure. The residue was purified by silica gel chromatography to obtain intermediate I-12.

LC-MS (ESI) $[M+H]^+$ 325.0.

Reference Example 13: Preparation of Intermediate I-13

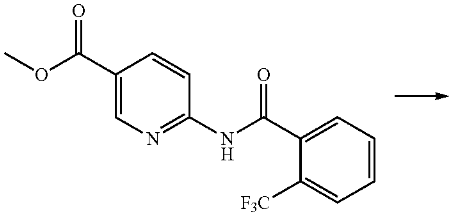

I-12

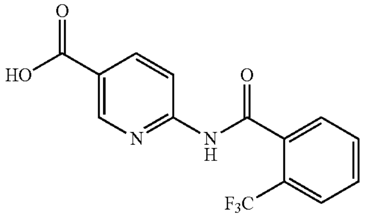

I-13

Intermediate I-12 (1.35 g, 4.16 mmol) was dissolved in tetrahydrofuran (10 mL) at room temperature, and a solution of sodium hydroxide (499 mg, 12.5 mmol) in water (2 mL) was added thereto. After the addition was completed, the reaction mixture was stirred at 70° C. for 1 hour. After the reaction was completed, the pH of the reaction mixture was adjusted to 5 to 6 with 1 N hydrochloric acid. After filtration, the solid was dried to obtain intermediate I-13.

LC-MS (ESI) $[M+H]^+$ 311.0.

Reference Example 14: Preparation of Intermediate I-14

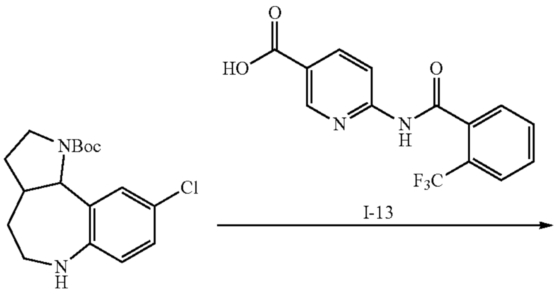

I-8

-continued

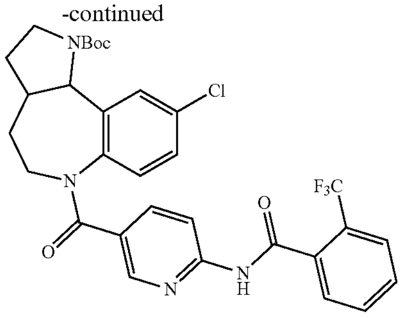

I-14

Intermediate I-8 (50 mg, 0.16 mmol) was dissolved in tetrahydrofuran (1 mL) at 25° C., and the mixture was sequentially added with pyridine (0.79 mL, 10.00 mmol), propylphosphonic anhydride (50% wt ethyl acetate solution, 0.79 mL), and intermediate I-13 (53 mg, 0.17 mmol), and stirred overnight at 65° C. in a sealed microwave tube. After cooling, the reaction mixture was concentrated to dryness under reduced pressure, dissolved in ethyl acetate (50 mL), washed with saturated sodium bicarbonate aqueous solution (30 mL×2), washed with water (20 mL×2), washed with saturated brine (20 mL), dried over sodium sulfate, and filtered. The filtrate was concentrated under reduced pressure to obtain the crude product of intermediate I-14. The crude product was directly used in the next reaction step.

LC-MS (ESI) $[M+H]^+$ 615.3.

Reference Example 15: Preparation of Intermediate I-15

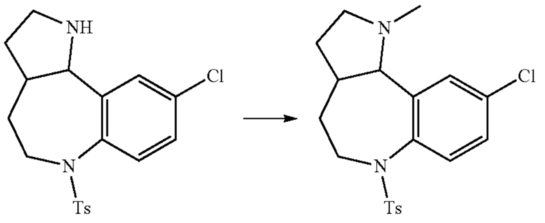

I-6 I-15

Intermediate I-6 (115 mg, 0.31 mmol) was dissolved in anhydrous dichloromethane (2 mL) at 25° C., and the mixture was sequentially added with paraformaldehyde (56 mg, 0.62 mmol) and sodium triacetoxyborohydride (20 mg, 0.93 mmol), and stirred overnight at 90° C. under argon atmosphere. The reaction mixture was cooled, added with saturated ammonium chloride aqueous solution (2 mL) to quench, concentrated under reduced pressure to remove dichloromethane, added with ethyl acetate (50 mL) to dilute, sequentially washed with water (30 mL×2) and saturated brine (20 mL), dried over anhydrous sodium sulfate, and filtered. The filtrate was concentrated under reduced pressure to obtain a crude product. The crude product was purified by silica gel chromatography to obtain intermediate I-15.

LC-MS (ESI) $[M+H]^+$391.2.

Reference Example 16: Preparation of Intermediate I-16

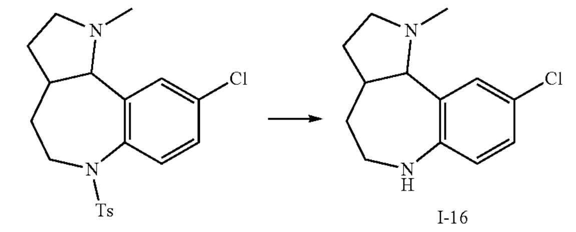

I-15 I-16

Intermediate I-15 (100 mg, 0.26 mmol) was dissolved in anhydrous methanol (20 mL) at 25° C., and magnesium chips (2.00 g, 83.33 mmol) were added thereto. The reaction mixture was replaced with nitrogen three times and stirred overnight at 70° C. under nitrogen atmosphere. After cooling, the reaction mixture was filtered with diatomite. The filtrate was concentrated to dryness, added with a mixture of dichloromethane/methanol (10/1, 50 mL) to dissolve, washed with saturated ammonium chloride aqueous solution (20 mL×3), then washed with water (20 mL×2), dried over anhydrous sodium sulfate, and filtered. The filtrate was concentrated under reduced pressure to obtain the crude product of intermediate I-16. The crude product was directly used in the next reaction step.

LC-MS (ESI) $[M+H]^+$ 237.2.

Reference Example 17: Preparation of Intermediate I-17

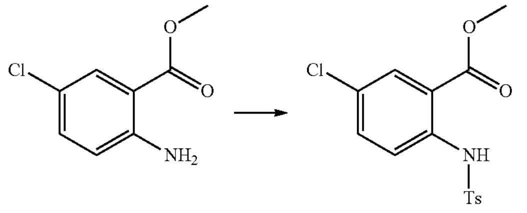

I-17

To a solution of methyl 2-amino-5-chlorobenzoate (200 g, 1.08 mol) in pyridine (1000 mL) was added 4-toluenesulfonyl chloride (247 g, 1.30 mol) at room temperature. The reaction mixture was stirred at room temperature for 16 hours. The reaction mixture was poured into ice water (1500 mL) and extracted with ethyl acetate (1000 mL×3). The organic phases were combined, sequentially washed with water (1500 mL) and saturated brine (1500 mL), dried over anhydrous sodium sulfate, and filtered, and the filtrate was concentrated under reduced pressure to remove the organic solvent to obtain a crude product. The crude product was purified by slurrying with ethyl acetate/petroleum ether (5:95) to obtain intermediate I-17.

LC-MS (ESI) $[M+H]^+$ 340.0.

$^1$H NMR (400 MHz, DMSO-$d_6$) δ 10.29 (s, 1H), 7.78 (d, J=2.6 Hz, 1H), 7.67 (d, J=8.3 Hz, 2H), 7.63 (dd, J=8.9, 2.6 Hz, 1H), 7.46 (d, J=8.9 Hz, 1H), 7.36 (d, J=8.1 Hz, 2H), 3.80 (s, 3H), 2.34 (s, 3H).

Reference Example 18: Preparation of Intermediate I-18

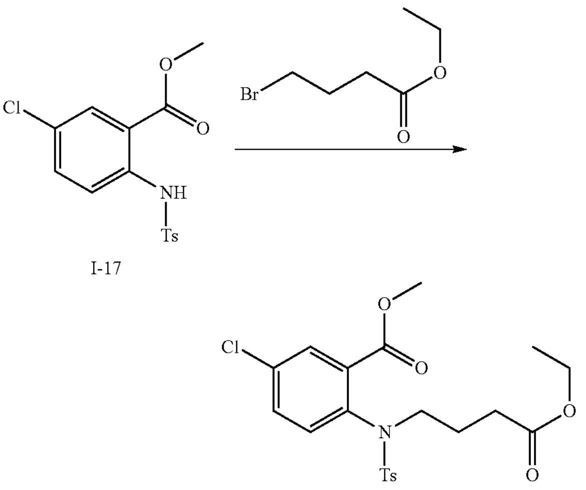

I-17

I-18

To a solution of intermediate I-17 (200 g, 0.589 mol) and ethyl 4-bromobutyrate (121 g, 0.620 mol) in N,N-dimethylformamide (1000 mL) was added cesium carbonate (384 g, 1.18 mol) at room temperature, and the reaction mixture was stirred at 120° C. for 2 hours, cooled to room temperature, poured into ice water (2 L), and extracted with ethyl acetate (1000 mL×3). The organic phases were combined, sequentially washed with water (1000 mL×3) and saturated brine (1000 mL), dried over anhydrous sodium sulfate, and filtered, and the filtrate was concentrated under reduced pressure to remove the organic solvent to obtain a crude product. The crude product was purified by slurrying with ethyl acetate/petroleum ether (5:95) to obtain intermediate I-18.

LC-MS (ESI) $[M+H]^+$ 454.1.

$^1$H NMR (400 MHz, DMSO-$d_6$) δ 7.79 (d, J=2.6 Hz, 1H), 7.61 (dd, J=8.6, 2.6 Hz, 1H), 7.39 (s, 4H), 6.97 (d, J=8.6 Hz, 1H), 4.01 (q, J=7.1 Hz, 2H), 3.76 (s, 3H), 3.70 (m, 1H), 3.45 (m, 1H), 2.45-2.32 (m, 5H), 1.71-1.60 (m, 2H), 1.14 (t, J=7.1 Hz, 3H).

Reference Example 19: Preparation of Intermediate I-19

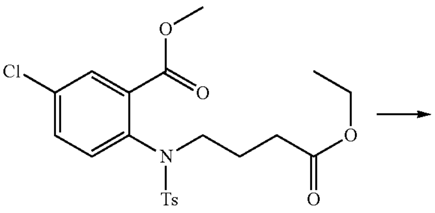

I-18

-continued

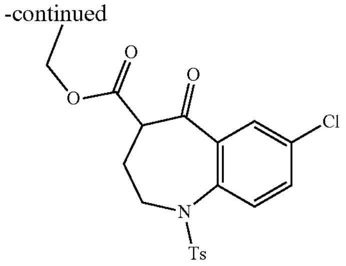

I-19

To toluene (1.6 L) was added potassium tert-butoxide (69.0 g, 0.615 mol) at room temperature, and the mixture was heated to 70° C., stirred for 30 minutes, and then added with intermediate I-18 (186 g, 0.410 mol). The reaction mixture was stirred at 100° C. for 1 hour, cooled to room temperature, added with water (1 L), and extracted with ethyl acetate (1 L×2). The organic phases were combined, washed with saturated brine (1 L), dried over anhydrous sodium sulfate, and filtered, and the filtrate was concentrated under reduced pressure to remove the organic solvent to obtain the crude product of intermediate I-19. The crude product was directly used in the next reaction step without purification.

Reference Example 20: Preparation of Intermediate I-20

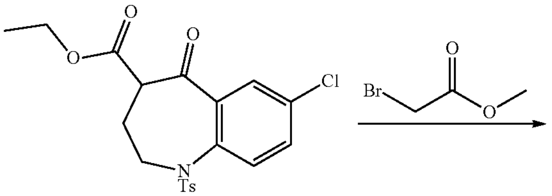

I-19

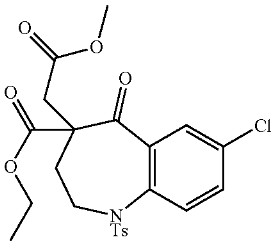

I-20

Intermediate I-19 (5.00 g, 11.87 mmol) was dissolved in anhydrous tetrahydrofuran (60 mL) at 25° C., and the mixture was cooled in an ice-water bath under argon atmosphere, and slowly added with 60% sodium hydride (0.95 g, 23.74 mmol). After cooling and stirring in an ice-water bath for 0.5 hours, methyl bromoacetate (3.63 g, 23.74 mmol) was added thereto, and the reaction mixture was stirred overnight at room temperature, poured into cold saturated ammonium chloride aqueous solution (100 mL), concentrated under reduced pressure to remove most of the tetrahydrofuran, and extracted with ethyl acetate (150 mL×2). The combined organic phase was washed with water (50 mL), washed with saturated brine (50 mL), dried over anhydrous sodium sulfate, and filtered. The filtrate was concentrated under reduced pressure and the residue was purified by silica gel chromatography to obtain intermediate I-20.

LC-MS (ESI) $[M+H]^+$ 494.2.

Reference Example 21: Preparation of Intermediate I-21

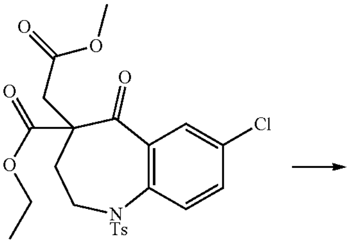

I-20

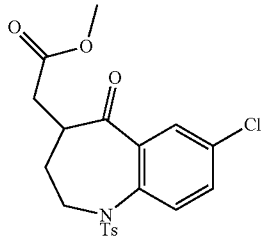

I-21

Intermediate I-20 (5.50 g, 11.16 mmol) was dissolved in dimethyl sulfoxide/water (55 mL/5 mL) at 25° C., and sodium chloride (0.71 g, 12.00 mmol) was added thereto. After the system was replaced with argon three times, the reaction mixture was stirred at 150° C. for 10 hours under argon atmosphere. The reaction mixture was cooled, then diluted with ethyl acetate (200 mL), washed with water (50 mL×3), washed with saturated brine (50 mL), dried over anhydrous sodium sulfate, and filtered. The filtrate was concentrated under reduced pressure and the residue was purified by silica gel chromatography to obtain intermediate I-21.

LC-MS (ESI) $[M+H]^+$ 422.0.

Reference Example 22: Preparation of Intermediate I-22

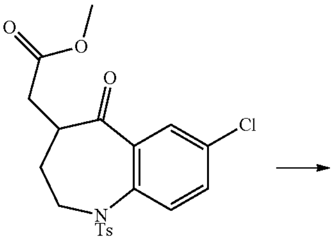

I-21

-continued

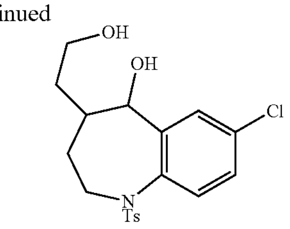

I-22

Intermediate I-21 (1.00 g, 2.38 mmol) was dissolved in anhydrous tetrahydrofuran (15 mL) at 25° C. The system was cooled with an ice-water bath under argon atmosphere, and a solution of lithium borohydride in tetrahydrofuran (1 M, 7.14 mL, 7.14 mmol) was slowly added thereto under stirring. After the addition was completed, the reaction mixture was naturally warmed to room temperature, stirred for about 3 hours, poured into cold saturated ammonium chloride aqueous solution (100 mL), concentrated under reduced pressure to remove most of the tetrahydrofuran, and extracted with a mixture of dichloromethane/methanol (10/1, 50 mL×2). The organic phases were combined, washed with water (30 mL), washed with saturated brine (20 mL), dried over anhydrous sodium sulfate, and filtered, and the filtrate was concentrated under reduced pressure to remove the organic solvent to obtain the crude product of intermediate I-22. The crude product was directly used in the next reaction step without purification.

LC-MS (ESI) $[M-H_2O+H]^+$ 378.2.

Reference Example 23: Preparation of Intermediates I-23A and I-23B

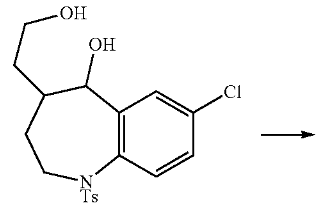

I-22

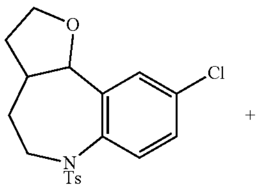

I-23A

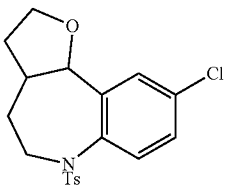

I-23B

Intermediate I-22 (900 mg, 2.27 mmol) was dissolved in anhydrous dichloromethane (30 mL) at 25° C., and boron trifluoride diethyl etherate (1.26 mL, 10 mmol) was added thereto. After the system was replaced with argon three times, the reaction mixture was stirred at 40° C. for 16 hours under argon atmosphere, and concentrated under reduced pressure, and the residue was purified by silica gel chromatography to obtain intermediate I-23A (Rt=1.342 min) and intermediate I-23B (Rt=1.321 min).

LCMS analysis method: Chromatographic column: Infinitylab Poroshell 120 EC-C18 3.0×30 mm, 1.9 μm Mobile phase: A: water (0.01% trifluoroacetic acid) B: acetonitrile (0.01% trifluoroacetic acid)

Elution gradient: 5% to 95% B, 0.7 minutes; 95% B, 0.8 minutes; then 5% B, 0.5 minutes Flow rate: 1.2 mL/min Chromatographic column temperature: 40° C.

Mass spectrum scanning range: 100 to 1000

Intermediate I-23A (Rt=1.342 min) LC-MS (ESI) $[M+H]^+$ 378.0.

Intermediate I-23B (Rt=1.321 min) LC-MS (ESI) $[M+H]^+$ 378.0.

Reference Example 24: Preparation of Intermediate I-24

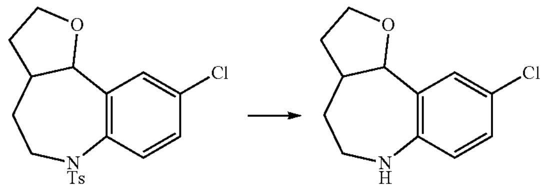

I-23A I-24

Intermediate I-23A (280.00 mg, 0.74 mmol) was dissolved in anhydrous methanol (20 mL) at 25° C., and magnesium chips (2.00 g, 83.33 mmol) were added thereto. The reaction mixture was replaced with nitrogen three times and stirred overnight at 70° C. under nitrogen atmosphere. After cooling, the reaction mixture was filtered with diatomite. The filtrate was concentrated to dryness under reduced pressure, added with ethyl acetate (100 mL) to dissolve, washed with saturated ammonium chloride aqueous solution (30 mL×3), then washed with water (30 mL×2), washed with saturated brine (20 mL), dried over anhydrous sodium sulfate, and filtered. The filtrate was concentrated under reduced pressure to remove the organic solvent to obtain the crude product of intermediate I-24. The crude product was directly used in the next reaction step without purification.

LC-MS (ESI) $[M+H]^+$ 224.0.

Reference Example 25: Preparation of Intermediate I-25

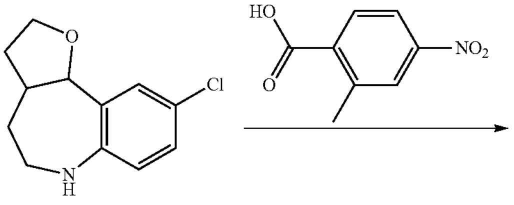

I-24

-continued

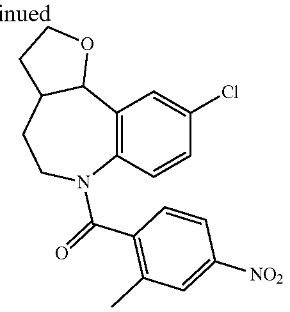

I-25

2-Methyl-4-nitrobenzoic acid (168 mg, 0.93 mmol) was dissolved in anhydrous dichloromethane (5 mL) at 25° C., and the mixture was sequentially added with N,N-dimethylformamide (20 mg) and oxalyl chloride (591 mg, 4.65 mmol) in an ice-water bath under argon atmosphere. The reaction mixture was continued to stir in an ice-water bath for 1 hour and concentrated to dryness at room temperature to obtain an acid chloride intermediate. The acid chloride was dissolved in anhydrous dichloromethane, and the mixture was slowly added with intermediate I-24 (70 mg, 0.31 mmol), triethylamine (310 mg, 3.10 mmol), and a solution of p-dimethylaminopyridine (1.83 mg, 0.15 mmol) in dichloromethane (2 mL) in an ice-water bath under argon atmosphere, and stirred overnight at 40° C. after the addition was completed. After the reaction was completed, the reaction mixture was added with methanol (0.5 mL) to quench, concentrated to dryness under reduced pressure, added with ethyl acetate (50 mL) to dissolve, sequentially washed with water (30 mL×2) and saturated brine (20 mL), dried over anhydrous sodium sulfate, and filtered. The filtrate was concentrated under reduced pressure and the residue was purified by silica gel chromatography to obtain intermediate I-25.

LC-MS (ESI) $[M+H]^+$ 387.2.

Reference Example 26: Preparation of Intermediate I-26

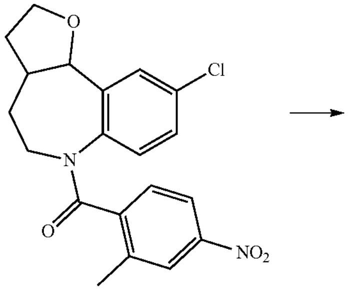

I-25

-continued

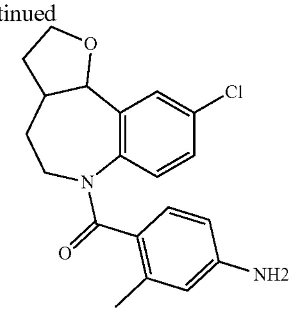

I-26

Intermediate I-25 (40 mg, 0.10 mmol) was dissolved in ethanol (5 mL) at 25° C., and the mixture was added with zinc powder (130 mg, 2.00 mmol), replaced with nitrogen three times, and stirred at 70° C. for 3 hours under nitrogen atmosphere. After cooling, the reaction mixture was filtered with diatomite, and the filtrate was concentrated under reduced pressure to remove the organic solvent to obtain the crude product of intermediate I-26. The crude product was directly used in the next reaction step without purification.

LC-MS (ESI) $[M+H]^+$ 357.2.

Reference Example 27: Preparation of Intermediate I-27

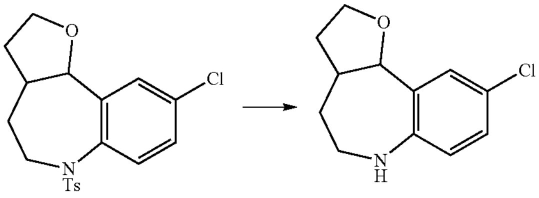

I-23B

I-27

Intermediate I-23B (280 mg, 0.74 mmol) was dissolved in anhydrous methanol (20 mL) at 25° C., and magnesium chips (2.00 g, 83.33 mmol) were added thereto. The reaction mixture was replaced with nitrogen three times and stirred overnight at 70° C. under nitrogen atmosphere. After cooling, the reaction mixture was filtered with diatomite. The filtrate was concentrated to dryness under reduced pressure, added with ethyl acetate (100 mL) to dissolve, washed with saturated ammonium chloride aqueous solution (30 mL×3), then washed with water (30 mL×2), washed with saturated brine (20 mL), dried over anhydrous sodium sulfate, and filtered. The filtrate was concentrated under reduced pressure to remove the organic solvent to obtain the crude product of intermediate I-27. The crude product was directly used in the next reaction step without purification.

LC-MS (ESI) $[M+H]^+$ 224.0.

Reference Example 28: Preparation of Intermediate I-28

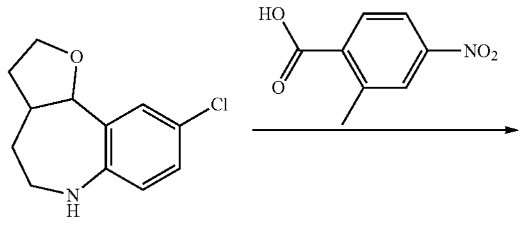

I-27

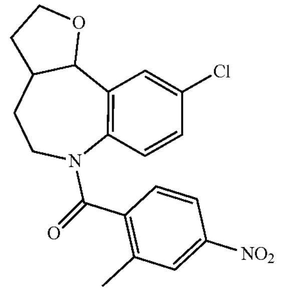

I-28

2-Methyl-4-nitrobenzoic acid (168 mg, 0.93 mmol) was dissolved in anhydrous dichloromethane (5 mL) at 25° C., and the mixture was sequentially added with N,N-dimethylformamide (20 mg) and oxalyl chloride (591 mg, 4.65 mmol) in an ice-water bath under argon atmosphere. The reaction mixture was continued to stir in an ice-water bath for 1 hour, and concentrated to dryness at room temperature to obtain an acid chloride intermediate. The acid chloride was dissolved in anhydrous dichloromethane, and the mixture was slowly added with intermediate I-27 (50 mg, 0.22 mmol), triethylamine (310 mg, 3.10 mmol), and a solution of p-dimethylaminopyridine (1.83 mg, 0.15 mmol) in dichloromethane (2 mL) in an ice-water bath under argon atmosphere, and stirred overnight at 40° C. after the addition was completed. After the reaction was completed, the reaction mixture was added with methanol (0.5 mL) to quench, concentrated to dryness under reduced pressure, added with ethyl acetate (50 mL) to dissolve, sequentially washed with water (30 mL×2) and saturated brine (20 mL), dried over anhydrous sodium sulfate, and filtered. The filtrate was concentrated under reduced pressure and the residue was purified by silica gel chromatography to obtain intermediate I-28.

LC-MS (ESI) $[M+H]^+$ 387.2.

Reference Example 29: Preparation of Intermediate I-29

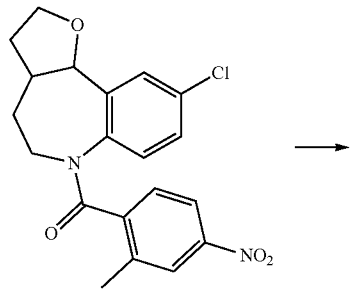

I-28

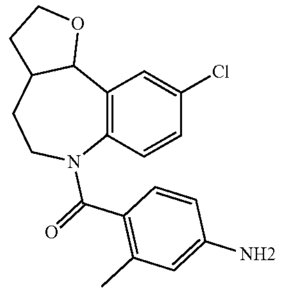

I-29

Intermediate I-28 (30 mg, 0.078 mmol) was dissolved in ethanol (5 mL) at 25° C., and the mixture was added with zinc powder (130 mg, 2.00 mmol), replaced with nitrogen three times, and stirred at 70° C. for 3 hours under nitrogen atmosphere. After cooling, the reaction mixture was filtered with diatomite, and the filtrate was concentrated under reduced pressure to remove the organic solvent to obtain the crude product of intermediate I-29. The crude product was directly used in the next reaction step without purification.

LC-MS (ESI) $[M+H]^+$ 357.2.

Reference Example 30: Preparation of Intermediate I-30

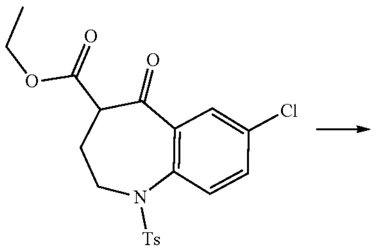

I-19

-continued

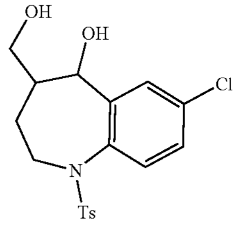

I-30

Intermediate I-19 (5.0 g, 11.85 mmol) was dissolved in tetrahydrofuran (50 mL) at room temperature. To the reaction system was added sodium borohydride (8.78 g, 232.09 mmol) under nitrogen atmosphere, and the reaction mixture was stirred at room temperature for 24 hours, diluted with water (50 mL), and extracted with ethyl acetate (50 mL×2). The organic phases were combined, washed with saturated brine (30 mL×2), dried over anhydrous sodium sulfate, and filtered. The filtrate was concentrated under reduced pressure to remove the organic solvent to obtain a crude product. The crude product was purified by silica gel chromatography to obtain intermediate I-30.

LC-MS (ESI) $[M+H]^+$ 382.2.

Reference Example 31: Preparation of Intermediate I-31

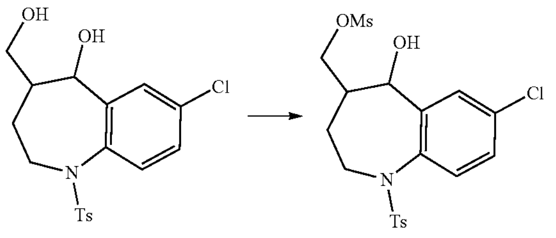

I-30 I-31

Intermediate I-30 (3.54 g, 9.29 mmol) was dissolved in dichloromethane (10 mL) at room temperature, and methylsulfonyl chloride (1.16 g, 10.22 mmol), triethylamine (1.41 g, 13.93 mmol) were sequentially added thereto, and the reaction mixture was stirred at 0° C. for 1 hour under argon atmosphere, diluted with water (50 mL), and extracted with dichloromethane (30 mL×2). The organic phases were combined, washed with saturated brine (30 mL×2), dried over anhydrous sodium sulfate, and filtered. The filtrate was concentrated under reduced pressure to remove the organic solvent to obtain the crude product of intermediate I-31. The crude product was directly used in the next reaction step without purification.

Reference Example 32: Preparation of Intermediate I-32

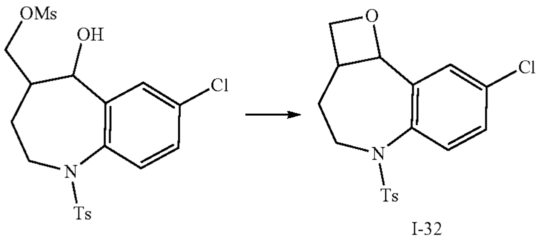

I-31 I-32

Intermediate I-31 (3.71 g, 8.08 mmol) was dissolved in tetrahydrofuran (10 mL) at room temperature. To the reaction mixture was added 60% sodium hydride (808 mg, 20.20 mmol) under argon atmosphere, and the reaction mixture was stirred at room temperature for 16 hours, added with water (50 mL) to quench, and extracted with ethyl acetate (30 mL×2). The organic phases were combined, washed with saturated brine (30 mL×2), dried over anhydrous sodium sulfate, and filtered. The filtrate was concentrated under reduced pressure to remove the organic solvent to obtain a crude product. The crude product was purified by silica gel chromatography to obtain intermediate I-32.

LC-MS (ESI) $[M+Na]^+$ 386.0.

Reference Example 33: Preparation of Intermediate I-33

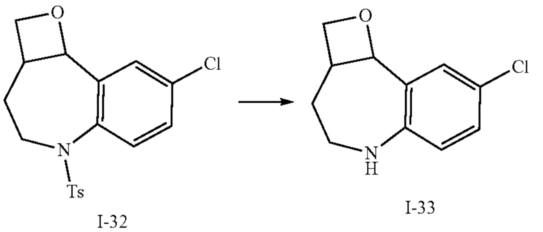

I-32 I-33

Intermediate I-32 (2.34 g, 6.43 mmol) was dissolved in methanol (50 mL) at room temperature. Magnesium chips (1.54 g, 64.40 mmol) were added thereto under nitrogen atmosphere, and the reaction mixture was stirred at 70° C. for 1 hour. The reaction system was cooled to room temperature, diluted with saturated ammonium chloride solution (50 mL), extracted with ethyl acetate (30 mL×2), and the organic phases were combined, washed with saturated ammonium chloride aqueous solution (30 mL×2), dried over sodium sulfate, and filtered. The filtrate was concentrated under reduced pressure to remove the organic solvent to obtain a crude product. The crude product was purified by silica gel chromatography to obtain intermediate I-33.

LC-MS (ESI) $[M+H]^+$ 210.0.

Reference Example 34: Preparation of Intermediate I-34

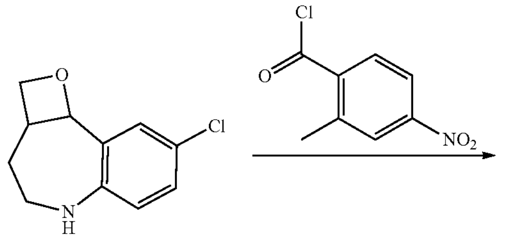

I-33

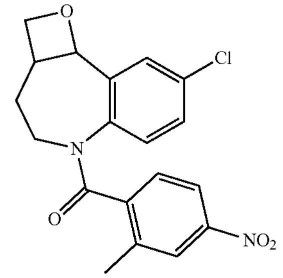

I-34

Intermediate I-33 (400 mg, 1.91 mmol) was dissolved in dichloromethane (20 mL) at room temperature. N,N-Diisopropylethylamine (740 mg, 5.74 mmol) was added thereto at room temperature under nitrogen atmosphere. The above reaction mixture was added with 2-methyl-4-nitrobenzoyl chloride (455 mg, 2.29 mmol), stirred at room temperature for 16 hours, diluted with water (20 mL), and extracted with dichloromethane (30 mL×2). The organic phases were combined, washed with saturated sodium chloride aqueous solution (30 mL×2), dried over anhydrous sodium sulfate, and filtered. The filtrate was concentrated under reduced pressure to remove the organic solvent to obtain a crude product. The crude product was purified by silica gel chromatography to obtain intermediate I-34.

LC-MS (ESI) $[M+H]^+$ 373.2.

Reference Example 35: Preparation of Intermediate I-35

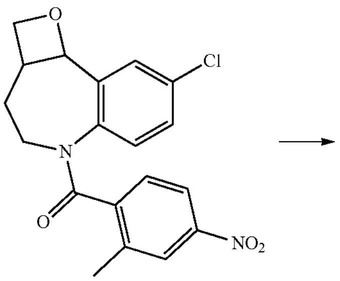

I-34

-continued

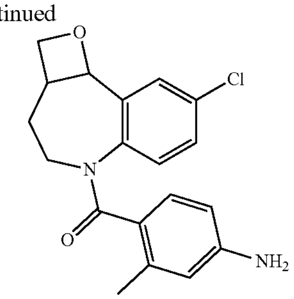

I-35

Intermediate I-34 (100 mg, 0.27 mmol) was dissolved in tetrahydrofuran (10 mL) at room temperature, and zinc powder (349 mg, 5.37 mmol) and ammonium chloride (284 mg, 5.37 mmol) were added thereto under nitrogen atmosphere, and the reaction mixture was stirred at 80° C. for 1 hour, filtered, and concentrated to dryness under reduced pressure to obtain the crude product of intermediate I-35. The crude product was directly used in the next reaction step without purification.

LC-MS (ESI) $[M+H]^+$ 343.2.

Reference Example 36: Preparation of Intermediate I-36

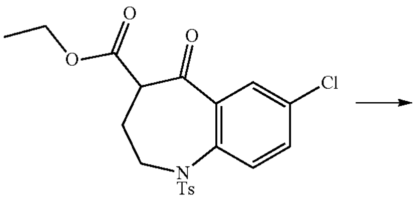

I-19

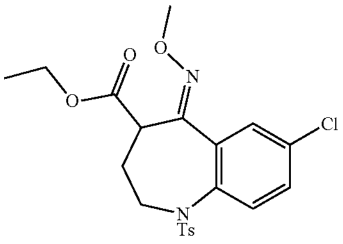

I-36

Intermediate I-19 (2.00 g, 4.75 mmol) was dissolved in pyridine (10 mL) at 25° C., and methoxyamine hydrochloride (0.79 g, 9.50 mmol) was added thereto. The reaction mixture was stirred in a sealed microwave tube at 80° C. for 10 hours, then concentrated, diluted with ethyl acetate (100 mL), washed with saturated ammonium chloride aqueous solution (50 mL×2), washed with water (50 mL×2), washed with saturated sodium chloride aqueous solution (30 mL), dried over anhydrous sodium sulfate, and filtered. The filtrate was concentrated under reduced pressure to remove the organic solvent to obtain the crude product of intermediate I-36. The crude product was directly used in the next reaction step without purification.

LC-MS (ESI) $[M+H]^+$ 451.2.

Reference Example 37: Preparation of Intermediate I-37

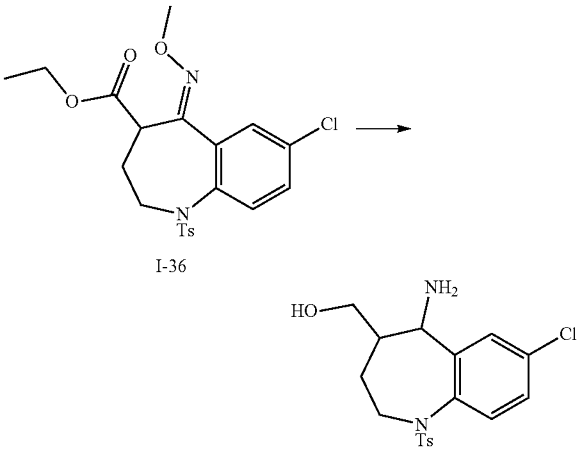

I-36

I-37

Intermediate I-36 (2.20 g) was dissolved in borane tetrahydrofuran (24.50 mL, 22.05 mmol) at 25° C., and the mixture was replaced with argon three times and stirred overnight at 50° C. under argon atmosphere. Under cooling in an ice-water bath, the mixture was added with methanol dropwise until no bubbling was observed, and concentrated under reduced pressure to obtain the crude product of intermediate I-37. The crude product was directly used in the next reaction step without purification.

LC-MS (ESI) $[M+H]^+$ 381.2.

Reference Example 38: Preparation of Intermediate I-38

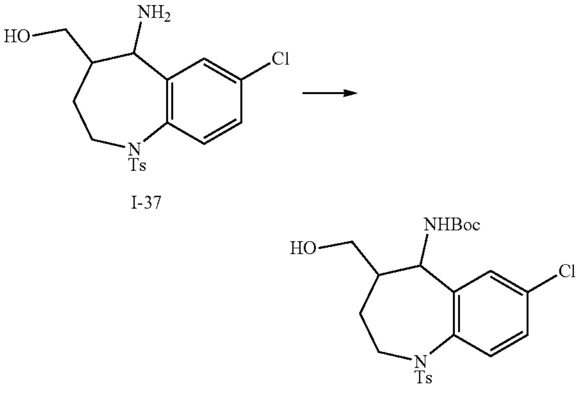

I-37

I-38

Intermediate I-37 (2.50 g) was dissolved in dichloromethane (20 mL) at 25° C., and triethylamine (1.48 g, 14.70 mmol), di-tert-butyl dicarbonate (2.20 g, 10.09 mmol) were sequentially added thereto, and stirred overnight at 25° C. The reaction mixture was concentrated, dissolved in ethyl acetate (100 mL), washed with dimethylethylenediamine aqueous solution (1 M, 30 mL×2), washed with water (30 mL), washed with saturated sodium chloride aqueous solution (30 mL), dried over anhydrous sodium sulfate, and filtered. The filtrate was concentrated under reduced pressure to remove the organic solvent to obtain the crude product of intermediate I-38. The crude product was directly used in the next reaction step without purification.

LC-MS (ESI) $[M+H-56]^+$ 425.3.

Reference Example 39: Preparation of Intermediate I-39

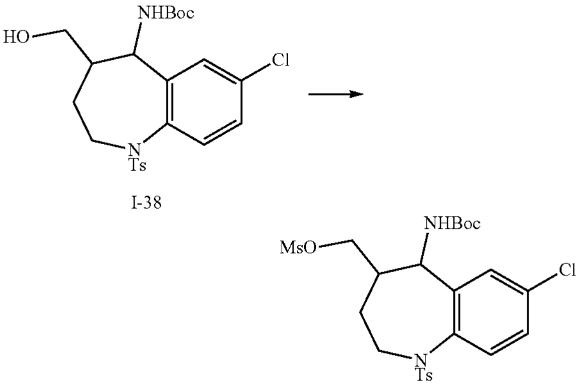

I-38

I-39

Intermediate I-38 (2.50 g) was dissolved in anhydrous dichloromethane (20 mL) at 25° C., and the mixture was added with triethylamine (1.00 g, 9.90 mmol), and then dropwise added with methanesulfonyl chloride (0.82 g, 7.13 mmol) in ice-water bath under argon atmosphere. The reaction mixture was stirred at 25° C. for 1 hour, added dropwise with methanol (1 mL) to quench, concentrated under reduced pressure, dissolved in ethyl acetate (100 mL), washed with saturated sodium bicarbonate aqueous solution (30 mL×2), washed with water (30 mL), washed with saturated sodium chloride aqueous solution (30 mL), dried over anhydrous sodium sulfate, and filtered. The filtrate was concentrated under reduced pressure to remove the organic solvent to obtain a crude product. The crude product was purified by silica gel chromatography to obtain intermediate I-39.

LC-MS (ESI) $[M+H-100]^+$ 459.0.

Reference Example 40: Preparation of Intermediate I-40

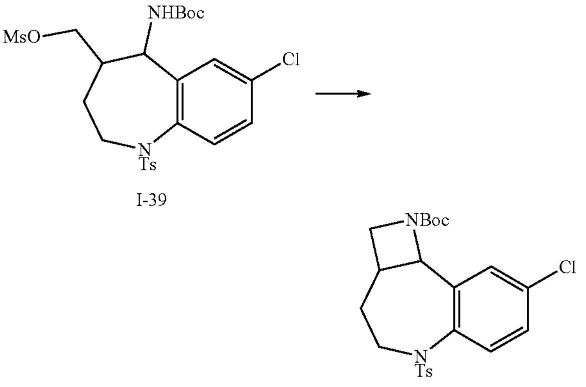

I-39

I-40

Intermediate I-39 (2.00 g, 3.58 mmol) was dissolved in anhydrous tetrahydrofuran (10 mL) at 25° C., and the mixture was added with 60% of sodium hydride (2.90 g, 72.5 mmol), replaced with argon three times at 70° C. and stirred overnight. The reaction mixture was cooled, poured into cold saturated ammonium chloride aqueous solution (20 mL), concentrated under reduced pressure to remove most of the tetrahydrofuran, and extracted with ethyl acetate (50 mL×2). The organic phases were combined, washed with water (30 mL×2), washed with saturated sodium chloride aqueous solution (30 mL), dried over anhydrous sodium sulfate, and filtered. The filtrate was concentrated under reduced pressure to remove the organic solvent to obtain a crude product. The crude product was purified by silica gel chromatography to obtain intermediate I-40.

LC-MS (ESI) $[M+H-56]^+$ 406.90.

Reference Example 41: Preparation of Intermediate I-41

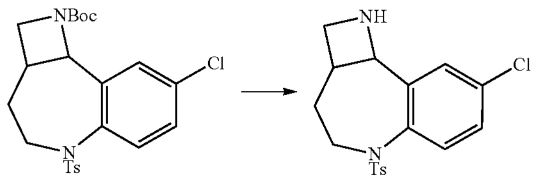

I-40 I-41

Intermediate I-40 (0.45 g, 0.97 mmol) was dissolved in a solution of trifluoroacetic acid in dichloromethane (1/10, 5 mL) at 25° C., and the mixture was stirred for 1 hour and poured into cold saturated sodium bicarbonate aqueous solution (50 mL), concentrated at room temperature to remove most of the dichloromethane, and extracted with ethyl acetate (30 mL×2). The organic phases were combined, washed with water (20 mL×2), washed with saturated sodium chloride aqueous solution (20 mL), dried over anhydrous sodium sulfate, and filtered. The filtrate was concentrated under reduced pressure to remove the organic solvent to obtain the crude product of intermediate I-41. The crude product was directly used in the next reaction step without purification.

Reference example 42: Preparation of Intermediate I-42

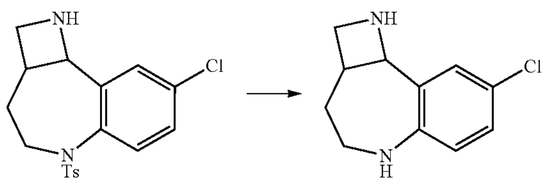

I-41 I-42

Intermediate I-41 (0.31 g, 0.86 mmol) was dissolved in anhydrous methanol (20 mL) at 25° C., and the mixture was added with magnesium chips (1.20 g, 50.00 mmol), replaced with argon three times, and stirred overnight at 70° C. under argon atmosphere. After cooling, the reaction mixture was filtered with diatomite. The filtrate was concentrated, added with dichloromethane/methanol (10/1, 100 mL) to dilute, washed with saturated ammonium chloride aqueous solution (30 mL×2), washed with water (30 mL×2), washed with saturated sodium chloride aqueous solution (20 mL), dried over anhydrous sodium sulfate, and filtered. The filtrate was concentrated under reduced pressure to remove the organic solvent to obtain the crude product of intermediate I-42. The crude product was directly used in the next reaction step without purification.

LC-MS (ESI) $[M+H]^+$ 208.8.

Reference Example 43: Preparation of Intermediate I-43

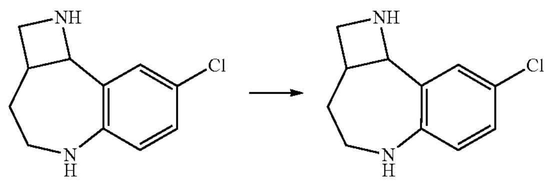

I-42 I-43

Intermediate I-42 (0.15 g) was dissolved in dichloromethane (3 mL) at 25° C., and triethylamine (0.22 g, 2.16 mmol), di-tert-butyl dicarbonate (0.31 g, 1.44 mmol) were sequentially added thereto. The reaction mixture was stirred at 25° C. for 3 hours and concentrated under reduced pressure. The residue was purified by silica gel chromatography to obtain intermediate I-43.

LC-MS (ESI) $[M+H]^+$ 309.2.

Reference Example 44: Preparation of Intermediate I-44

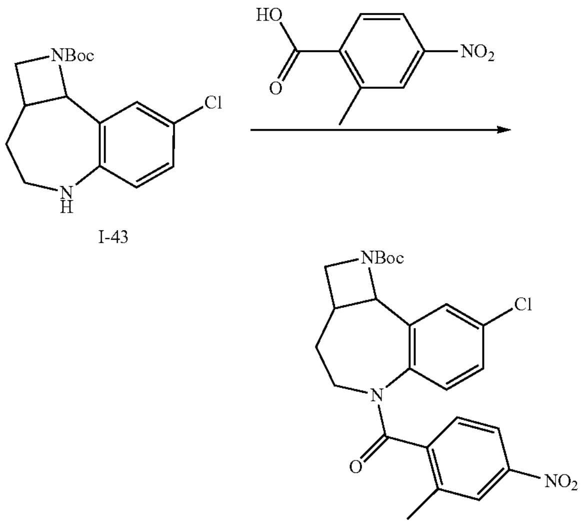

I-43

I-44

2-Methyl-4-nitrobenzoic acid (0.58 g, 3.20 mmol) was dissolved in anhydrous dichloromethane (5 mL) at 25° C., and the mixture was added with a drop of N,N-dimethylformamide, cooled in an ice-water bath under argon atmosphere, slowly added dropwise with oxalyl chloride (1.63 g, 12.8 mmol), stirred in an ice-water bath for 1 hour, and then concentrated to dryness at room temperature to obtain an acid chloride intermediate. The acid chloride intermediate was dissolved in anhydrous dichloromethane (5 mL), and triethylamine (2.56 g, 25.60 mmol), 4-dimethylaminopyridine (2.44 mg, 0.02 mmol), and Intermediate I-43 (100 mg, 0.32 mmol) were added thereto in an ice-water bath under argon atmosphere. The reaction mixture was stirred overnight at 40° C., then cooled to room temperature, added dropwise with methanol (2 mL) to quench, concentrated under reduced pressure, diluted with ethyl acetate (50 mL), washed with saturated sodium bicarbonate aqueous solution (20 mL×2), washed with water (20 mL), washed with saturated sodium chloride aqueous solution (20 mL), dried over anhydrous sodium sulfate, and filtered. The filtrate was concentrated under reduced pressure to remove the organic solvent to obtain a crude product. The crude product was purified by silica gel chromatography to obtain intermediate I-44.

LC-MS (ESI) $[M+H]^+$ 471.8.

Reference Example 45: Preparation of Intermediate I-45

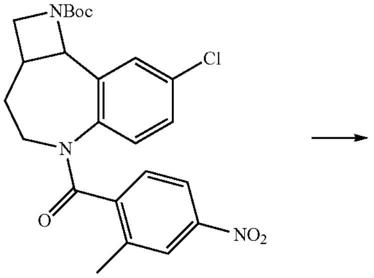

I-44

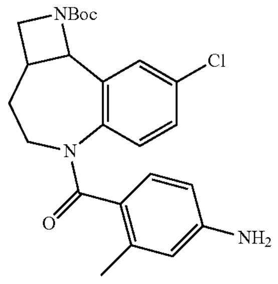

I-45

Intermediate I-44 (63 mg, 0.13 mmol) was dissolved in tetrahydrofuran (5 mL) at 25° C., and the mixture was sequentially added with zinc powder (87 mg, 1.30 mmol) and ammonium chloride (35 mg, 0.65 mmol), and stirred at 70° C. for 5 hours under argon atmosphere. After cooling, the reaction mixture was filtered with diatomite. The filtrate was concentrated under reduced pressure, added with ethyl acetate (50 mL) to dissolve, washed with water (20 mL×2), washed with saturated sodium chloride aqueous solution (20 mL), dried over anhydrous sodium sulfate, and filtered. The filtrate was concentrated under reduced pressure to remove the organic solvent to obtain the crude product of Intermediate I-45. The crude product was directly used in the next reaction step without purification.

LC-MS (ESI) $[M+H]^+$ 441.8.

Reference Example 46: Preparation of Intermediate I-46

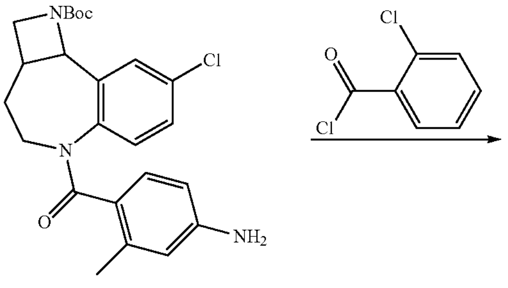

I-45

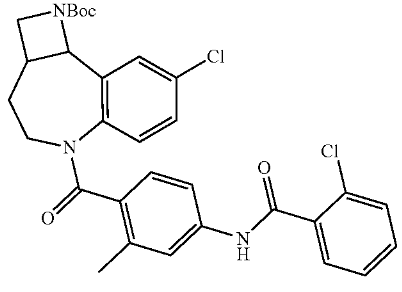

I-46

Intermediate I-45 (50 mg) was dissolved in dichloromethane (2 mL) at 25° C., and triethylamine (33 mg, 0.33 mmol), o-chlorobenzoyl chloride (50% wt ethyl acetate solution, 0.79 mL) were sequentially added thereto. The reaction mixture was stirred for 1 hour under argon atmosphere at 25° C., added with 4-aminobutanol (0.5 mL), continued to stir for 15 minutes at 25° C., added with dichloromethane (30 mL) to dilute, washed with water (20 mL×2), washed with saturated sodium chloride aqueous solution (20 mL), dried over anhydrous sodium sulfate, and filtered. The filtrate was concentrated under reduced pressure to remove the organic solvent to obtain the crude product of Intermediate I-46. The crude product was directly used in the next reaction step without purification.

LC-MS (ESI) $[M+H]^+$ 580.2.

Reference Example 47: Preparation of Intermediate I-47

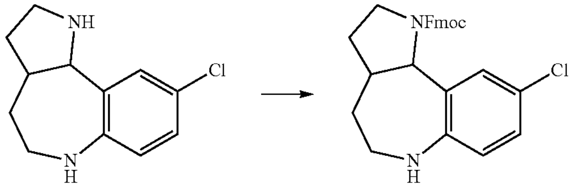

I-7 I-47

Intermediate I-7 (7.30 g, 32.89 mmol) and triethylamine (10.10 g, 100.00 mmol) were dissolved in anhydrous dichloromethane (100 mL) at 25° C. The mixture was slowly added with 9-fluorenylmethyl chloroformate (12.73 g, 49.33 mmol) in an ice-water bath under argon protection and stirred at 25° C. for 16 hours. The reaction mixture was concentrated under reduced pressure at room temperature, slurried with petroleum ether, and filtered. The filter cake was washed with water (20 mL), and dried under reduced pressure to obtain intermediate I-47.

LC-MS (ESI) $[M+H]^+$ 444.8.

Reference Example 48: Preparation of Intermediates I-48A and I-48B

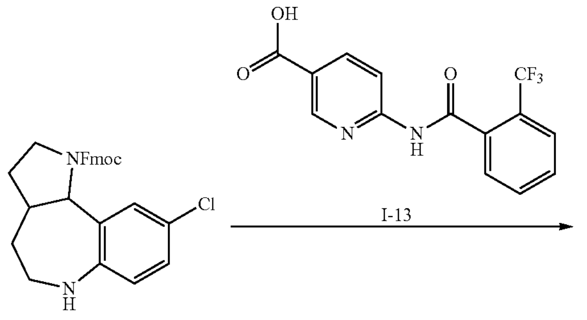

I-47

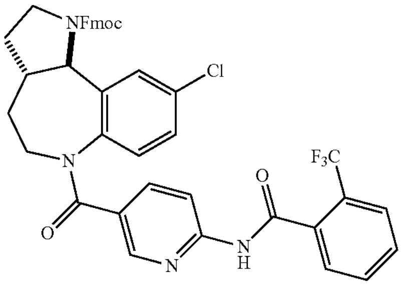

I-48A (trans)

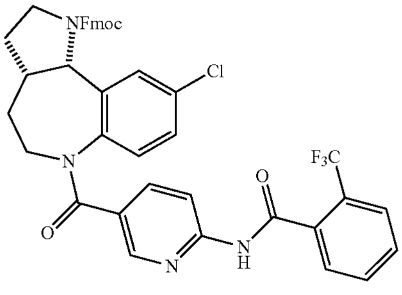

I-48B (cis)

Intermediate I-47 (4.70 g, 10.58 mmol) was dissolved in anhydrous tetrahydrofuran (35 mL) at 25° C., and the mixture was sequentially added with pyridine (8.37 g, 106.00 mmol), intermediate I-13 (4.92 g, 15.87 mmol), and propylphosphonic anhydride (50% wt ethyl acetate solution, 20.00 g, 31.74 mmol), stirred overnight at 65° C. under argon atmosphere. After cooling, the reaction mixture was concentrated to remove most of the tetrahydrofuran, diluted with ethyl acetate (150 mL), sequentially washed with 1 N hydrochloric acid (100 mL×2), washed with saturated sodium bicarbonate aqueous solution (100 mL×3), washed with water (100 mL), washed with saturated sodium chloride aqueous solution (100 mL), dried over anhydrous sodium sulfate, and filtered. The filtrate was concentrated under reduced pressure to remove the organic solvent to obtain a crude product. The crude product was purified by silica gel chromatography to obtain intermediate I-48A (Rt=1.541 min) and intermediate I-48B (Rt=1.508 min).

LCMS analysis method: Chromatographic column: Waters aquity UPLC CSH 2.1×50 mm, 1.7 μm Mobile phase: A: water (0.01% trifluoroacetic acid) B: acetonitrile (0.01% trifluoroacetic acid)

Elution gradient: 5% to 95% B, 0.7 minutes; 95% B, 0.8 minutes; then 5% B, 0.5 minutes Flow rate: 1.0 mL/min Chromatographic column temperature: 60° C.

Mass spectrum scanning range: 100 to 1000

Intermediate I-48A (Rt=1.541 min) LC-MS (ESI) $[M+H]^+$ 737.3.

Intermediate I-48B (Rt=1.508 min) LC-MS (ESI) $[M+H]^+$ 737.3.

Reference Example 49: Preparation of Intermediate I-49

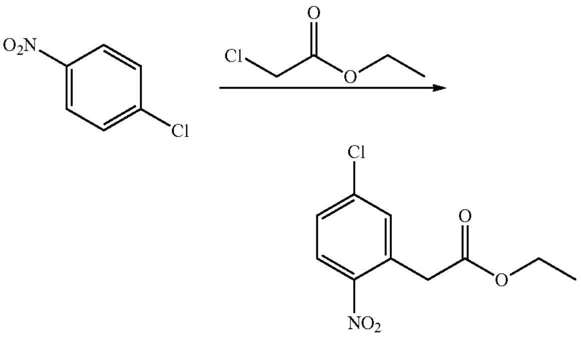

I-49

To a solution of p-chloronitrobenzene (10.00 g, 63.47 mmol) in N,N-dimethylformamide (300 mL) was added potassium tert-butoxide (17.81 g, 158.68 mmol) at −5° C., and the mixture was stirred for 30 minutes and then added with ethyl chloroacetate (8.56 g, 69.82 mmol). The reaction mixture was stirred at −5° C. for 1 hour under nitrogen atmosphere, poured into water (1000 mL), extracted with ethyl acetate (200 mL×4). The organic phases were combined, washed with saturated brine (800 mL×3), dried over anhydrous sodium sulfate, and filtered. The filtrate was concentrated under reduced pressure to remove the organic solvent to obtain a crude product. The crude product was purified by silica gel chromatography to obtain Intermediate I-49.

LC-MS (ESI) $[M+H]^+$ 244.0.

Reference Example 50: Preparation of Intermediate I-50

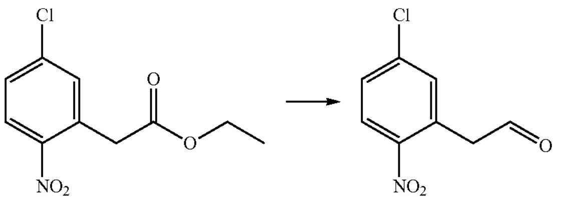

I-49 I-50

To a solution of Intermediate I-49 (12.00 g, 49.25 mmol) in ether (200 mL) was added diisobutylaluminum hydride (1.5 M in THF, 65.67 mL, 98.50 mmol) under nitrogen atmosphere at −78° C., and the reaction mixture was stirred at −78° C. for 1 hour. The reaction mixture was warmed to 0° C., added dropwise with water (4 mL) while stifling, then added with 15% sodium hydroxide aqueous solution (4 mL), and finally added with water (10 mL), warmed to room temperature and stirred for 15 minutes. An appropriate amount of anhydrous sodium sulfate was added thereto, and the reaction mixture was stirred for 15 minutes, and then filtered. The filtrate was concentrated under reduced pressure to remove the organic solvent to obtain intermediate I-50.

LC-MS (ESI) $[M+H]^+$ 200.0.

Reference Example 51: Preparation of Intermediate I-51

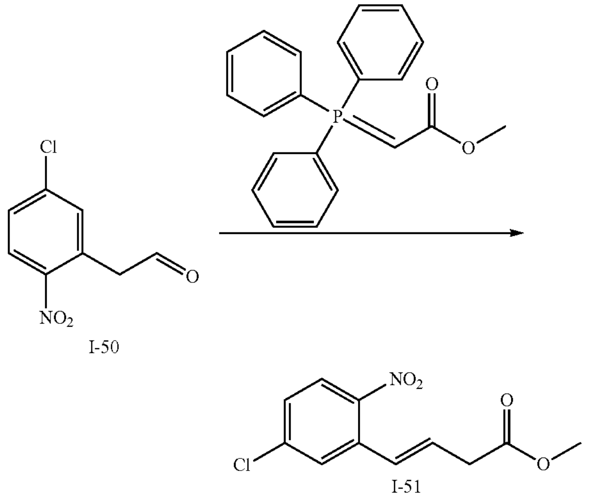

I-50

I-51

To a solution of Intermediate I-50 (7.20 g, 36.07 mmol) in toluene (200 mL) was added methyl (triphenylphosphoranylidene)acetate (12.06 g, 32.07 mmol) at 25° C. The reaction mixture was stirred at 110° C. for 3 hours under nitrogen atmosphere. The reaction mixture was cooled to room temperature and concentrated under reduced pressure to remove the organic solvent to obtain a crude product. The crude product was purified by silica gel chromatography to obtain Intermediate I-51.

Reference Example 52: Preparation of Intermediate I-52

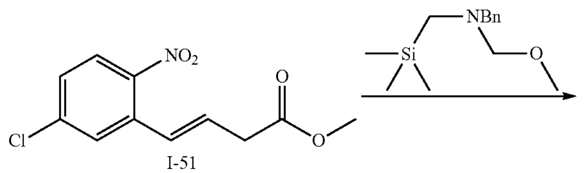

I-51

-continued

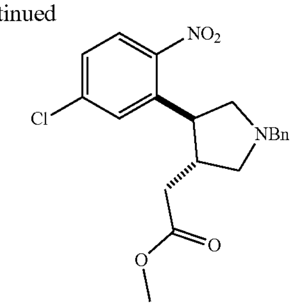

I-52

To a solution of Intermediate I-51 (7.70 g, 30.12 mmol) in dichloromethane (150 mL) was added trifluoroacetic acid (10 mL) at 25° C., and then N-(methoxymethyl)-N-(trimethylsilylmethyl)benzylamine (20.34 g, 85.66 mmol) was added dropwise thereto, and the reaction mixture was stirred at 25° C. for 12 hours, and concentrated under reduced pressure to remove the organic solvent to obtain a crude product. The crude product was purified by silica gel chromatography to obtain Intermediate I-52.

LC-MS (ESI) $[M+H]^+$ 389.2.

Reference Example 53: Preparation of Intermediate I-53

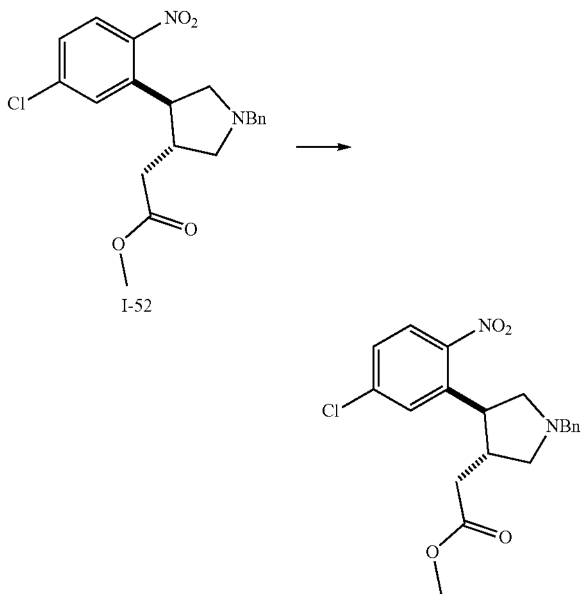

I-52

I-53

To a mixture of Intermediate I-52 (2.8 g, 7.20 mmol) and ammonium chloride (3.08 g, 57.61 mmol) in methanol (60 mL)/water (20 mL) was added zinc powder (2.35 g, 36.00 mmol) at 25° C. The reaction mixture was stirred at 70° C. for 12 hours under nitrogen atmosphere. The reaction mixture was cooled to room temperature, and filtered, and the filtrate was concentrated under reduced pressure, and purified by silica gel chromatography to obtain Intermediate I-53.

LC-MS (ESI) $[M+H]^+$ 359.2.

Reference Example 54: Preparation of Intermediate I-54

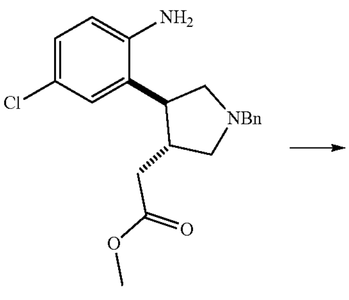

I-53

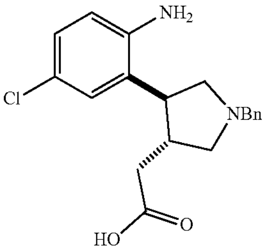

I-54

To a mixture of Intermediate I-53 (2.30 g, 6.41 mmol) in tetrahydrofuran (10 mL)/methanol (10 mL)/water (10 mL) was added potassium hydroxide (1.08 g, 19.29 mmol) at 25° C. The reaction mixture was stirred at 25° C. for 12 hours under nitrogen atmosphere. The reaction mixture was adjusted to acidic (pH=5 to 6) with 1 N hydrochloric acid and extracted with ethyl acetate (30 mL×4). The organic phases were combined, washed with saturated brine (100 mL), dried over anhydrous sodium sulfate, and filtered. The filtrate was concentrated under reduced pressure to remove the organic solvent to obtain Intermediate I-54.

LC-MS (ESI) $[M+H]^+$ 345.2.

Reference Example 55: Preparation of Intermediate I-55

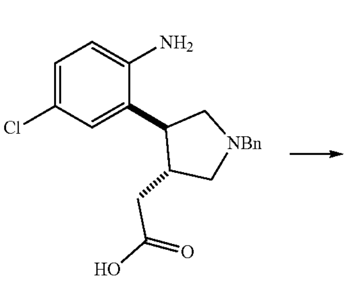

I-54

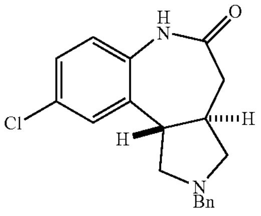

I-55

To a solution of Intermediate I-54 (2.00 g, 5.80 mmol) in dichloromethane (60 mL) was added N,N-diisopropylethylamine (2.25 g, 17.40 mmol) at 25° C., and then O-(benzotriazol-1-yl)-N,N,N',N'-tetramethyluronium tetrafluoroborate (3.72 g, 11.6 mmol) was added thereto. The reaction mixture was stirred at 25° C. for 12 hours under nitrogen atmosphere, and concentrated under reduced pressure to remove the organic solvent to obtain a crude product. The crude product was purified by silica gel chromatography to obtain Intermediate I-55.

LC-MS (ESI) $[M+H]^+$ 327.2.

Reference Example 56: Preparation of Intermediate I-56

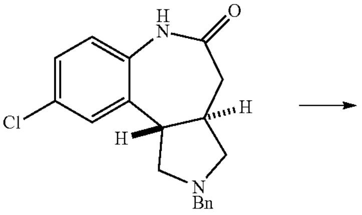

I-55

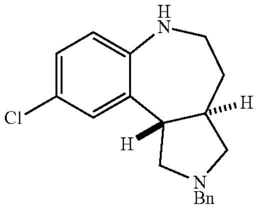

I-56

To a solution of Intermediate I-55 (1.78 g, 5.45 mmol) in tetrahydrofuran (30 mL) was added lithium aluminum hydride (27.23 mL, 27.23 mmol, 1 M in THF) in an ice-water bath under nitrogen atmosphere, and the reaction mixture was stirred at 0° C. for 1 hour, sequentially added with water (4 mL), 15% sodium hydroxide solution (4 mL), and water (10 mL) while stirring, and filtered after stirring for 15 minutes. The filtrate was extracted with ethyl acetate (30 mL×4). The organic phases were combined, washed with saturated brine (100 mL), dried over anhydrous sodium sulfate, and filtered. The filtrate was concentrated under reduced pressure to remove the organic solvent to obtain a crude product. The crude product was purified by silica gel chromatography to obtain Intermediate I-56.

Reference Example 57: Preparation of Intermediate I-57

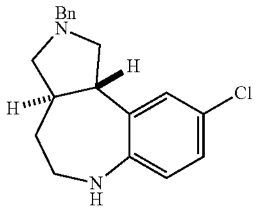

I-56

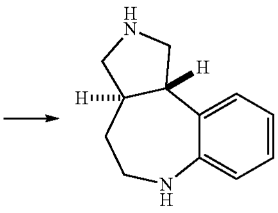

I-57

To a 100 mL high pressure reactor was added Intermediate I-56 (250 mg, 0.799 mmol), palladium carbon (10%, water content of 50%, 200 mg), and methanol (20 mL), and the reaction mixture was replaced with hydrogen twice, stirred overnight at room temperature under hydrogen atmosphere (1 MPa). The mixture was filtered, and the filtrate was concentrated under reduced pressure to obtain Intermediate I-57.

LC-MS (ESI) $[M+H]^+$ 189.1.

Reference Example 58: Preparation of Intermediate I-58

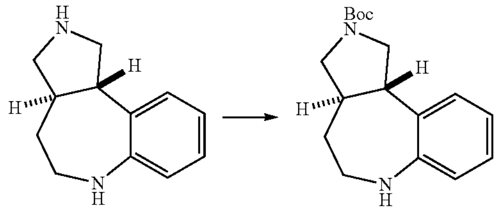

I-57 I-58

Intermediate I-57 (110 mg, 0.584 mmol) and triethylamine (295 mg, 2.92 mmol) were mixed in dichloromethane (5 mL), and di-tert-butyl dicarbonate (153 mg, 0.701 mmol) was added thereto at room temperature. The reaction mixture was stirred at room temperature for 2 hours. The mixture was concentrated and purified by silica gel chromatography to obtain Intermediate I-58.

LC-MS (ESI) $[M+H]^+$ 289.2.

Reference Example 59: Preparation of Intermediate I-59

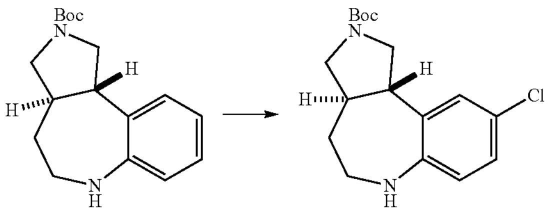

I-58 I-59

Intermediate I-58 (120 mg, 0.416 mmol), copper chloride dihydrate (213 mg, 1.25 mmol), and lithium chloride (53 mg, 1.25 mmol) were dissolved in ethanol (5 mL) at room temperature. The reaction mixture was heated to 80° C., stirred for 6 hours, then cooled to room temperature, and concentrated under reduced pressure to remove the solvent. The residue was diluted with ethyl acetate (10 mL), poured into water (50 mL), added with ammonia water (2 mL), and extracted with ethyl acetate (10 mL×4). The organic phases were combined, washed with saturated brine (10 mL), dried over anhydrous sodium sulfate, and filtered. The filtrate was concentrated under reduced pressure to remove the organic solvent to obtain a crude product. The crude product was purified by silica gel chromatography to obtain Intermediate I-59.

LCMS (ESI) $[M+H+MeCN]^+$ 364.3.

Reference Example 60: Preparation of Intermediate I-60

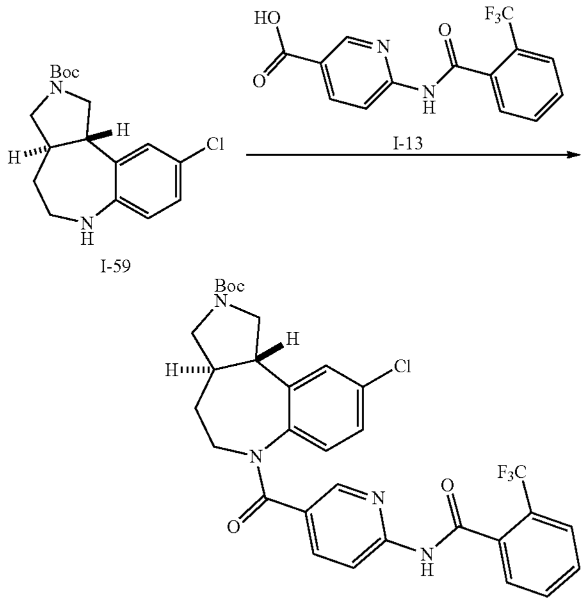

I-13

I-59

I-60

Intermediate I-13 (38.5 mg, 0.124 mmol) was dissolved in N,N-dimethylacetamide (2 mL) at room temperature, and the mixture was cooled to 0° C., and added with thionyl chloride (14.8 mg, 0.124 mmol) under argon atmosphere. The reaction mixture was stirred at room temperature for 1 hour, added with Intermediate I-59 (20.0 mg, 0.062 mmol), and continued to stir at room temperature for 16 hours. The reaction mixture was poured into saturated sodium bicarbonate aqueous solution (20 mL) and extracted with ethyl acetate (5 mL×3). The organic phases were combined, washed with saturated brine (10 mL), dried over anhydrous sodium sulfate, and filtered. The filtrate was concentrated under reduced pressure to remove the organic solvent to obtain a crude product. The crude product was purified by silica gel chromatography to obtain Intermediate I-60.

LC-MS (ESI) $[M+H]^+$ 615.1.

PREPARATION OF EXAMPLES

Example 1: Preparation of Compound 1

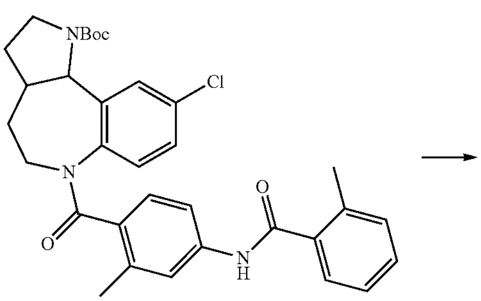

I-11

-continued

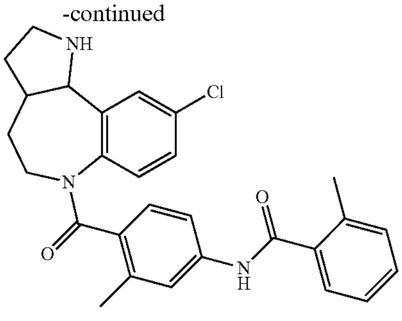

Compound 1

Intermediate I-11 (38 mg, 0.066 mmol) was dissolved in a solution of hydrogen chloride in methanol (3 M, 2 mL) at 25° C. The reaction mixture was stirred at room temperature for 1 hour, concentrated to dryness, and purified by preparative HPLC (formic acid system) to obtain compound 1.

LC-MS (ESI) $[M+H]^+$ 474.2.

$^1H$ NMR (400 MHz, DMSO-$d_6$) δ 10.42-10.23 (m, 1H), 7.82-7.18 (m, 7H), 7.09 (dd, J=8.3, 2.5 Hz, 1H), 6.90-6.43 (m, 2H), 4.94-4.72 (m, 1H), 4.30 (s, 1H), 3.15 (m, 3H), 2.73-2.62 (m, 1H), 2.43-2.27 (m, 6H), 2.27-1.98 (m, 2H), 1.75 (m, 3H).

Example 2: Preparation of Compound 2

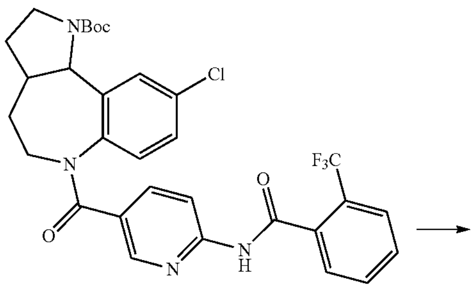

I-14

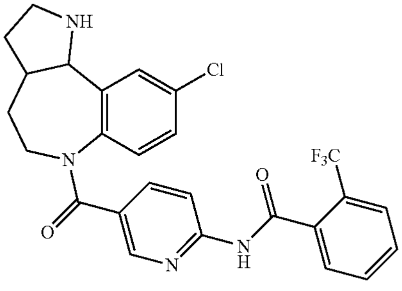

Compound 2

Intermediate I-14 (30 mg, 0.049 mmol) was dissolved in a solution of hydrogen chloride in methanol (3 M, 3 mL) at 25° C. The reaction mixture was stirred at room temperature for 1 hour, concentrated to dryness, and purified by preparative HPLC (formic acid system) to obtain compound 2.

LC-MS (ESI) $[M+H]^+$ 515.2.

$^1H$ NMR (400 MHz, DMSO-$d_6$) δ 11.18 (s, 1H), 8.10-7.95 (m, 2H), 7.88-7.54 (m, 6H), 7.25-7.06 (m, 1H), 6.95 (d, J=8.4 Hz, 1H), 4.89 (d, J=13.5 Hz, 1H), 4.39 (s, 1H), 3.17 (s, 2H), 2.73-2.67 (m, 1H), 2.54 (m, 1 H), 2.27-2.01 (m, 2H), 1.85 (m, 2H), 1.67 (m, 1H).

Example 3: Preparation of Compounds 3A and 3B

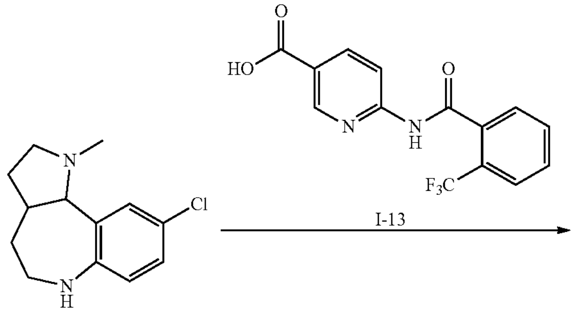

I-16

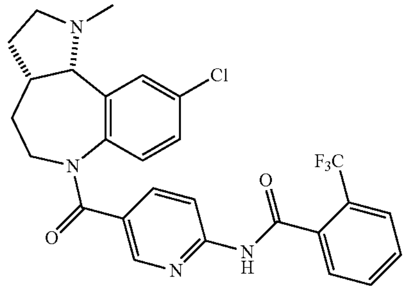

+

Compound 3A

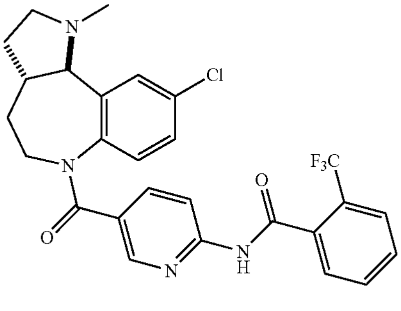

Compound 3B

Intermediate I-16 (70 mg, 0.30 mmol) was dissolved in tetrahydrofuran (1 mL) at 25° C. The mixture was added with pyridine (0.79 mL, 10 mmol), propylphosphonic anhydride (50% wt ethyl acetate solution, 0.79 mL), and Intermediate I-7 (101 mg, 0.33 mmol), sealed in a microwave tube, and stirred at 65° C. overnight. After cooling, the reaction mixture was concentrated to dryness under reduced pressure, dissolved in ethyl acetate (50 mL), washed with water (20 mL×2), washed with saturated brine (20 mL), dried over anhydrous sodium sulfate, and filtered, and the filtrate was concentrated under reduced pressure to obtain a crude product. The crude product was purified by preparative HPLC (formic acid system) to obtain compound 3A (Rt=1.023 min) and compound 3B (Rt=1.039 min).

LCMS analysis method: Chromatographic column: Infinitylab Poroshell 120 EC-C18 3.0×30 mm, 1.9 μm Mobile phase: A: water (0.01% trifluoroacetic acid) B: acetonitrile (0.01% trifluoroacetic acid)

Elution gradient: 5% to 95% B, 0.7 minutes; 95% B, 0.8 minutes; then 5% B, 0.5 minutes Flow rate: 1.2 mL/min Chromatographic column temperature: 40° C.

Mass spectrum scanning range: 100 to 1000

Compound 3A (Rt=1.023 min)

LC-MS (ESI) $[M+H]^+$ 529.2.

$^1H$ NMR (400 MHz, DMSO-$d_6$) δ 8.15-7.95 (m, 2H), 7.92-7.34 (m, 6H), 7.15-6.95 (m, 1H), 6.87-6.60 (m, 1H), 5.01 (m, 1H), 3.55-3.35 (m, 2H), 2.80-2.32 (m, 5H), 2.28-1.83 (m, 4H), 1.63 (m, 1H).

Compound 3B (Rt=1.039 min)

LC-MS (ESI) $[M+H]^+$ 529.2.

$^1H$ NMR (400 MHz, DMSO-$d_6$) δ 8.17-7.90 (m, 2H), 7.85-7.54 (m, 6H), 7.20-7.00 (m, 1H), 6.90-6.60 (m, 1H), 4.70-4.50 (m, 1H), 4.15 (m, 1H), 3.98 (d, J=10.6 Hz, 1H), 2.80-2.45 (m, 5H), 2.35-2.20 (m, 1H), 2.10-1.73 (m, 3H), 1.59-1.37 (m, 1H).

Example 4: Preparation of Compound 4

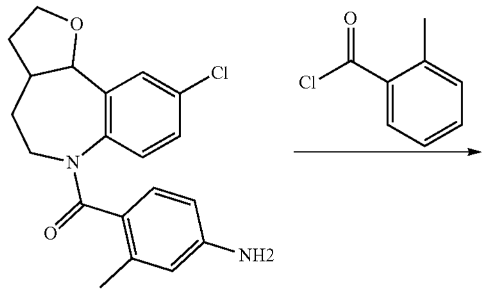

I-26

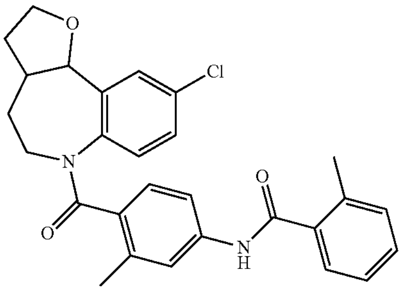

Compound 4

Intermediate I-26 (38 mg, 0.11 mmol) was dissolved in dichloromethane (2 mL) at 25° C. Triethylamine (55 mg, 0.55 mmol), o-toluyl chloride (34 mg, 0.22 mmol) were sequentially added thereto. The reaction mixture was stirred at room temperature for 1 hour, added with methanol (1 mL) to quench, concentrated to dryness under reduced pressure, and purified by preparative HPLC (formic acid system) to obtain compound 4.

LC-MS (ESI) $[M+H]^+$ 475.2.

$^1H$ NMR (400 MHz, DMSO-$d_6$) δ 10.41-10.23 (m, 1H), 7.80-7.58 (m, 1H), 7.56-7.17 (m, 6H), 7.08 (dd, J=8.4, 2.6 Hz, 1H), 6.78 (m, 2H), 4.96-4.80 (m, 1H), 4.75 (d, J=7.8 Hz, 1H), 4.14-3.88 (m, 2H), 2.73-2.61 (m, 1H), 2.45-2.30 (m, 6H), 2.30-2.03 (m, 2H), 1.84 (m, 3H).

Example 5: Preparation of Compound 5

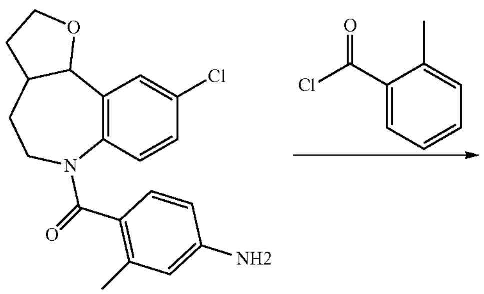

I-29

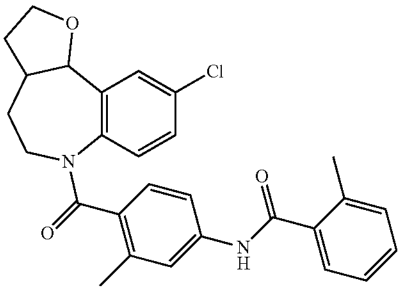

Compound 5

Intermediate I-29 (26 mg, 0.073 mmol) was dissolved in dichloromethane (2 mL) at 25° C. Triethylamine (55 mg, 0.55 mmol), o-toluyl chloride (34 mg, 0.22 mmol) were sequentially added thereto. The reaction mixture was stirred at room temperature for 1 hour, added with methanol (1 mL) to quench, concentrated to dryness under reduced pressure, and purified by preparative HPLC (formic acid system) to obtain compound 5.

LC-MS (ESI) $[M+H]^+$ 475.2.

$^1H$ NMR (400 MHz, DMSO-$d_6$) δ 10.24 (s, 1H), 7.81-7.55 (m, 1H), 7.55-6.99 (m, 7H), 6.76 (dd, J=33.3, 8.3 Hz, 2H), 5.37 (d, J=9.1 Hz, 1H), 4.25-3.90 (m, 2H), 3.79 (m, 1H), 2.70-2.58 (m, 1H), 2.35 (m, 7H), 2.14-1.95 (m, 2H), 1.28 (m, 1H), 1.00-0.77 (m, 1H).

Example 6: Preparation of Compound 6

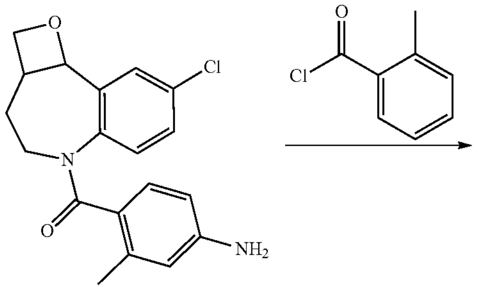

I-35

-continued

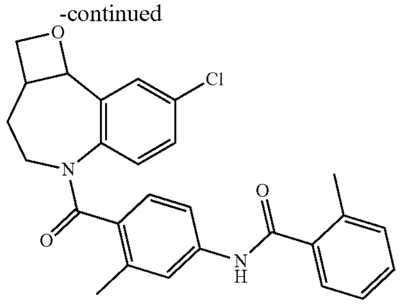

Compound 6

Intermediate I-35 (90 mg, 0.26 mmol) was dissolved in dichloromethane (10 mL) at room temperature, and o-toluoyl chloride (60.7 mg, 0.39 mmol) and triethylamine (79.6 mg, 0.79 mmol) were sequentially added thereto. The reaction mixture was stirred at room temperature for 1 hour, diluted with water (10 mL), and extracted with dichloromethane (20 mL×2). The organic phases were combined, washed with saturated sodium chloride aqueous solution (30 mL×2), dried over anhydrous sodium sulfate, and filtered. The filtrate was concentrated under reduced pressure to remove the organic solvent to obtain a crude product. The crude product was sequentially purified by silica gel chromatography and preparative HPLC (formic acid system) to obtain compound 6.

LC-MS (ESI) $[M+H]^+$ 461.2.

$^1$H NMR (400 MHz, DMSO-$d_6$) δ 10.41-10.22 (s, 1H), 7.75-7.66 (m, 1H), 7.53-7.17 (m, 6H), 7.09-6.79 (m, 3H), 5.87-5.65 (m, 1H), 4.90-4.87 (m, 1H), 4.72-4.68 (m, 1H), 4.42-4.39 (m, 1H), 2.89-2.76 (m, 1H), 2.67-2.55 (m, 1H), 2.39-2.33 (m, 6H), 2.20-2.09 (m, 1H), 1.82-1.80 (m, 1H).

Example 7: Preparation of Compound 7

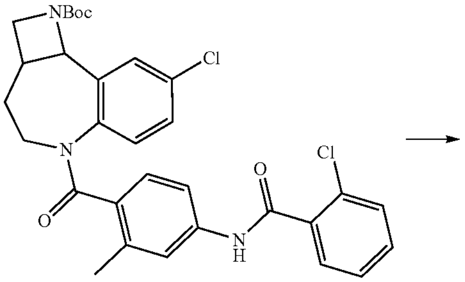

I-46

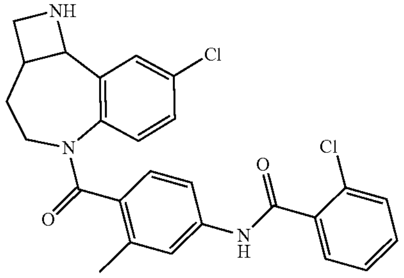

Compound 7

Intermediate I-46 (40 mg, 0.069 mmol) was dissolved in a solution of trifluoroacetic acid in dichloromethane (1/10, 3 mL) at 25° C. The reaction mixture was stirred at room temperature for 1 hour and then poured into cold saturated sodium bicarbonate aqueous solution (20 mL), and extracted with dichloromethane/methanol (10/1, 20 mL×2). The organic phases were combined, washed with water (20 mL), and concentrated under reduced pressure. The residue was purified by preparative HPLC (ammonium bicarbonate system) to obtain compound 7.

LC-MS (ESI) $[M-H]^+$ 477.80.

$^1$H NMR (400 MHz, DMSO-$d_6$) δ 10.67-10.35 (m, 1H), 7.74-7.24 (m, 7H), 7.22-6.95 (m, 2H), 6.82-6.76 (m, 1H), 4.95-4.50 (m, 2H), 3.47 (m, 1H), 3.18 (t, J=6.3 Hz, 1H), 2.99-2.70 (m, 1H), 2.42-2.30 (m, 3H), 2.04-1.54 (m, 2H), 1.15 (t, J=7.0 Hz, 1H), 1.04-0.95 (m, 1H).

Example 8: Preparation of Compound 8

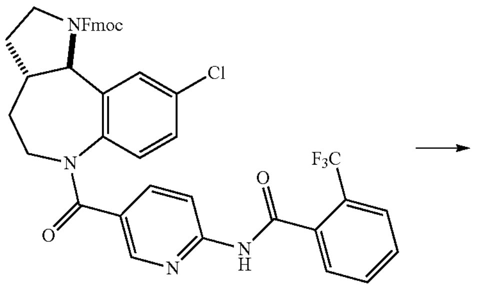

I-48A (trans)

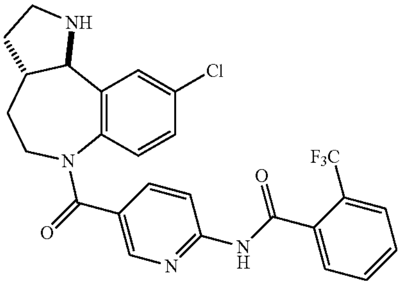

Compound 8 (trans)

Intermediate I-48A (14 mg, 0.019 mmol) was dissolved in N,N-dimethylformamide (3 mL) at 25° C., and the mixture was added with pyrrolidine (35.50 mg, 0.50 mmol), and stirred at 25° C. for 1 hour. The reaction mixture was added ethyl acetate (20 mL) to dilute, washed with water (10 mL×3), dried over anhydrous sodium sulfate, and filtered. The filtrate was concentrated under reduced pressure and purified by C18 reverse phase chromatography (formic acid system) to obtain compound 8.

LC-MS (ESI) $[M+H]^+$ 515.2.

$^1$H NMR (400 MHz, DMSO-$d_6$) δ 11.18 (s, 1H), 8.13-7.90 (m, 2H), 7.88-7.52 (m, 6H), 7.09 (dd, J=8.3, 2.7 Hz, 1H), 6.89 (d, J=8.3 Hz, 1H), 4.90 (dt, J=13.7, 3.3 Hz, 1H), 4.14 (d, J=9.2 Hz, 1H), 3.80-3.35 (m, 1 H), 3.15-3.03 (m, 1H), 3.03-2.92 (m, 1H), 2.66 (t, J=12.7 Hz, 1H), 2.09 (dd, J=12.1, 4.1 Hz, 2H), 1.86-1.64 (m, 2H), 1.64-1.51 (m, 1H).

Example 9: Preparation of Compound 9

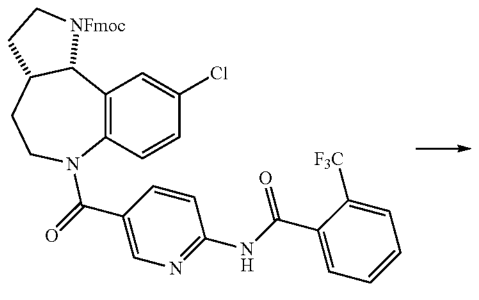

I-48B (cis)

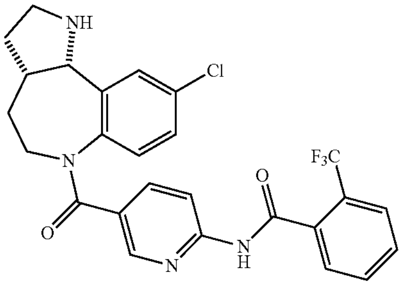

Compound 9 (cis)

Intermediate I-48B (4.00 mg, 0.0054 mmol) was dissolved in N,N-dimethylformamide (3 mL) at 25° C., and the mixture was added with pyrrolidine (35.50 mg, 0.50 mmol), and stirred at 25° C. for 1 hour. The reaction mixture was added ethyl acetate (20 mL) to dilute, washed with water (10 mL×3), dried over anhydrous sodium sulfate, and filtered. The filtrate was concentrated under reduced pressure and purified by C18 reverse phase chromatography (formic acid system) to obtain compound 9.

LC-MS (ESI) $[M+H]^+$ 515.2.

$^1H$ NMR (400 MHz, DMSO-$d_6$) δ 11.19 (s, 1H), 8.13-7.90 (m, 2H), 7.86-7.58 (m, 6H), 7.12 (dd, J=8.2, 2.6 Hz, 1H), 6.93-6.74 (m, 1H), 4.70 (d, J=9.4 Hz, 1H), 3.99 (td, J=13.4, 3.5 Hz, 1H), 3.37 (m, 1H), 3.11-2.90 (m, 2H), 2.47-2.28 (m, 1H), 2.06-1.85 (m, 2H), 1.20-0.78 (m, 3H).

Example 10: Preparation of Compound 10A and Compound 10B

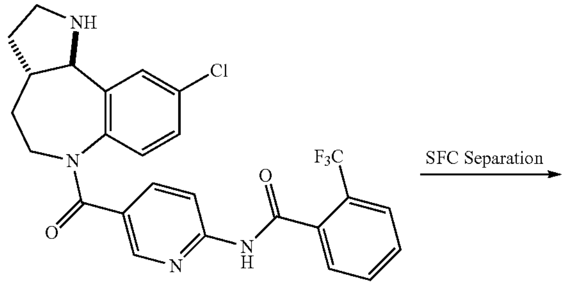

Compound 8 (trans)

-continued

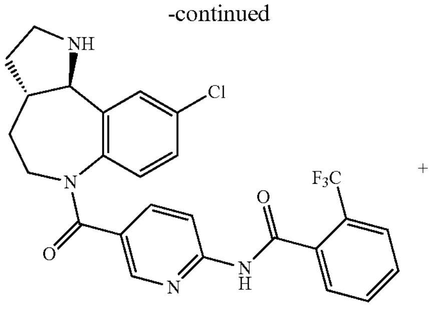

Compound 10A

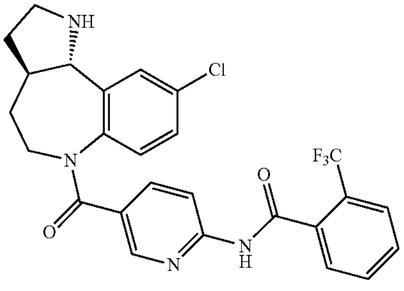

Compound 10B

Compound 8 was resolved by SFC to obtain compound 10A (Rt=1.424 min) and compound 10B (Rt=1.993 min).

Chiral Resolution Method

Instrument: MG II preparative SFC (SFC-14)

Chromatographic column: ChiralPak AD, 250×30mm I.D., 10 μm

Mobile phase: A: carbon dioxide B: ethanol (0.1% ammonia water)

Elution gradient: 35% B

Flow rate: 80 mL/min

Back pressure: 100 bar

Column temperature: 38° C.

Detection wavelength: 220 nm

Cycle time: about 8 minutes

Chiral Analysis Method:

Instrument: Waters $UPC_2$ analytical SFC (SFC-H)

Chromatographic column: ChiralPak AD, 150×4.6mm I.D., 3 μm

Mobile phase: A: carbon dioxide B: ethanol (0.05% diethylamine)

Elution gradient: 40% B

Flow rate: 2.5 mL/min

Back pressure: 1500 psi

Column temperature: 35° C.

Detection wavelength: 220 nm

Compound 10A

Rt=1.424 min

LC-MS (ESI) $[M+H]^+$ 515.2.

$^1H$ NMR (400 MHz, DMSO-$d_6$) δ 11.18 (s, 1H), 8.30-7.88 (m, 2H), 7.88-7.55 (m, 6H), 7.10 (dd, J=8.4, 2.7 Hz, 1H), 6.89 (d, J=8.3 Hz, 1H), 4.90 (dt, J=13.5, 3.2 Hz, 1H), 4.14 (d, J=9.2 Hz, 1H), 3.40-3.39 (m, 1 H), 3.13-2.90 (m, 2H), 2.66 (t, J=12.3 Hz, 1H), 2.16-2.05 (m, 2H), 1.87-1.49 (m, 3H).

Compound 10B

Rt=1.993 min

LC-MS (ESI) $[M+H]^+$ 515.0.

$^1H$ NMR (400 MHz, DMSO-$d_6$) δ 11.18 (s, 1H), 8.12-7.89 (m, 2H), 7.87-7.59 (m, 6H), 7.18-7.03 (m, 1H), 6.90 (d, J=8.4 Hz, 1H), 4.98-4.83 (m, 1H), 4.17 (m, 1H), 3.11-2.92 (m, 2H), 2.73-2.60 (m, 1H), 2.15-2.02 (m, 2H), 1.86-1.66 (m, 2H), 1.64-1.52 (m, 1H).

Example 11: Preparation of Compound 11

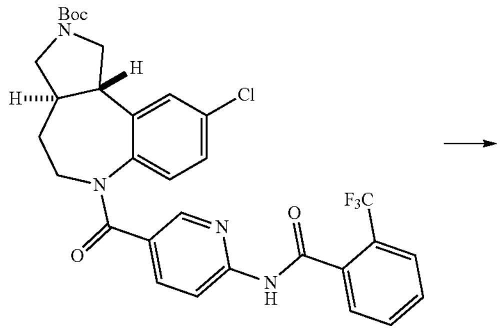

I-60

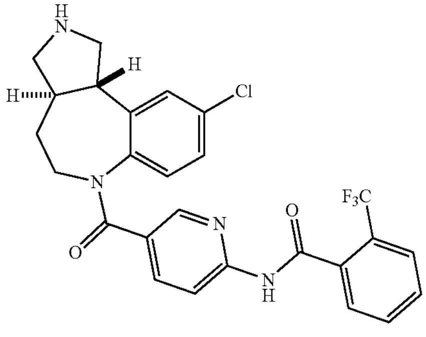

Compound 11

Intermediate I-60 (15.0 mg, 0.0244 mmol) was dissolved in dichloromethane (0.5 mL) at room temperature, and trifluoroacetic acid (0.5 mL) was added dropwise thereto while stirring at room temperature, and the reaction mixture was stirred at room temperature for 2 hours. The mixture was concentrated and purified by preparative HPLC (ammonia water system) to obtain compound 11.

LC-MS (ESI) $[M+H]^+$ 515.2.

$^1H$ NMR (400 MHz, DMSO-$d_6$) δ 11.17 (s, 1H), 8.10-7.94 (m, 2H), 7.81 (d, J=7.6 Hz, 1H), 7.78-7.58 (m, 4H), 7.23 (d, J=2.4 Hz, 1H), 7.12 (dd, J=8.6, 2.4 Hz, 1H), 6.94 (d, J=8.3 Hz, 1H), 4.90 (d, J=13.9 Hz, 1H), 3.77-3.64 (m, 1H), 3.59-3.50 (m, 1H), 3.21 -3.07 (m, 3H), 2.74-2.61 (m, 2H), 2.10-2.01 (m, 1H), 1.84-1.66 (m, 2H).

Experimental Example 1: $IC_{50}$ Test of Inhibition of Compounds on Vasopressin-Induced Activation of Vasopressin Receptor V2R (1) Cell HeLa cell line stably expressing human vasopressin receptor V2R (HeLa-V2R): The cell line was constructed by Shanghai Genechem Co., Ltd. using a lentivirus infection method, and verified via qPCR that human V2R was stably expressed.

(2) Reagent

DMEM cell medium: Brand: Gibco, Item No.: 11995065; Fetal Bovine Serum: Brand: Genetimes, Item No.: FND500; 0.25% Trypsin: Brand: Gibco, Item No.: 25200072; Puromycin Dihydrochloride: Brand: Gibco, Item No.: A1113803; cAMP-GS HIRANGE KIT: Brand: Cisbio, Item No.: 62AM6PEC; IBMX: Brand: Sigma, Item No.: i5879; vasopressin AVP: customized by GL Biochem (Shanghai), Ltd.

(3) Test Method

HeLa-V2R cells were incubated with DMEM medium supplemented with 10% fetal bovine serum under the condition of 37° C. and 5% $CO_2$, and the medium was added with 2 μg/mL puromycin to continuously screen cells expressing V2R. On the day of the experiment, the cells were digested with trypsin, washed twice with the stimulation buffer in the cAMP-GS HIRANGE kit, resuspended, and counted to prepare $1.6\times10^6$ cells/mL, and IBMX was added until a final concentration of 0.5 mM. 5 μL of cell suspension/well was transferred to a 384-well plate. To the corresponding wells were added 2.5 μL of various concentrations of the test compounds (3-fold dilution from 10 μM, 10 concentration gradients) or DMSO (minimum value Min, maximum value Max as a control), respectively. After incubating at room temperature for 30 minutes, the test compound well and the maximum value well were added with 2.5 μL of vasopressin AVP solution until a final concentration of 2.25 nM, and the minimum value well was added with 2.5 μL of the stimulation buffer, and the plate was incubated at 25° C. for 60 minutes. At the same time, cAMP standard samples (3-fold dilution from 5.6 μM, 10 concentration points) were prepared, and 10 μL of cAMP standard samples were transferred to corresponding wells of a 384-well plate. The cAMP-d2 fluorescence and anti-cAMP antibody probes provided in the kit were 20-fold diluted by the lysis buffer in the cAMP-GS HIRANGE kit. To each well of a 384-well plate was sequentially added 5 μL of each diluted reagent. The above mixture in each well was mixed well, centrifuged briefly, incubated at 25° C. for 2 hours, and tested. The sample was tested by the HTRF method with the Envision microplate reader to determine the fluorescence intensity at 615 nm and 665 nm. Each test sample was tested in duplicate, with 32 replicates for both Min and Max, respectively.

(4) Data Processing

The fluorescence intensity ratio $FI_{665/615}$ at the wavelength of 665 nm and 615 nm of the samples in each well was calculated. The logarithm of the concentration of the standard was taken as X, and $FI_{665/615}\times1000$ as the Y value, and the standard curve was obtained by fitting the "log (inhibitor) vs response-variable slope (four parameters)" model in Prism 8.0 software. $FI_{665/615}\times1000$ of the test well was taken as the Y value, and the cAMP concentration corresponding to each sample was calculated in the Prism 8.0 software according to the above standard curve.

% Inhibition (inhibition percentage) calculation formula is as follows:

$$\% \text{ inhibition}=(\overline{Cmax}-Ccmpd)/(\overline{Cmax}-\overline{Cmin})\times100$$

wherein $\overline{Cmax}$ is the average calculated value of cAMP concentration in all maximum wells; $\overline{Cmin}$ is the average calculated value of cAMP concentration in all minimum wells; Ccmpd is the calculated value of cAMP concentration of the test compound.

% Inhibition (inhibition percentage) was taken as the Y value, and the logarithmic value of the compound concentration was taken as the X value, and the $IC_{50}$ was calculated by nonlinear regression with "log(inhibitor) vs response-variable slope (four parameters)" model in Prism 8.0 software, wherein Y=Bottom+(Top−Bottom)/(1+10^((Log $IC_{50}$−X)×Hill Slope)).

The experimental results are shown in Table 1:

TABLE 1

Evaluation of compounds on inhibition of cAMP increase in human cervical cancer cells (Human V2R Hela-Stable cell line OE2)

| Compound number | $IC_{50}$ (nM) | Compound number | $IC_{50}$ (nM) |
|---|---|---|---|
| 1 | 14.65 | 2 | 32.62 |
| 3A | 84.73 | 4 | 7.45 |
| 5 | 61.55 | 6 | 3.85 |
| 7 | 92.68 | 8 | 69.52 |
| 10A | 30.97 | | |

Experimental Example 2: In Vivo Pharmacokinetic Experiment of Compounds of the Present Disclosure In this experimental example, in vivo pharmacokinetic evaluations were performed on mice by intravenous injection and oral administration.

Experimental methods and conditions: Male CD1 mice, 6 to 8 weeks old with free access to food and water, were administered by oral gavage with a dosage of 10 mg/kg (solvent 5% DMSO/10% Solutol/85% Saline). 15 minutes, 30 minutes, 1 hour, 2 hours, 4 hours, 8 hours, 10 hours, 24 hours after administration, blood samples were collected. Each sample was collected in a volume of 150 μL and anticoagulated with heparin sodium, placed on ice after collection, and centrifuged within 1 hour to separate the test plasma. The plasma concentration in plasma was tested by liquid chromatography-tandem mass spectrometry (LC/MS/MS), and pharmacokinetic parameters were calculated using Phoenix WinNonlin software via the measured concentration. Tolvaptan was taken as the reference substance 1, and the experimental results are shown in Table 2.

TABLE 2

Pharmacokinetics of oral administration (10 mg/kg)

| Compound | $T_{1/2}$ (hr) | $C_{max}$ (ng/mL) | $AUC_{0\text{-}inf}$ (ng * hr/mL) | F (%) |
|---|---|---|---|---|
| Compound 10A | 4.44 | 833.03 | 2026.32 | 73.34 |
| Reference substance 1 | 1.58 | 1307 | 1613 | 44 |

Experimental data indicate that the in vivo pharmacokinetics results of oral administration of the compounds of the present disclosure to mice show longer half-life $T_{1/2}$ and higher exposure $AUC_{0\text{-}inf}$ in vivo.

Experimental Example 3: Test of Inhibitory Effect of Compounds on LLC-PK1 Cell Proliferation

(1) Cells

Porcine renal epithelial cell LLC-PK1: purchased from ATCC, Cat #CL-101

(2) Reagents

Medium 199, Gibco (Cat #11150059)

Fetal Bovine Serum (FBS), Australia, Genetimes (Cat #FND500)

Trypsin-EDTA (0.25%), phenol red, Gibco (Cat #25200072)

PBS, pH 7.4, Gibco (Cat #10010031)

DMSO (dimethyl sulfoxide), Sigma (Cat #D8418)

Poly-D-lysine, Gibco (Cat #A3890401)

Vasopressin AVP: Customized by GL Biochem (Shanghai), Ltd.

Verapamil hydrochloride, MCE (Cat #HY-A0064)

AlamarBlue™ HS Cell Viability Reagent, Invitrogen (Cat #A50100)

(3) Test Method

The pathogenesis of polycystic kidney disease is related to the low intracellular calcium ion concentration of renal collecting duct epithelial cells and the cAMP-dependent excessive proliferation of cells. Referring to the research paper published by Tamio Yamaguchi et al. in *The Journal of Biological Chemistry* in 2004, we optimized and carried out the LLC-PK1 proliferation assay of renal epithelial cells to evaluate the inhibiting effects of compounds on vasopressin-induced cell proliferation after reducing the intracellular calcium ion concentration.

LLC-PK1 cells were incubated with M199 medium supplemented with 10% fetal bovine serum under the condition of 37° C. and 5% $CO_2$. On the first day of the experiment, a 96-well plate was coated with 0.01% Poly-D-lysine, then each well of the plate was added with 100 μL of the above mixture. After standing at room temperature for 10 minutes, the mixture in each well was aspirated and air-dried at room temperature for 1 hour, and washed once with 200 μL 1×PBS for further use. LLC-PK1 cells were digested with trypsin, resuspended with serum-free M199 after centrifugation, counted, diluted into $1\times10^5$/mL cell suspension with serum-free M199 medium, and added with FBS until 1% final concentration. To a 96-well plate was transfered 200 μL of cell suspension/well. After the cells were incubated for 24 hours, the supernatant of the formulated solution was aspirated, and the cells were washed once with 200 μL of PBS. Then 160 μL of M199 medium containing 0.05% FBS and 20 μL of 10×Verapamil (final concentration of 5 μM) were sequentially added thereto, and the culture was continued for 24 hours. To the corresponding wells was respectively added 10 μL of various concentrations of the test compound (final concentration starting from 3 μM, 3-fold dilution, 8 concentration gradients) or DMSO (Min, and Max as a control) on the third day. To the test compound well and the maximum value well was added 10 μL of vasopressin AVP solution until a final concentration of 10 nM, and to the minimum value well was added 10 μL of serum-free M199 medium, and each well was continued to incubate for 48 hours. On the fifth day, the culture medium was carefully aspirated. The cells were washed once with 200 μL of PBS. 90 μL of M199 serum-free medium was carefully added thereto, and then 10 μL of Alamarblue reagent was added thereto. The mixture was centrifuged at 300 rpm for 1 minute, incubated at 37° C. for 2 hours, and then tested. SpectraMax instrument was used for the sample test. The excitation light was 560 nm, and the emission light was 595 nm. Each test sample was tested in triplicate, with 6 replicates for both Min and Max, respectively.

(4) Data Processing

The concentration of the compound was taken as the X value, and the average value of the fluorescence intensity of each experimental well sample minus the fluorescence intensity of the background well was taken as the Y value, which represented the number of living cells in the well at the time of testing. The Grouped-Summary data-Separated bar graph in GraphPad Prism 8.0 software was used to make a bar chart for reflecting the dose-effect relationship of different compounds on AVP-induced cell proliferation. Tolvaptan was used as a positive control for qualitatively evaluating the inhibitory effect of the compounds on proliferation: compounds whose overall performance was better than that of Tolvaptan were represented as "+++", those whose performance was close to Tolvaptan were represented as "++", those whose performance was weaker than Tolvaptan were represented as "+", and those with no proliferation inhibition were represented as "−".

Data quality control: S/B was calculated, i.e., the average value of the Max well/the average value of the Min well≥2 was regarded as a QC pass.

Figure 2:
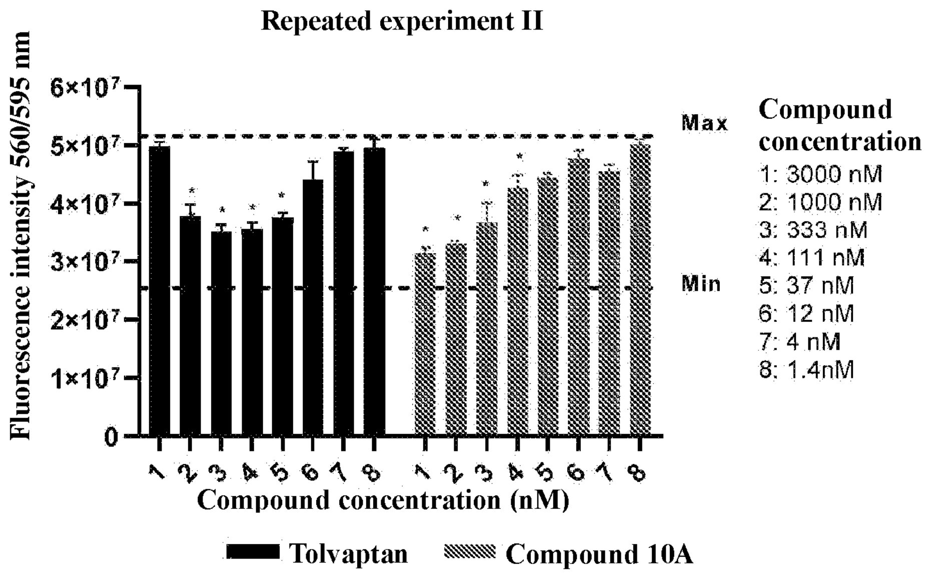
FIG. 2 is a graph of repeated experiment II according to an example of the present disclosure.

The experimental results indicate (see FIG. 1, FIG. 2, and Table 3 below) that in the AVP-induced LLC-PK1 cell proliferation assay, Tolvaptan, as a positive reference, exhibited a high-concentration pro-proliferative hook effect, while compound 1 had no hook effect, showing a dose-response superior to that of Tolvaptan.

TABLE 3

Inhibitory effect of compounds on LLC-PK1 cell proliferation

| Compound | Proliferation inhibition grading: Repeated experiment I | Proliferation inhibition grading: Repeated experiment II |
|---|---|---|
| Reference substance 1 | ++ | ++ |
| Compound 10A | +++ | +++ |

Experimental Example 4: Binding Test of Compounds to V1a, V1b, V2 Receptors

In this experiment, the affinity Ki of compound 1 and reference substance 1 to human V1aR, V1bR, and V2R was tested by a competitive isotope ligand binding experiment.

(1) Cell Membrane

The cells with high expression of human V1a receptor were amplified, collected, washed twice with PBS, resuspended with PBS containing a protease inhibitor, homogenized with a homogenizer at 15000 r/min to break the cells, and centrifuged at 4° C. and 3000 r/min for 15 minutes. The supernatant was collected, centrifuged at 20,000 r/min at 4° C. for 45 minutes. Then the supernatant was discarded to obtain a cell membrane precipitation. Buffer was added to resuspend to measure the protein concentration, aliquoted, and stored at −80° C. The cell membranes of highly expressed human V1b and V2 receptors were purchased from Perkinelmer, USA.

(2) Assay Buffer 50 mM Tris-HCl, pH 7.4
10 mM $MgCl_2$
0.1% BSA
Protease inhibitor mixture (one tablet/50 mL)

(3) Wash Buffer 50 mM Tris-HCl, pH 7.4

(4) Compound Preparation

1. Preparation of A Stock Solution of Compounds 1.59 mg, 1.24 mg, and 1.38 mg of the test compound were taken, respectively, and dissolved in 100% dimethyl sulfoxide until a final concentration of 10 mM. Positive control vasopressin was prepared as a 10 mM stock solution.

2. Preparation of 100×Compounds

The stock solution of the test compound and that of the positive control were diluted to 1 mM (10-fold dilution) and 0.1 mM (100-fold dilution) with DMSO, respectively, and then sequentially subjected to a four-fold dilution with DMSO to the tenth point.

3. Preparation of Cell Membrane Stock Solution

Cell membranes overexpressing human receptors were prepared with assay buffer to 5 mg/mL.

(5) Operating Steps 1. 1 μL of the compound was aspirated from the dilution plate into each well of the 96-well assay plate (the concentration of the test compound in the reaction would be diluted 100-fold). To the control well was added 1 μL of DMSO.
2. 10 mL of membrane solution containing 5 μg/μL was prepared.
3. To the compound assay plate was added the membrane solution from step 2 with a pipette, and each well was added with 89 μL of the membrane solution.
4. The 50 μCi/mL isotope-labeled vasopressin stock solution was diluted with assay buffer to a 10-fold final concentration, and the reaction plate was added with 10 μL/well with a pipette. The final concentrations of the isotope-labeled vasopressin in V1a, V1b, and V2 receptor experiments were 1.5 nM, 0.75 nM, and 1 nM, respectively.
5. The configured test plate was placed at 30° C. and incubated for 60 minutes.
6. The membrane complexes were collected into 0.5% PEI pre-coated GF/B plate with Cell Harvester, washed 3 times with 2 mL of pre-cooled elution buffer at 4° C., and dried at 37° C. for 2 hours.
7. The content of isotope-labeled vasopressin bound to the receptor was measured with a liquid scintillation/luminescence counter.
8. The read data was processed with prism 5, and the dose-effect curve of the compound and the IC50 value of the compound competitively inhibiting the binding of isotope-labeled vasopressin to the receptor were obtained by fitting with the following equation.

Y=Bottom+(Top−Bottom)/(1+10^((X−Log IC50))), wherein: Y is the reading value of the liquid scintillation counter, and X is the logarithmic value of the compound concentration. The affinity of the compound for the receptor, Ki, was calculated from the IC50 value using the following equation: Ki=IC50/(1+([L]/Kd)), wherein [L] is the concentration of isotope-labeled vasopressin in the test, and Kd is the dissociation constant between isotope-labeled vasopressin and the receptor.

The results of the two repeated experiments are shown in Table 4. The binding Ki of vasopressin to the three receptors was close to that reported in the literature, and neither compound 10A nor reference substance 1 bound to the V1b receptor (IC50>10 μM); the binding affinity of compound 10A and reference substance 1 for V2R was higher than that for V1a, with varying degrees of V1a/V2 selectivity.

TABLE 4

Binding affinity of test compounds to V1a, V1b, V2 receptors

| | (nM) | | | | | |
|---|---|---|---|---|---|---|
| | V1aR | | V1bR | | V2R | |
| Compound | N = 1 | N = 2 | N = 1 | N = 2 | N = 1 | N = 2 |
| Compound 10A | 19.71 | 11.14 | >10 μM | >10 μM | 2.1 | 2.76 |
| | 15.4 ± 4.3 | | >10 μM | | 2.4 ± 0.3 | |
| Reference | 23.32 | 20.4 | >10 μM | >10 μM | 0.27 | 0.6 |
| substance 1 | 21.9 ± 1.5 | | >10 μM | | 0.44 ± 0.17 | |
| Vasopressin | 0.37 | 0.27 | 0.15 | 0.27 | 0.75 | 1.2 |
| | 0.32 ± 0.05 | | 0.21 ± 0.06 | | 0.98 ± 0.23 | |

What is claimed is:

1. A compound of formula (I), an optical isomer thereof, or a pharmaceutically acceptable salt thereof, (I)

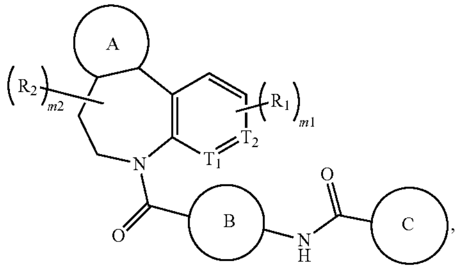

wherein ring A is selected from 4- to 6-membered heterocyclyl and $C_{3-6}$ cycloalkyl, and the 4- to 6-membered heterocyclyl or $C_{3-6}$ cycloalkyl is optionally substituted by 1, 2, or 3 $R_A$;

ring B is selected from phenyl and 5- to 6-membered heteroaryl, and the phenyl or 5- to 6-membered heteroaryl is optionally substituted by 1, 2, or 3 $R_3$;

ring C is selected from phenyl and 5- to 6-membered heteroaryl, and the phenyl or 5- to 6-membered heteroaryl is optionally substituted by 1, 2, or 3 $R_4$;

$T_1$, $T_2$ are each independently selected from N and $C(R_T)$;

$R_1$, $R_2$, $R_3$, $R_A$, $R_T$ are each independently selected from H, F, Cl, Br, I, CN, OH, $NH_2$, $C_{1-6}$ alkyl, and $C_{1-6}$ heteroalkyl, and the $C_{1-6}$ alkyl or $C_{1-6}$ heteroalkyl is optionally substituted by 1, 2, or 3 R;

each $R_4$ is independently selected from H, F, Cl, Br, I, CN, OH, $NH_2$, $C_{1-6}$ alkyl, $C_{1-6}$ alkoxy, $C_{1-6}$ alkylamino, $C_{3-6}$ cycloalkyl, phenyl, and 5- to 6-membered heteroaryl, and the $C_{1-6}$ alkyl, $C_{1-6}$ alkoxy, $C_{1-6}$ alkylamino, $C_{3-6}$ cycloalkyl, phenyl, or 5- to 6-membered heteroaryl is optionally substituted by 1, 2, or 3 $R_{4a}$;

R, $R_{4a}$ are each independently selected from H, F, Cl, Br, I, CN, OH, $NH_2$, $C_{1-6}$ alkyl, $C_{1-6}$ alkoxy, and $C_{1-6}$ alkylamino, and the $C_{1-6}$ alkyl, $C_{1-6}$ alkoxy, and $C_{1-6}$ alkylamino are optionally substituted by 1, 2, or 3 R';

R' is selected from H, F, Cl, Br, I, CN, OH, $NH_2$, and $C_{1-6}$ alkyl;

m1, m2 are each independently selected from 0, 1, or 2;

and when ring A is selected from 4- to 6-membered heterocyclyl, the compound of formula (I) is not selected from

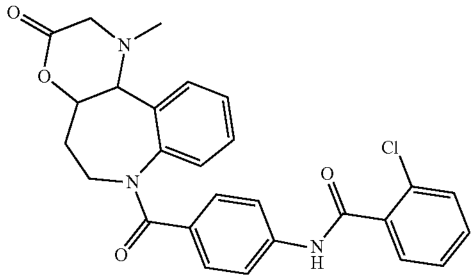

,

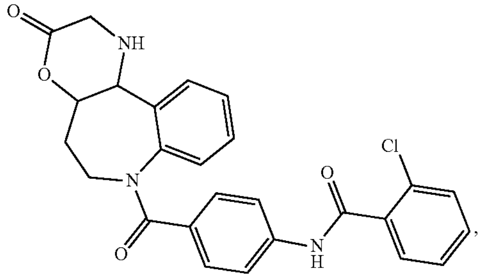

, or

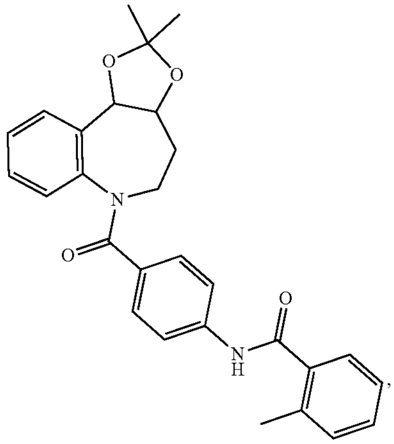

, the 4- to 6-membered heterocyclyl, $C_{1-6}$ heteroalkyl, or 5- to 6-membered heteroaryl comprises 1, 2, 3, or 4 heteroatoms or heteroatom groups independently selected from —O—, —NH—, —S—, —C(═O)—, —C(═O)O—, —S(═O)—, —S(═O)$_2$—, and N.

2. The compound, the optical isomer thereof, or the pharmaceutically acceptable salt thereof according to claim 1, wherein the compound has a structure of formula (II), (II)

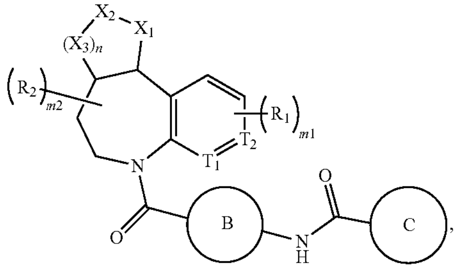

wherein $X_1$, $X_2$, $X_3$ are each independently selected from O, $C(R_A)_2$, and $NR_A$;

ring B is selected from phenyl and 5- to 6-membered heteroaryl, and the phenyl or 5- to 6-membered heteroaryl is optionally substituted by 1, 2, or 3 $R_3$;

ring C is selected from phenyl and 5- to 6-membered heteroaryl, and the phenyl or 5- to 6-membered heteroaryl is optionally substituted by 1, 2, or 3 $R_4$;

$T_1$, $T_2$ are each independently selected from N and $C(R_T)$;

$R_1$, $R_2$, $R_3$, $R_A$, $R_T$ are each independently selected from H, F, Cl, Br, I, CN, OH, $NH_2$, $C_{1-6}$ alkyl, and $C_{1-6}$ heteroalkyl, and the $C_{1-6}$ alkyl or $C_{1-6}$ heteroalkyl is optionally substituted by 1, 2, or 3 R;

each $R_4$ is independently selected from H, F, Cl, Br, I, CN, OH, $NH_2$, $C_{1-6}$ alkyl, $C_{1-6}$ alkoxy, $C_{1-6}$ alkylamino, $C_{3-6}$ cycloalkyl, phenyl, and 5- to 6-membered heteroaryl, and the $C_{1-6}$ alkyl, $C_{1-6}$ alkoxy, $C_{1-6}$ alkylamino, $C_{3-6}$ cycloalkyl, phenyl, or 5- to 6-membered heteroaryl is optionally substituted by 1, 2, or 3 $R_{4a}$;

R, $R_{4a}$ are each independently selected from H, F, Cl, Br, I, CN, OH, $NH_2$, $C_{1-6}$ alkyl, $C_{1-6}$ alkoxy, and $C_{1-6}$ alkylamino, and the $C_{1-6}$ alkyl, $C_{1-6}$ alkoxy, and $C_{1-6}$ alkylamino are optionally substituted by 1, 2, or 3 R';

R' is selected from H, F, Cl, Br, I, CN, OH, $NH_2$, and $C_{1-6}$ alkyl;

m1, m2, n are each independently selected from 0, 1, or 2;

and when $X_1$, $X_3$ are selected from O at the same time, the compound of formula (II) is not selected from

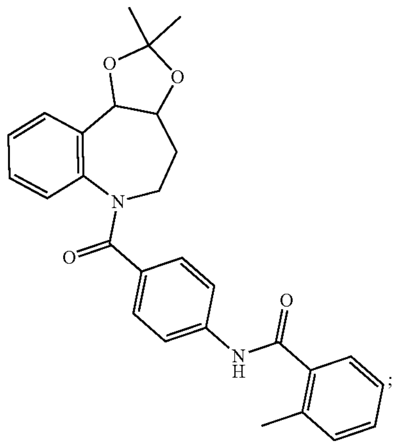 [SMILES: Cc1ccccc1C(=O)Nc1ccc(C(=O)N2CCC3OC(C)(C)OC3c3ccccc32)cc1]

;

the $C_{1-6}$ heteroalkyl or 5- to 6-membered heteroaryl comprises 1, 2, 3, or 4 heteroatoms or heteroatom groups independently selected from —O—, —NH—, —S—, —C(═O)—, —C(═O)O—, —S(═O)—, —$S(═O)_2$—, and N.

3. The compound, the optical isomer thereof, or the pharmaceutically acceptable salt thereof according to claim 1, wherein the compound has a structure of formula (III), (III)

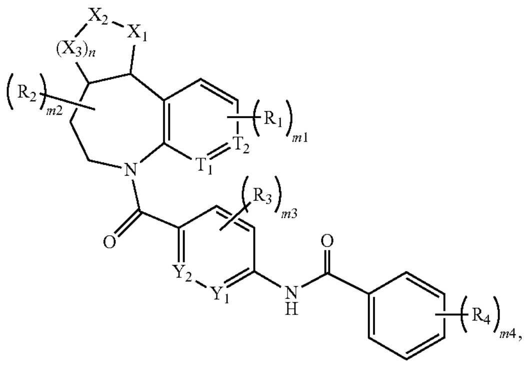

wherein $X_1$, $X_2$, $X_3$ are each independently selected from O, $C(R_A)_2$, and $NR_A$;

$T_1$, $T_2$ are each independently selected from N and $C(R_T)$;

$Y_1$, $Y_2$ are each independently selected from N and $C(R_Y)$;

$R_1$, $R_2$, $R_3$, $R_A$, $R_T$, $R_Y$ are each independently selected from H, F, Cl, Br, I, CN, OH, $NH_2$, $C_{1-6}$ alkyl, and $C_{1-6}$ heteroalkyl, and the $C_{1-6}$ alkyl or $C_{1-6}$ heteroalkyl is optionally substituted by 1, 2, or 3 R;

each $R_4$ is independently selected from H, F, Cl, Br, I, CN, OH, $NH_2$, $C_{1-6}$ alkyl, $C_{1-6}$ alkoxy, $C_{1-6}$ alkylamino, $C_{3-6}$ cycloalkyl, phenyl, and 5- to 6-membered heteroaryl, and the $C_{1-6}$ alkyl, $C_{1-6}$ alkoxy, $C_{1-6}$ alkylamino, $C_{3-6}$ cycloalkyl, phenyl, or 5- to 6-membered heteroaryl is optionally substituted by 1, 2, or 3 $R_{4a}$;

R, $R_{4a}$ are each independently selected from H, F, Cl, Br, I, CN, OH, $NH_2$, $C_{1-6}$ alkyl, $C_{1-6}$ alkoxy, and $C_{1-6}$ alkylamino, and the $C_{1-6}$ alkyl, $C_{1-6}$ alkoxy, and $C_{1-6}$ alkylamino are optionally substituted by 1, 2, or 3 R';

R' is selected from H, F, Cl, Br, I, CN, OH, $NH_2$, and $C_{1-6}$ alkyl;

m1, m2, m3, m4, n are each independently selected from 0, 1, or 2;

and when $X_1$, $X_3$ are selected from O at the same time, the compound of formula (III) is not selected from

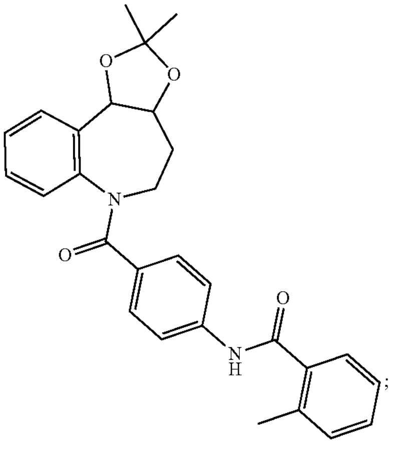 [SMILES: Cc1ccccc1C(=O)Nc1ccc(C(=O)N2CCC3OC(C)(C)OC3c3ccccc32)cc1]

;

the $C_{1-6}$ heteroalkyl or 5- to 6-membered heteroaryl comprises 1, 2, 3, or 4 heteroatoms or heteroatom groups independently selected from —O—, —NH—, —S—, —C(═O)—, —C(═O)O—, —S(═O)—, —S(═O)$_2$—, and N.

4. The compound, the optical isomer thereof, or the pharmaceutically acceptable salt thereof according to claim 1, wherein the compound has a structure of formula (IV), (IV)

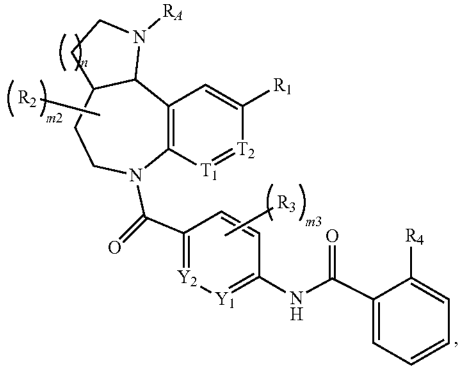

wherein $T_1$, $T_2$ are each independently selected from O, N, and C($R_T$);

$Y_1$, $Y_2$ are each independently selected from N and C($R_Y$);

$R_1$, $R_2$, $R_3$, $R_A$, $R_T$, $R_Y$ are each independently selected from H, F, Cl, Br, I, CN, OH, $NH_2$, $C_{1-6}$ alkyl, and $C_{1-6}$ heteroalkyl, and the $C_{1-6}$ alkyl or $C_{1-6}$ heteroalkyl is optionally substituted by 1, 2, or 3 R;

each $R_4$ is independently selected from H, F, Cl, Br, I, CN, OH, $NH_2$, $C_{1-6}$ alkyl, $C_{1-6}$ alkoxy, $C_{1-6}$ alkylamino, $C_{3-6}$ cycloalkyl, phenyl, and 5- to 6-membered heteroaryl, and the $C_{1-6}$ alkyl, $C_{1-6}$ alkoxy, $C_{1-6}$ alkylamino, $C_{3-6}$ cycloalkyl, phenyl, or 5- to 6-membered heteroaryl is optionally substituted by 1, 2, or 3 $R_{4a}$;

R, $R_{4a}$ are each independently selected from H, F, Cl, Br, I, CN, OH, $NH_2$, $C_{1-6}$ alkyl, $C_{1-6}$ alkoxy, and $C_{1-6}$ alkylamino, and the $C_{1-6}$ alkyl, $C_{1-6}$ alkoxy, and $C_{1-6}$ alkylamino are optionally substituted by 1, 2, or 3 R';

R' is selected from H, F, Cl, Br, I, CN, OH, $NH_2$, and $C_{1-6}$ alkyl;

m2, m3, n are each independently selected from 0, 1, or 2;

the $C_{1-6}$ heteroalkyl or 5- to 6-membered heteroaryl comprises 1, 2, 3, or 4 heteroatoms or heteroatom groups independently selected from —O—, —NH—, —S—, —C(═O)—, —C(═O)O—, —S(═O)—, —S(═O)$_2$—, and N.

5. The compound, the optical isomer thereof, or the pharmaceutically acceptable salt thereof according to claim 4, wherein the compound has a structure of formula (V-1), (V-2), (V-3), or (V-4), (V-1)

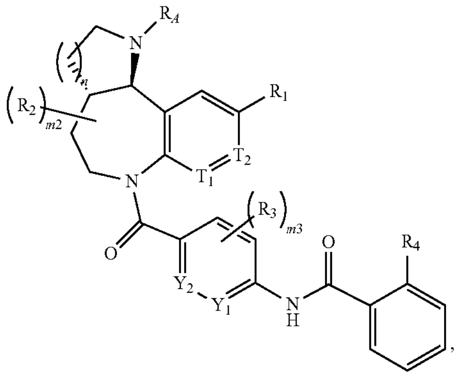

(V-2)

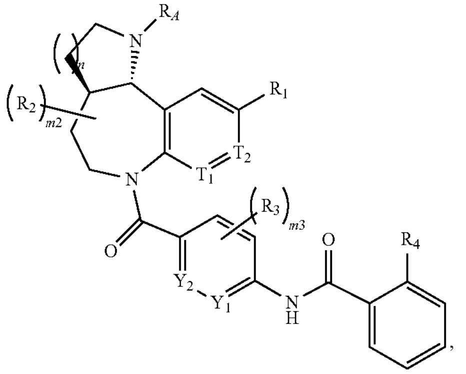

(V-3)

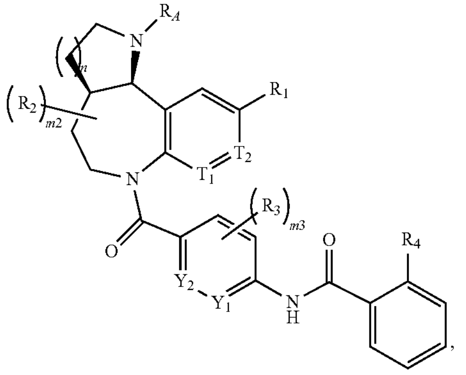

(V-4)

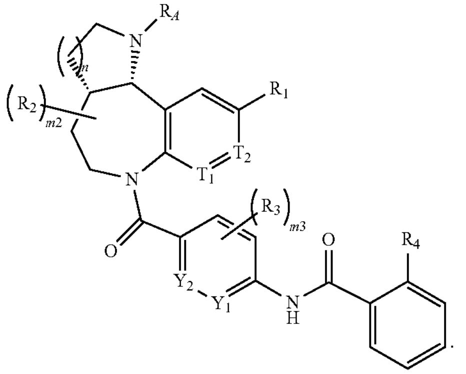

6. The compound, the optical isomer thereof, or the pharmaceutically acceptable salt thereof according to claim 1, wherein $R_4$ is selected from H, F, Cl, Br, I, CN, OH, $NH_2$, $CH_3$, $CF_3$,

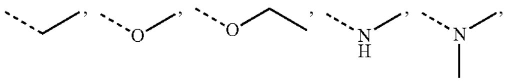

cyclopropyl, cyclobutyl, cyclopentyl, phenyl, pyridyl, pyrimidinyl, thienyl, and thiazolyl.

7. The compound, the optical isomer thereof, or the pharmaceutically acceptable salt thereof according to claim 1, wherein ring A is selected from azetidinyl, oxetanyl, pyrrolidinyl, tetrahydrofuranyl, cyclobutyl, cyclopentyl, and cyclohexyl, and the azetidinyl, oxetanyl, pyrrolidinyl, tetrahydrofuranyl, cyclobutyl, cyclopentyl, or cyclohexyl is optionally substituted by 1 or 2 $R_A$.

8. The compound, the optical isomer thereof, or the pharmaceutically acceptable salt thereof according to claim 7, wherein ring A is selected from

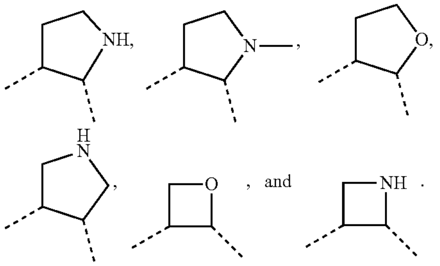

, and

9. The compound, the optical isomer thereof, or the pharmaceutically acceptable salt thereof according to claim 1, wherein ring B is selected from phenyl and pyridyl, and the phenyl or pyridyl is optionally substituted by 1, 2, or 3 $R_3$.

10. The compound, the optical isomer thereof, or the pharmaceutically acceptable salt thereof according to claim 9, wherein ring B is selected from

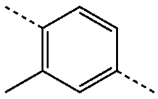

and

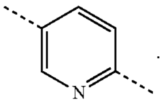

.

11. The compound, the optical isomer thereof, or the pharmaceutically acceptable salt thereof according to claim 1, wherein ring C is selected from

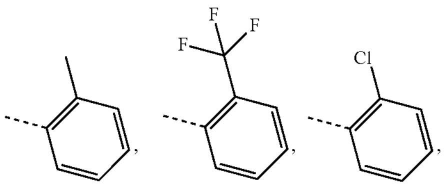

, and

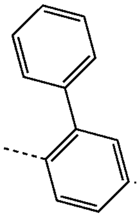

.

12. A compound of the following formula, an optical isomer thereof, or a pharmaceutically acceptable salt thereof, selected from:

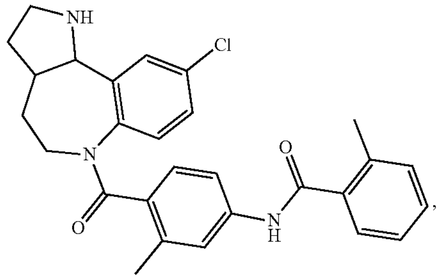

,

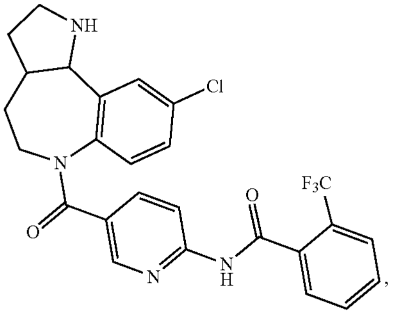

,

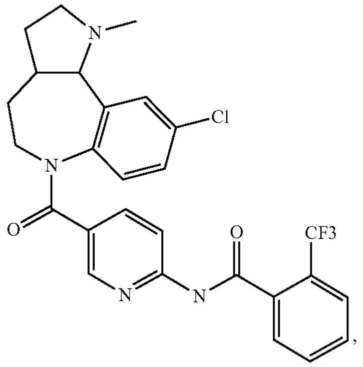

,

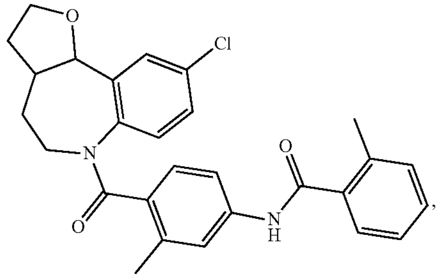

,

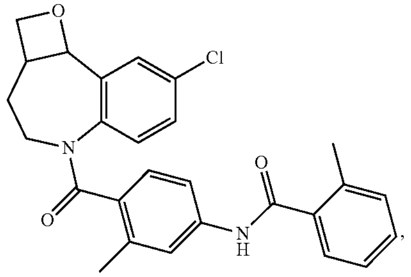

,

-continued

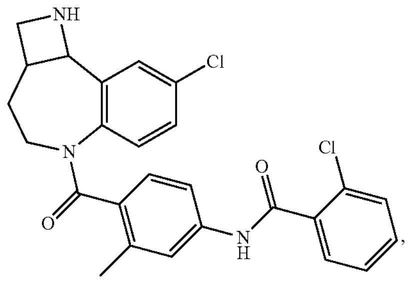

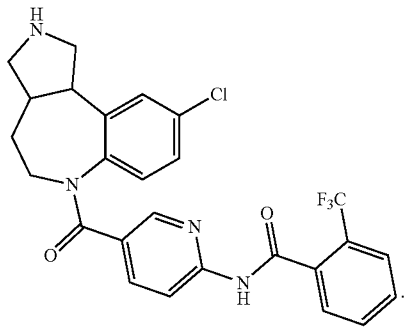

13. A method for preventing or treating diseases related to arginine vasopressin V1a receptor, arginine vasopressin V1b receptor, arginine vasopressin V2 receptor, sympathetic nervous system, or renin-angiotensin-aldosterone system in a subject in need thereof, comprising administering the compound, the optical isomer thereof, or the pharmaceutically acceptable salt thereof according to claim 1 to the subject.

14. The method according to claim 13, wherein the diseases related to arginine vasopressin V1a receptor, arginine vasopressin V1b receptor, arginine vasopressin V2 receptor, sympathetic nervous system, or renin-angiotensin-aldosterone system comprise: hypertension, Reye's syndrome, dysmenorrhea, premature delivery, corticotropin-releasing hormone secretion disorder, adrenal hyperplasia, depression, chronic congestive heart failure, liver cirrhosis, syndrome of inappropriate antidiuretic hormone secretion, hyponatremia caused by chronic heart failure/liver cirrhosis/inappropriate antidiuretic hormone secretion, or polycystic kidney disease.

15. A compound of the following formula, an optical isomer thereof, or a pharmaceutically acceptable salt thereof, selected from:

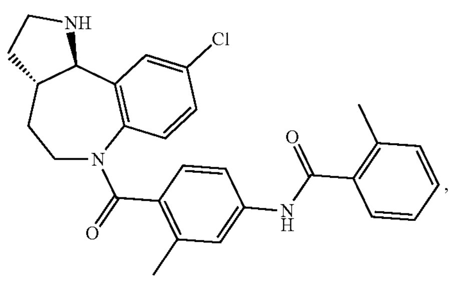

-continued

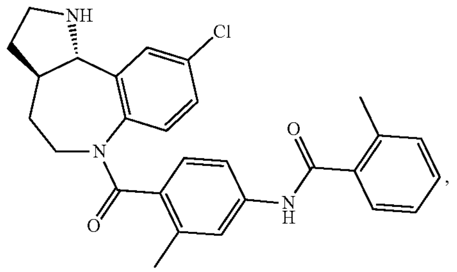

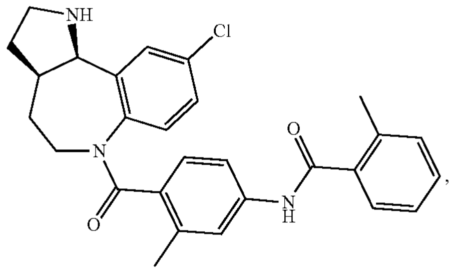

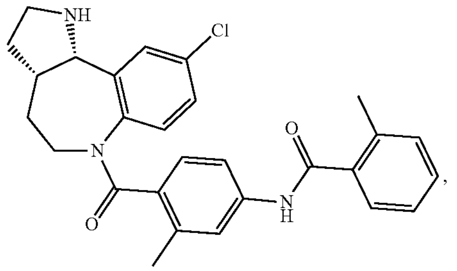

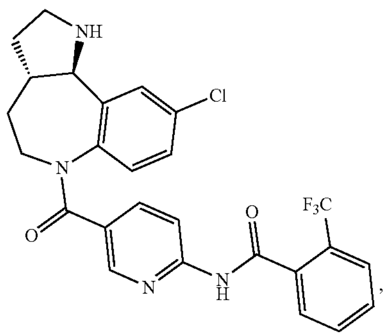

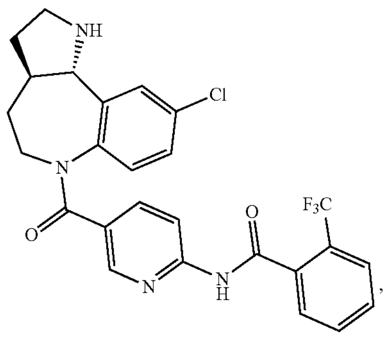

-continued
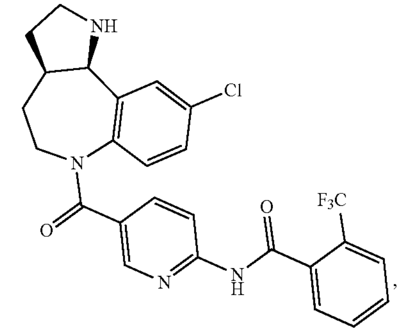
,
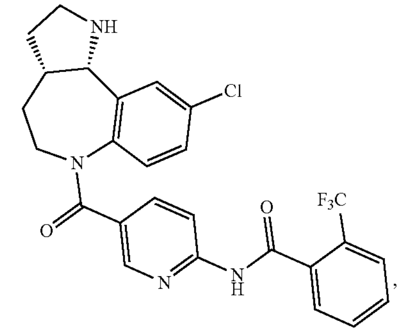
,
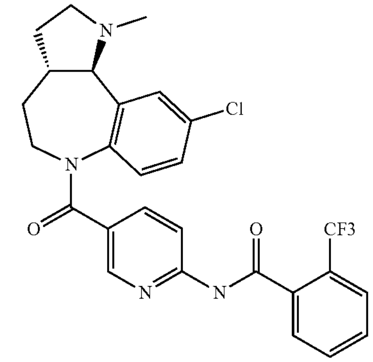
,
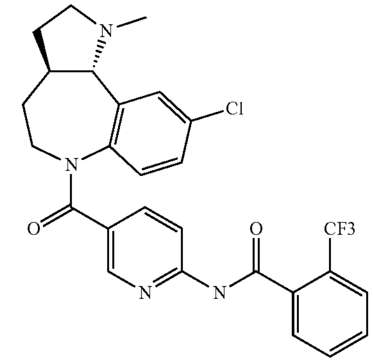
,
-continued
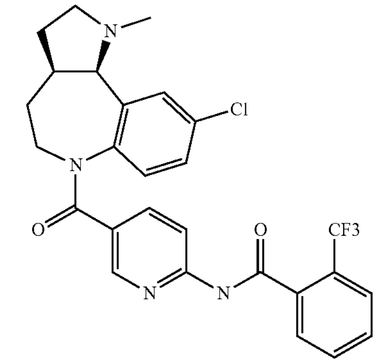
,
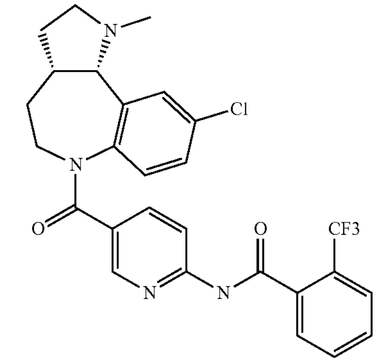
,
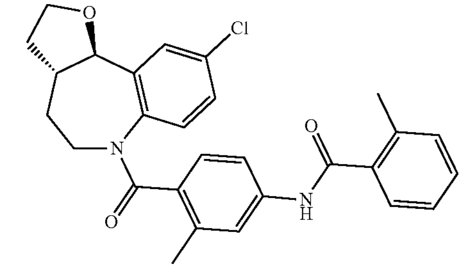
,
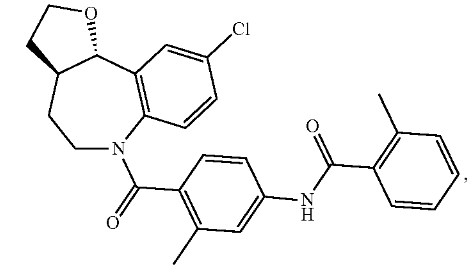
,
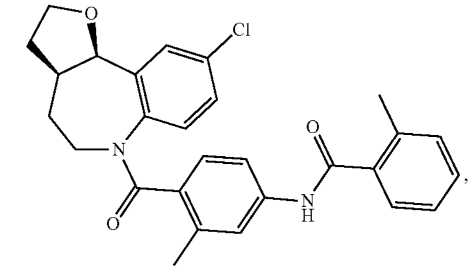
, -continued
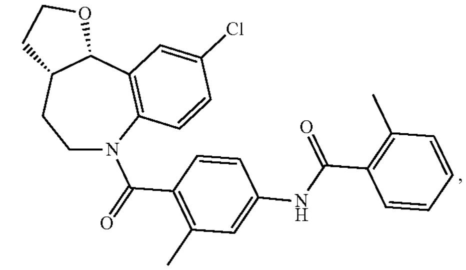
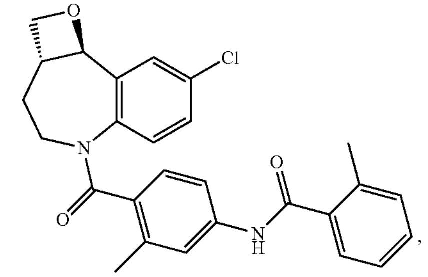
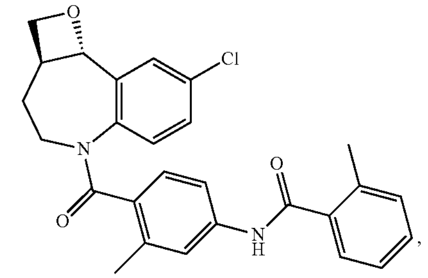
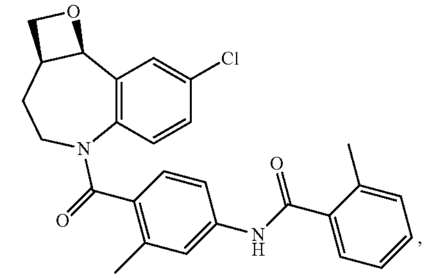
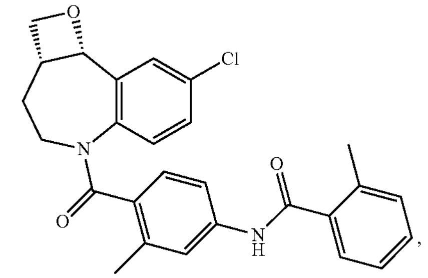
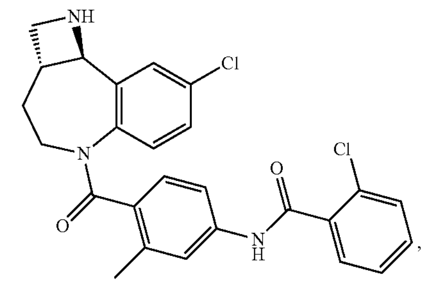
-continued
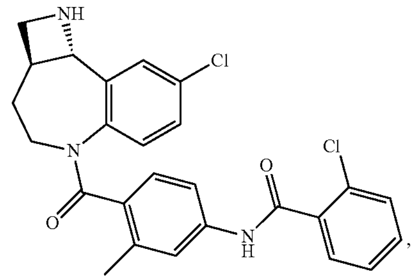
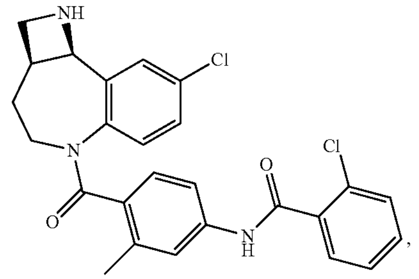
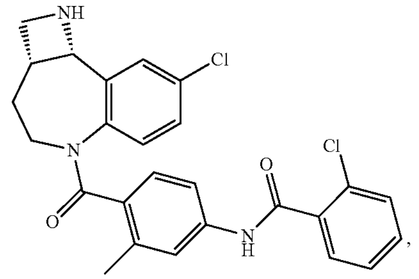
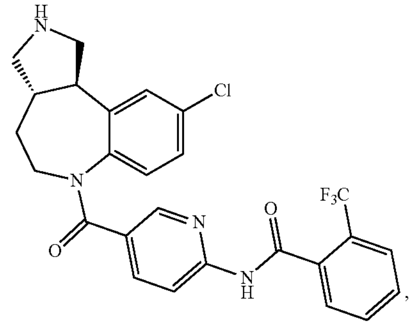
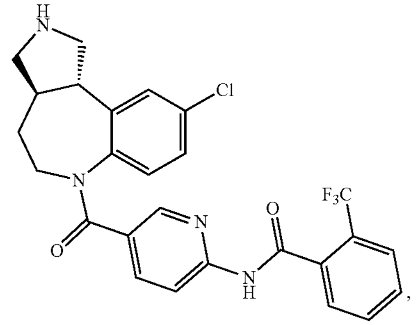

-continued
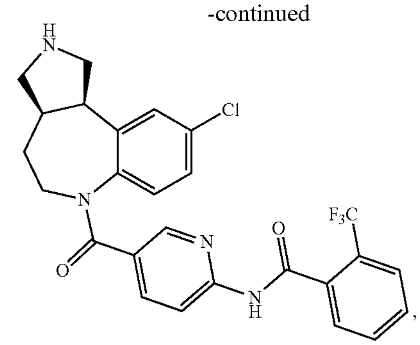
, and
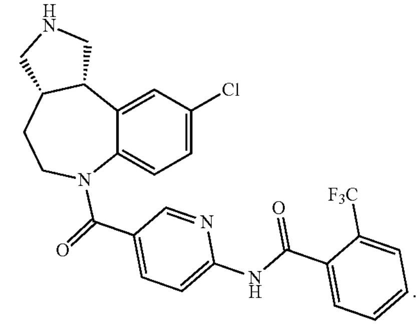
.
* * * * *